US006268130B1

(12) United States Patent
Kleyn et al.

(10) Patent No.: US 6,268,130 B1
(45) **Date of Patent: *Jul. 31, 2001**

(54) RP COMPOSITIONS AND DIAGNOSTIC USES THEREFOR

(75) Inventors: Patrick W. Kleyn, Cambridge; Karen J. Moore, Maynard, both of MA (US)

(73) Assignee: Millennium Pharmaceuticals, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/955,918

(22) Filed: Oct. 22, 1997

Related U.S. Application Data

(60) Division of application No. 08/847,040, filed on May 1, 1997, which is a continuation-in-part of application No. 08/697,766, filed on Aug. 29, 1996, which is a continuation-in-part of application No. 08/631,200, filed on Apr. 12, 1996, now Pat. No. 5,646,040.

(51) Int. Cl.[7] .............................. C12Q 1/68; C12P 19/34; C07H 21/04

(52) U.S. Cl. .......................... 435/6; 435/91.2; 536/24.31; 536/24.33; 536/23.5

(58) Field of Search ................... 435/6, 91.2; 536/24.31, 536/24.33, 23.5; 935/8, 9, 78

(56) References Cited

U.S. PATENT DOCUMENTS

| | | | |
|---|---|---|---|
| 4,965,188 | 10/1990 | Mullis et al. | 435/6 |
| 5,646,040 * | 7/1997 | Kleyn et al. | 435/325 |
| 5,686,598 | 11/1997 | North et al. | 536/23.5 |

OTHER PUBLICATIONS

CLONTECH 95/96 Catalog, 'Quick–Clone™ cDNA' CLONTECH Laboratories, 33–35.

Keen, T.J. et al. (1995) "A YAC Contig Spanning the Dominant Retinitis Pigmentosa Locus (RP9) on Chromosome 7p" *Genomics*, vol. 28, 383–388.

Knowles, J.A. et al. (1994) "Identification of a Locus, Distinct from RDS–Peripherin, for Autosomal Recessive Retinitis Pigmentosa on Chromosome 6p" *Human Molecular Genetics*, vol. 3, No. 8, 1401–1403.

Mazzarella, R. et al. (1994) "Physical Linkage of Expressed Sequence Tags (ESTs) to Polymorphic Markers on the X Chromosome" *Human Molecular Genetics*, vol. 3, No. 7, 1095–1101.

White, O. et al. (1996) "TDB: New Databases for Biological Discovery" *Methods in Enzymology*, vol. 266, 27–40.

Hillier et al, GenBank Accession No. H96925, Dec. 1995.

GenBank Accession No. H92408, Nov. 1995, Hillier et al.

Macke et al. GenBank Accession No. W27507, May 1996.

Feng, Z. et al., "Characterization and Regulation of Two Testicular Inhibin/Activin βB–Subunit Messenger Ribonucleic Acids that are Transcribed from Alternate Initiation Sites," *Endocrinology*, vol. 136, No. 3, 947–955 (1955).

Kleyn, P. et al., "Identification and Characterization of the Mouse Obesity Gene Tubby: A Member of a Novel Gene Family," *Cell*, vol. 85, 281–290 (1996).

Noben–Trauth, K. et al., "A Candidate Gene for the Mouse Mutation Tubby," *Nature*, vol. 380, 534–538 (1996).

Vambutas, V. and Wolgemuth, D., "Identification and Characterization of the Developmentally Regulated Pattern of Expression in the Testis of a Mouse Gene Exhibiting Similarity to the Family of Phosphodiesterases," *Biochimica et Biophysica Acta*, vol. 1217, 203–206 (1994).

GenBank™ Accession No. D88493 for *Desulfovibrio Vulgaris DNA for Flaxodoxin*; 1994.

Promega Catalog, p. 166, 1992/1993.*

* cited by examiner

*Primary Examiner*—Carla J. Myers
(74) *Attorney, Agent, or Firm*—Lahive & Cockfield, LLP; Amy E. Mandragouras

(57) ABSTRACT

The invention provides isolated nucleic acids molecules, designated retinitis pigmentosa ("rp") nucleic acid molecules, which encode polypeptides involved in the regulation of sensory functions, e.g., retinal functions, e.g., functions of the rod and cone photoreceptor cells of the retina, body weight, and/or metabolic functions. The invention also provides antisense nucleic acid molecules, expression vectors containing rp nucleic acid molecules, host cells into which the expression vectors have been introduced, and nonhuman transgenic animals in which an rp gene has been introduced or disrupted. The invention still further provides isolated rp polypeptides, fusion proteins, antigenic peptides, and anti-rp antibodies. Diagnostic, screening, and therapeutic methods utilizing compositions of the invention are also provided.

10 Claims, 11 Drawing Sheets

FIG.1

```
GAATTCCGGGAAGCTGAATGGAAGCCGGGGAGAAGTGTTGAAAGTGGAAACCCAAGCCCAGGGGAGATCCCTAGGGTGA

GGAGCCCGAGGGGGTGCGCCCAGGCTTGGGGGTAGCGGGTAGAGGCGCTGCCTCGCGGACCCGCGGATGGGACCCTGTC

TGAACCCCGCATCTCGGCTCAGCTGGGCGGAGGGGGAGGCCGCGGGAGGAGCCTTCCCCAGACCCAGCCCAGGCCCGGG

CGCCGCAGACGGTCTACGCCAGGTTCCTCAGGGACCCCGAGGCCAAGAAGCGCGACCCCCGGGAAACCTTTCTGGTAGC

CCGTGCCCCAGACGCGGAGGACGAGGAGGAGGAGGAAGAGGAGGACGAGGAGGACGAAGAAGATGAGCMGARGAAAAGA

AAGAGAAAATCCTTCTGCCTCCCAAGAARCCCCTGAGAGAGAAGAGCTCCGCAGACCTGAANGANAAGAAGGCCAANGC

CCASGGCCCAAGGGGAGACCTGGGAAGCCCTGACCCCCCACCGAAACCTCTGCGTGTTAGGAATAAGGAAGCTCCAGCA

                 M   R   K   T   K   K   K   G   S   G   E   A   D   K   D   P    16
GGGGAGGGGACCAAG ATG AGA AAG ACC AAG AAG AAA GGG TCT GGG GAG GCC GAC AAG GAC CCC   48

 S   G   S   P   A   S   A   R   K   S   P   A   A   M   F   L   V   G   E   G    36
TCA GGG AGC CCA GCC AGT GCG AGG AAG AGC CCA GCA GCC ATG TTT CTG GTT GGG GAA GGC   108

 S   P   D   K   K   A   L   K   K   K   G   T   P   K   G   A   R   K   E   E    56
AGT CCT GAC AAG AAA GCC CTG AAG AAG AAA GGC ACT CCC AAA GGC GCG AGG AAG GAG GAA   168

 E   E   E   E   E   A   A   T   V   T   K   N   S   N   Q   K   G   K   A   K    76
GAA GAG GAG GAG GAG GCA GCT ACG GTG ACA AAG AAC AGC AAT CAA AAG GGC AAA GCC AAA   228

 G   K   G   K   K   K   A   K   E   E   R   A   P   S   P   P   V   E   V   D    96
GGA AAA GGC AAA AAG AAA GCG AAG GAG GAG AGG GCC CCG TCT CCC CCC GTG GAG GTG GAC   288
```

FIG.1A

```
 E   P   R   E   F   V   F   R   P   A   P   Q   G   R   T   V   R   C   R   L   116
GAA CCC CGG GAG TTT GTG TTC CGG CCT GCC CCC CAG GGC CGC ACG GTG CGC TGC CGG CTG  348

 T   R   D   K   K   G   M   D   R   G   M   Y   P   S   Y   F   L   H   L   D   136
ACC CGG GAC AAA AAG GGC ATG GAT CGA GGC ATG TAT CCC TCC TAC TTC CTG CAC CTG GAC  408

 T   E   K   K   V   F   L   L   A   G   R   K   R   K   R   S   K   T   A   N   156
ACG GAG AAG AAG GTG TTC CTC TTG GCT GGC AGG AAA CGA AAA CGG AGC AAG ACA GCC AAT  468

 Y   L   I   S   I   D   P   T   N   L   S   R   G   G   E   N   F   I   G   K   176
TAC CTC ATC TCC ATC GAC CCT ACC AAT CTG TCC CGA GGA GGG GAG AAT TTC ATC GGG AAG  528

 L   R   S   N   L   L   G   N   R   F   T   V   F   D   N   G   Q   N   P   Q   196
CTG AGG TCC AAC CTC CTG GGG AAC CGC TTC ACG GTC TTT GAC AAC GGG CAG AAC CCA CAG  588

 R   G   Y   S   T   N   V   A   S   L   R   Q   E   L   A   A   V   I   Y   E   216
CGT GGG TAC AGC ACT AAT GTG GCA AGC CTT CGG CAG GAG CTG GCA GCT GTG ATC TAT GAA  648

 T   N   V   L   G   F   R   G   P   R   R   M   T   V   I   I   P   G   M   S   236
ACC AAC GTG CTG GGC TTC CGT GGC CCC CGG CGC ATG ACC GTC ATC ATT CCT GGC ATG AGT  708

 A   E   N   E   R   V   P   I   R   P   R   N   A   S   D   G   L   L   V   R   256
GCG GAG AAC GAG AGG GTC CCC ATC CGG CCC CGA AAT GCT AGT GAC GGC CTG CTG GTG CGC  768

 W   Q   N   K   T   L   E   S   L   I   E   L   H   N   K   P   P   V   W   N   276
TGG CAG AAC AAG ACG CTG GAG AGC CTC ATA GAA CTG CAC AAC AAG CCA CCT GTC TGG AAC  828
```

FIG.1B

```
 D   D   S   G   S   Y   T   L   N   F   Q   G   R   V   T   Q   A   S   V   K    296
GAT GAC AGT GGC TCC TAC ACC CTC AAC TTC CAA GGC CGG GTC ACC CAG GCC TCA GTC AAG   888

 N   F   Q   I   V   H   A   D   D   P   D   Y   I   V   L   Q   F   G   R   V    316
AAC TTC CAG ATT GTC CAC GCT GAT GAC CCC GAC TAT ATC GTG CTG CAG TTC GGC CGC GTG   948

 A   E   D   A   F   T   L   D   Y   R   Y   P   L   C   A   L   Q   A   F   A    336
GCG GAG GAC GCC TTC ACC CTA GAC TAC CGG TAC CCG CTG TGC GCC CTG CAG GCC TTC GCC   1008

 I   A   L   S   S   F   D   G   K   L   A   C   E   *                            350
ATC GCC CTC TCC AGT TTC GAC GGG AAG CTG GCC TGC GAG TGA                           1050

CCCCAGCAGCCCCTCAGCGCCCCCAGAGCCCGTCAGCGTGGGGAAAGGATTCAGTGGAGGCTGGCAGGGTCCCTCCAG

CAAAGCTCCCGCGGAAAACTGCTCCTGTGTCGGGGCTGACCTCTCACTGCCTCTCGGTGACCTCCGTCCTCTCCCCAGC

CTGGCACAGGCCGAGGCAGGAGGAGCCCGGACGGCGGGTAGGACGGAGATGAAGAACATCTGGAGTTGGAGCCGCACAT

CTGGTCTCGGAGCTCGCCTGCGCCGCTGTGCCCCCCTCCTCCCCGCGCCCCAGTCACTTCCTGTCCGGGAGCAGTAGTC

AGTGTTGTTTTAACCTCCCCTCTCCCCGGGACCGCGCTAGGGCTCCGAGGAGCTGGGGCGGGCTAGGAGGAGGGGGTAG

GTGATGGGGGACGAGGGCCAGGCACCCACATCCCCAATAAAGCCGCGTCCTTGGCMAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAAAAAAAAAAAAAAA

AAAACCGGAATTC
```

FIG. 2

```
V   I   K   N   S   N   Q   K   G   K   A   K   G   K   G   K   K   K   A   K     20
GTG ATA AAG AAC AGC AAT CAA AAG GGC AAA GCC AAA GGA AAA GGC AAA AAG AAA GCG AAG   60

E   E   R   A   P   S   P   P   V   E   V   D   E   P   R   E   F   V   L   R     40
GAG GAG AGG GCC CCG TCT CCC CCC GTG GAG GTG GAC GAA CCC CGG GAG TTT GTG CTC CGG   120

P   A   P   Q   G   R   T   V   R   C   R   L   T   R   D   K   K   G   M   D     60
CCT GCC CCC CAG GGC CGC ACG GTG CGC TGC CGG CTG ACC CGG GAC AAA AAG GGC ATG GAT   180

R   G   M   Y   P   S   Y   F   L   H   L   D   T   E   K   K   V   F   L   L     80
CGA GGC ATG TAT CCC TCC TAC TTC CTG CAC CTG GAC ACG GAG AAG AAG GTG TTC CTC TTG   240

A   G   R   K   R   K   R   S   K   T   A   N   Y   L   I   S   I   D   P   T     100
GCT GGC AGG AAA CGA AAA CGG AGC AAG ACA GCC AAT TAC CTC ATC TCC ATC GAC CCT ACC   300

N   L   S   R   G   G   E   N   F   I   G   K   L   R   S   N   L   L   G   N     120
AAT CTG TCC CGA GGA GGG GAG AAT TTC ATC GGG AAG CTG AGG TCC AAC CTC CTG GGG AAC   360

R   F   T   V   F   D   N   G   Q   N   P   Q   R   G   Y   S   T   N   V   A     140
CGC TTC ACG GTC TTT GAC AAC GGG CAG AAC CCA CAG CGT GGG TAC AGC ACT AAT GTG GCA   420

S   L   R   Q   E   L   A   A   V   I   Y   E   T   N   V   L   G   F   R   G     160
AGC CTT CGG CAG GAG CTG GCA GCT GTG ATC TAT GAA ACC AAC GTG CTG GGC TTC CGT GGC   480

P   R   R   M   T   V   I   I   P   G   M   S   A   E   N   E   R   V   P   I     180
CCC CGG CGC ATG ACC GTC ATC ATT CCT GGC ATG AGT GCG GAG AAC GAG AGG GTC CCC ATC   540

R   P   R   N   A   S   D   G   L   L   V   R   W   Q   N   K   T   L   E   S     200
CGG CCC CGA AAT GCT AGT GAC GGC CTG CTG GTG CGC TGG CAG AAC AAG ACG CTG GAG AGC   600
```

FIG.2A

```
 L   I   E   L   H   N   K   P   P   V   W   N   D   D   S   G   S   Y   T   L     220
CTC ATA GAA CTG CAC AAC AAG CCA CCT GTC TGG AAC GAT GAC AGT GGC TCC TAC ACC CTC    660

 N   F   Q   G   R   V   T   Q   A   S   V   K   N   F   Q   I   V   H   A   D     240
AAC TTC CAA GGC CGG GTC ACC CAG GCC TCA GTC AAG AAC TTC CAG ATT GTC CAC GCT GAT    720

 D   P   D   Y   I   V   L   Q   F   G   R   V   A   E   D   A   F   T   L   D     260
GAC CCC GAC TAT ATC GTG CTG CAG TTC GGC CGC GTG GCG GAG GAC GCC TTC ACC CTA GAC    780

 Y   R   Y   P   L   C   A   L   Q   A   F   A   I   A   L   S   S   F   D   G     280
TAC CGG TAC CCG CTG TGC GCC CTG CAG GCC TTC GCC ATC GCC CTC TCC AGT TTC GAC GGG    840

 K   L   A   C   E   *                                                             285
AAG CTG GCC TGC GAG TGACCCCAGCAGCCCCTCAGCGCCCCCAGAGCCCGTCAGCGTGGG                  900

GGAAAGGATTCAGTGGAGGCTGGCAGGGTCCCTCCAGCAAAGCTCCCGCGGAAAACTGCT                       960

CCTGTGTCGGGGCTGACCTCTCACTGCCTCTCGGTGACCTCCGTCCTCTCCCCAGCCTGG                      1020

CACAGGCCGAGGCAGGAGGAGCCCGGACGGCGGGTAGGACGGAGATGAAGAACATCTGGA                      1080

GTTGGAGCCGCACATCTGGTCT CGGACCTCGCCTGCGCCGCTGTGCCCCCCTCCTCCCCG                     1140

CGCCCCAGTCACTTCCTGTCCGGGAGCAGTAGTCATTGTTGTTTTAACCTCCCCTCTCCC                      1200

CGGGACCGCGCTAGGGCTCCGAGGAGCTGGGGCGGGCTAGGAGGAGGGGGTAGGTGATGG                      1260

GGGACGAGGGCCAGGCACCCACATCCCCAATAAAGCCGCGTCCTTGGCAAAAAAAAAAAA                      1320

AAAAAAAAAAAAAAAAAA                                                                1338
```

FIG. 3

```
                                                  CTGCAGGATTCGGCACGAGCAGCGGTCGGGCCGGGGA

GGATGCGGCCCGGGGCGGCCCGAGAGTTGAGCAGGGTCCCCGCGCCAGCCCCGAGCGGTCCCGGCCACCGGAGCCGCAG

                            M   T   S   K   P   H   S   D   W   I   P   Y   S   V    14
CCGCCGCCCCGCCCCCGGGAGAC ATG ACT TCC AAG CCG CAT TCC GAC TGG ATT CCT TAC AGT GTC    42

 L   D   D   E   G   S   N   L   R   Q   Q   K   L   D   R   Q   R   A   L   L    34
CTA GAT GAT GAG GGC AGC AAC CTG AGG CAG CAG AAG CTC GAC CGG CAG CGG GCC CTG TTG   102

 E   Q   K   Q   K   K   K   R   Q   E   P   L   M   V   Q   A   N   A   D   G    54
GAA CAG AAG CAG AAG AAG AAG CGC CAA GAG CCC TTG ATG GTA CAG GCC AAT GCA GAT GGA   162

 R   P   R   S   R   R   A   R   Q   S   E   E   Q   A   P   L   V   E   S   Y    74
CGG CCC CGG AGT CGG CGA GCC CGG CAG TCA GAG GAG CAA GCC CCC CTG GTG GAG TCC TAC   222

 L   S   S   S   G   S   T   S   Y   Q   V   Q   E   A   D   S   I   A   S   V    94
CTC AGC AGC AGT GGC AGC ACC AGC TAC CAA GTT CAA GAG GCC GAC TCG ATT GCC AGT GTA   282

 Q   L   G   A   T   R   P   P   A   P   A   S   A   K   K   S   K   G   A   A   114
CAG CTG GGA GCC ACC CGC CCA CCA GCA CCA GCT TCA GCC AAG AAA TCC AAG GGA GCG GCT   342

 A   S   G   G   Q   G   G   A   P   R   K   E   K   K   G   K   H   K   G   T   134
GCA TCT GGG GGC CAG GGT GGA GCC CCT AGG AAG GAG AAG AAG GGA AAG CAT AAA GGC ACC   402

 S   G   P   A   T   L   A   E   D   K   S   E   A   Q   G   P   V   Q   I   L   154
AGC GGG CCA GCA ACT CTG GCA GAA GAC AAG TCT GAG GCC CAA GGC CCA GTG CAG ATC TTG   462
```

FIG.3A

```
 T   V   G   Q   S   D   H   D   K   D   A   G   E   T   A   A   G   G   G   A    174
ACT GTG GGA CAG TCA GAC CAC GAC AAG GAT GCG GGA GAG ACA GCA GCC GGC GGG GGC GCA   522

 Q   P   S   G   Q   D   L   R   A   T   M   Q   R   K   G   I   S   S   S   M    194
CAG CCC AGT GGG CAG GAC CTC CGT GCC ACG ATG CAG AGG AAG GGC ATC TCC AGC AGC ATG   582

 S   F   D   E   D   E   D   E   D   E   N   S   S   S   S   S   Q   L   N   S    214
AGC TTT GAC GAG GAC GAG GAT GAG GAT GAA AAC AGC TCC AGC TCC TCC CAG CTA AAC AGC   642

 N   T   R   P   S   S   A   T   S   R   K   S   I   R   E   A   A   S   A   P    234
AAC ACC CGC CCT AGT TCT GCC ACT AGC AGA AAG TCC ATC CGG GAG GCA GCT TCA GCC CCC   702

 S   P   A   A   P   E   P   P   V   D   I   E   V   Q   D   L   E   E   F   A    254
AGC CCA GCC GCC CCA GAG CCA CCA GTG GAT ATT GAG GTC CAG GAT CTA GAG GAG TTT GCA   762

 L   R   P   A   P   Q   G   I   T   I   K   C   R   I   T   R   D   K   K   G    274
CTG AGG CCA GCC CCA CAA GGG ATC ACC ATC AAA TGC CGC ATC ACT CGG GAC AAG AAG GGG   822

 M   D   R   G   M   Y   P   T   Y   F   L   H   L   D   R   E   D   G   K   K    294
ATG GAC CGC GGC ATG TAC CCC ACC TAC TTT CTG CAC CTA GAC CGT GAG GAT GGC AAG AAG   882

 V   F   L   L   A   G   R   K   R   K   K   S   K   T   S   N   Y   L   I   S    314
GTG TTC CTC CTG GCG GGC AGG AAG AGA AAG AAG AGT AAA ACT TCC AAT TAC CTC ATC TCT   942

 V   D   P   T   D   L   S   R   G   G   D   S   Y   I   G   K   L   R   S   N    334
GTG GAC CCA ACA GAC TTG TCT CGG GGA GGC GAT AGC TAT ATC GGG AAA TTG CGG TCC AAC  1002

 L   M   G   T   K   F   T   V   Y   D   N   G   V   N   P   Q   K   A   S   S    354
CTG ATG GGC ACC AAG TTC ACC GTT TAT GAC AAT GGC GTC AAC CCT CAG AAG GCA TCC TCT  1062
```

FIG.3B

```
S   T   L   E   S   G   T   L   R   Q   E   L   A   A   V   C   Y   E   T   N     374
TCC ACG CTG GAA AGC GGA ACC TTG CGC CAG GAG CTG GCA GCG GTG TGC TAT GAG ACA AAT   1122

V   L   G   F   K   G   P   R   K   M   S   V   I   V   P   G   M   N   M   V     394
GTC CTA GGC TTC AAG GGA CCT CGG AAG ATG AGT GTG ATC GTC CCA GGC ATG AAC ATG GTT   1182

H   E   R   V   C   I   R   P   R   N   E   H   E   T   L   L   A   R   W   Q     414
CAT GAG AGA GTC TGT ATC CGC CCC CGC AAT GAA CAT GAG ACC CTG TTA GCA CGC TGG CAG   1242

N   K   N   T   E   S   I   I   E   L   Q   N   K   T   P   V   W   N   D   D     434
AAC AAG AAC ACG GAG AGC ATC ATT GAG CTG CAG AAC AAG ACG CCA GTC TGG AAT GAT GAC   1302

T   Q   S   Y   V   L   N   F   H   G   R   V   T   Q   A   S   V   K   N   F     454
ACA CAG TCC TAT GTA CTT AAC TTC CAC GGC CGT GTC ACA CAG GCT TCT GTG AAG AAC TTC   1362

Q   I   I   H   G   N   D   P   D   Y   I   V   M   Q   F   G   R   V   A   E     474
CAG ATC ATC CAC GGA AAT GAC CCG GAC TAC ATC GTC ATG CAG TTT GGC CGG GTA GCA GAA   1422

D   V   F   T   M   D   Y   N   Y   P   L   C   A   L   Q   A   F   A   I   A     494
GAT GTG TTC ACC ATG GAT TAC AAC TAC CCA CTG TGT GCA CTG CAG GCC TTC GCC ATT GCT   1482

L   S   S   F   D   S   K   L   A   C   E   *                                     505
CTG TCC AGC TTT GAC AGC AAG CTG GCC TGC GAG TAG AGGCCCCCCACTGCCGTTAGGTGGCCCAGTC   1515

CGGAGTGGAGCTTGCCTGCCTGCCAAGACAGGCCTGCCTACCCTCTGTTCATAGGCCCTCTATGGGCTTTCTGGTCTGA

CCAACCAGAGATTGGTTTGCTCTGCCTCTGCTGCTTGA
```

FIG.4

```
                                                     TGGCGTGCAGCAGGGGCCTCGGCGGGGCCC

AGCCCNCCGGTCCCGGGGAGGATACGTCCCGGGGGCGGCCCGGGAGCTGAGCAGGCCCCCCGCGCCGGCCCCTCCGGGC

                                                 M   T   S   K   P   H   S   D   W     9
CCCGGCCTCCAGAGCCGCAGCCACCGCCCCGCCCCCGAGAGAC ATG ACT TCC AAG CCG CAT TCC GAC TGG   27

 I   P   Y   S   V   L   D   D   E   G   R   N   L   R   Q   Q   K   L   D   R    29
ATT CCC TAC AGT GTC TTA GAT GAT GAG GGC AGA AAC CTG AGG CAG CAG AAG CTT GAT CGG   87

 Q   R   A   L   L   E   Q   K   Q   K   K   K   R   Q   E   P   L   M   V   Q    49
CAG CGG GCC CTG CTG GAG CAG AAG CAG AAG AAG AAG CGC CAG GAG CCC CTG ATG GTG CAG  147

 A   N   A   D   G   R   P   R   S   R   R   A   R   Q   S   E   E   Q   A   P    69
GCC AAT GCA GAT GGG CGG CCC CGG AGC CGG CGG GCC CGG CAG TCA GAG GAA CAA GCC CCC  207

 L   V   E   S   Y   L   S   S   S   G   S   T   S   Y   Q   V   Q   E   A   D    89
CTG GTG GAG TCC TAC CTC AGC AGC AGT GGC AGC ACC AGC TAC CAA GTT CAA GAG GCC GAC  267

 S   L   A   S   V   Q   L   G   A   T   R   P   T   A   P   A   S   A   K   R   109
TCA CTC GCC AGT GTG CAG CTG GGA GCC ACG CGC CCA ACA GCA CCA GCT TCA GCC AAG AGA  327

 T   K   A   A   A   T   A   G   G   Q   G   G   A   A   R   K   E   K   K   G   129
ACC AAG GCG GCA GCT ACA GCA GGG GGC CAG GGT GGC GCC GCT AGG AAG GAG AAG AAG GGA  387

 K   H   K   G   T   S   G   P   A   A   L   A   E   D   K   S   E   A   Q   G   149
AAG CAC AAA GGC ACC AGC GGG CCA GCA GCA CTG GCA GAA GAC AAG TCT GAG GCC CAA GGC  447

 P   V   Q   I   L   T   V   G   Q   S   D   H   A   Q   D   A   G   E   T   A   169
CCA GTG CAG ATT CTG ACT GTG GGC CAG TCA GAC CAC GCC CAG GAC GCA GGG GAG ACG GCA  507
```

FIG.4A

```
 A   G   G   G   E   R   P   S   G   Q   D   L   R   A   T   M   Q   R   K   G    189
GCT GGT GGG GGC GAA CGG CCC AGC GGG CAG GAT CTC CGT GCC ACG ATG CAG AGG AAG GGC   567

 I   S   S   S   M   S   F   D   E   D   E   E   D   E   E   E   N   S   S   S    209
ATC TCC AGC AGC ATG AGC TTT GAC GAG GAT GAG GAG GAT GAG GAG GAG AAT AGC TCC AGC   627

 S   S   Q   L   N   S   N   T   R   P   S   S   A   T   S   R   K   S   V   R    229
TCC TCC CAG CTA AAT AGT AAC ACC CGC CCC AGC TCT GCT ACT AGC AGG AAG TCC GTC AGG   687

 E   A   A   S   A   P   S   P   T   A   P   E   Q   P   V   D   V   E   V   Q    249
GAG GCA GCC TCA GCC CCT AGC CCA ACA GCT CCA GAG CAA CCA GTG GAC GTT GAG GTC CAG   747

 D   L   E   E   F   A   L   R   P   A   P   Q   G   I   T   I   K   C   R   I    269
GAT CTT GAG GAG TTT GCA CTG AGG CCG GCC CCC CAG GGT ATC ACC ATC AAA TGC CGC ATC   807

 T   R   D   K   K   G   M   D   R   G   M   Y   P   T   Y   F   L   H   L   D    289
ACT CGG GAC AAG AAA GGG ATG GAC CGG GGC ATG TAC CCC ACC TAC TTT CTG CAC CTG GAC   867

 R   E   D   G   K   K   V   F   L   L   A   G   R   K   R   K   K   S   K   T    309
CGT GAG GAT GGG AAG AAG GTG TTC CTC CTG GCG GGA AGG AAG AGA AAG AAG AGT AAA ACT   927

 S   N   Y   L   I   S   V   D   P   T   D   L   S   R   G   G   D   S   Y   I    329
TCC AAT TAC CTC ATC TCT GTG GAC CCA ACA GAC TTG TCT CGA GGA GGG GAC AGC TAT ATC   987

 G   K   L   R   S   N   L   M   G   T   K   F   T   V   Y   D   N   G   V   N    349
GGG AAA CTG CGG TCC AAC TTG ATG GGC ACC AAG TTC ACT GTT TAT GAC AAT GGA GTC AAC  1047

 P   Q   K   A   S   S   S   T   L   E   S   G   T   L   R   Q   E   L   A   A    369
CCT CAG AAG GCC TCA TCC TCC ACT TTG GAA AGT GGA ACC TTA CGT CAG GAG CTG GCA GCT  1107
```

FIG.4B

```
 V   C   Y   E   T   N   V   L   G   F   K   G   P   R   K   M   S   V   I   V     389
GTG TGC TAC GAG ACA AAC GTC TTA GGC TTC AAG GGG CCT CGG AAG ATG AGC GTG ATT GTC   1167

 P   G   M   N   M   V   H   E   R   V   S   I   R   P   R   N   E   H   E   T     409
CCA GGC ATG AAC ATG GTT CAT GAG AGA GTC TCT ATC CGC CCC CGC AAC GAG CAT GAG ACA   1227

 L   L   A   R   W   Q   N   K   N   T   E   S   I   I   E   L   Q   N   K   T     429
CTG CTA GCA CGC TGG CAG AAT AAG AAC ACG GAG AGT ATC ATC GAG CTG CAA AAC AAG ACA   1287

 P   V   W   N   D   D   T   Q   S   Y   V   L   N   F   H   G   R   V   T   Q     449
CCT GTC TGG AAT GAT GAC ACA CAG TCC TAT GTA CTC AAC TTC CAT GGG CGC GTC ACA CAG   1347

 A   S   V   K   N   F   Q   I   I   H   G   N   D   P   D   Y   I   V   M   Q     469
GCC TCC GTG AAG AAC TTC CAG ATC ATC CAT GGC AAT GAC CCG GAC TAC ATC GTG ATG CAG   1407

 F   G   R   V   A   E   D   V   F   T   M   D   Y   N   Y   P   L   C   A   L     489
TTT GGC CGG GTA GCA GAG GAT GTG TTC ACC ATG GAT TAC AAC TAC CCG CTG TGT GCA CTG   1467

 Q   A   F   A   I   A   L   S   S   F   D   S   K   L   A   C   E   *             506
CAG GCC TTT GCC ATT GCC CTG TCC AGC TTC GAC AGC AAG CTG GCG TGC GAG TAG AGGCCTC   1528

TTCGTGCCCTTTGGGGTTGCCCAGCCTGGAGCGGAGCTTGCCTGCCTGCCTGTGGAGACAGCCCTGCCTATCCTCTGTA   1607

TATAGGCCTTCCGCCAGATGAAGCTTTGGCCCTCAGTGGGCTCCCTGGCCCAGCCAGCCAGGAACTGGCTCCTTTGGCT   1686

CTGCTACTGAGGCAGGGGAGTAGTGGAGAGCGGGTGGGTGGGTGTTGAAGGGATTGAGAATTAATTCTTTCCATGCCAC   1765

GAGGATCAACACACACTCCCACCCTTGGGTAGTAAGTGGTTGTTGTNAGTCGGTACTTTACCAAAGCTTGAGCAACCTC   1844

TTCCAAGCTTGGGAAAGGGCCGCAAAAAGGCATTAGGAGGGGAG                                      1888
```

RP COMPOSITIONS AND DIAGNOSTIC USES THEREFOR

RELATED APPLICATIONS

This application is a divisional application of Ser. No. 08/847,040 filed on May 1, 1997, now pending, which in turn is a continuation-in-part application of Ser. No. 08/697,766 filed on Aug. 29, 1996, which is a continuation-in-part application of Ser. No. 08/631,200 filed on Apr. 12, 1996, now U.S. Pat. No. 5,646,040. The contents of all of the aforementioned application(s) are hereby incorporated by reference.

BACKGROUND OF THE INVENTION

Retinitis pigmentosa (alternatively referred to herein using its full name or the abbreviation "RP") is a group of human hereditary retinal degenerations which are named for the characteristic intraretinal pigment which appears around the mid-peripheral retina of individuals with RP (Berson, E. L. (1996) *PNAS* 93:4526–4528). Individuals with RP suffer from degeneration of photoreceptor cells which in turn leads to various clinical features which are common among these individuals. For example, RP results in night blindness, gradual loss of peripheral visual field, and eventual loss of central vision. In typical cases, rod photoreceptors are more severely affected early in the disease, hence the early symptom of night blindness. Later in the disease, cone photoreceptors degenerate. Most cases of RP have no extraocular abnormalities. In a minority of families, however, RP is associated with other disease manifestations such as hearing loss in Usher syndrome, polydactyly, obesity, hypogonadism, mental retardation in Bardet-Biedl syndrome, and cardiac conduction defects in Keams-Sayre syndrome. Dryja, T. P. and Li, T. (1995) *Human Mol. Genet*. 4:1739–1743.

RP can be inherited by an autosomal dominant, autosomal recessive, X-linked, or digenic mode (Kajiwara, K. et al. (1994) *Science* 264:1604–1608). Substantial genetic heterogeneity has been observed in this condition, with over 20 loci mapped (Dryja, T. P. and Li, T. (1995) *Human Mol. Genet*. 4:1739–1743; Daiger, S. P. et al. (1995) *Behav. Brain Sci*. 18:452–467). Mutations have been identified in seven genes which map to seven different chromosomes (Kajiwara, K. et al. (1994) *Science* 264:1604–1608; Dryja, T. B. et al. (1990) *Nature* 343:364–366; Farrar, G. J. et al. (1991) *Nature* 354::478–480; Kajiwara, K. et al. (1991) *Nature* 354:480–483; McLaughlin, M. E. et al. (1993) *Nature Genet*. 4:130–133; Dryja, T. P. et al. (1995) *PNAS* 92:10177–10181; Huang, S. H. et al. (1995) *Nature Genet*. 11:468–471; Bascom, R. A. et al. (1995) *Human Mol. Genet*. 4:1895–1902; Weil, D. et al. (1995) *Nature* 374-60–61). Four of these genes encode proteins in the rod phototransduction cascade-namely rhodopsin (mapped to chromosomes 3q21–q24 (autosomal dominant, autosomal recessive)), the α and β subunits of rod cGMP phosphodiesterase (mapped to chromosomes 5q31.2–q34 (autosomal recessive), and 4p16.3 (autosomal recessive), respectively)), and the rod cGMP cation-gated channel protein α subunit (mapped to chromosome 4p14–q13 (autosomal recessive)) (Berson, E. L. (1996) *PNAS* 93:4526–4528; Dryja, T. P. and Li, T. (1995) *Human Mol. Genet*. 4:1739–1743). Two of these genes, peripherin/RDS (mapped to chromosome 6p11.2–p21.1 (autosomal dominant, autosomal recessive)) and rod outer segment membrane protein 1 (mapped to chromosome 11q13 (digenic)), encode proteins involved in maintaining photoreceptor outer segment disc structure (Berson, E. L. (1996) *PNAS* 93:4526–4528; Dryja, T. P. and Li, T. (1995) *Human Mol. Genet*. 4:1739–1743). Mutations in the gene encoding myosin VIIa (mapped to chromosome 11q13.5 (autosomal recessive)) have been found in a form of RP with associated profound congenital deafness (Usher syndrome) (Berson, E. L. (1996) *PNAS* 93:4526–4528; Dryja, T. P. and Li, T. (1995) *Human Mol. Genet*. 4:1739–1743).

An additional locus for autosomal recessive RP has been mapped on chromosome 6p by linkage analysis (Knowles, J. A., et. al., (1994) *Hum. Mol. Genet*. 3:1401–1403). This locus is approximately 20 centimorgans telomeric from the previously described peripherin/RDS gene, and thus represents a novel disease locus.

SUMMARY OF THE INVENTION

This invention is based on the discovery of a novel gene which, as described herein, was mapped very close (2.8 cR which is about 1 Mb) to the marker D6S291 on chromosome 6. The D6S291 marker is the most tightly-linked marker to the retinitis pigmentosa locus 14 (RP14) on chromosome 6 (Knowles et al. (1994) *Hum. Mol. Genet*. 3:1401–1403). Thus, this gene was designated the retinitis pigmentosa ("rp") gene. The rp gene encodes a polypeptide, referred to herein as an rp polypeptide. The rp polypeptide is involved in signal transduction pathways which regulate sensory functions, e.g., vision and/or hearing functions. In a preferred embodiment, the rp polypeptides are involved in signal transduction pathways which regulate the function of cells of the eye, e.g., cells of the retina, e.g., neural cells of the retina, e.g., the rod and cone photoreceptor cells of the retina.

The rp gene and polypeptide were also found to share sequence similarity with the human TUB gene and the TUB gene product, respectively. Mutations in the mouse homologue of the human TUB gene are characterized by progressive sensory deterioration such as progressive retinal and cochlear degeneration (Heckenlively, J. R. et al. (1995) *PNAS* 92:11100–11104; Ohlemiller, K. K. et al. (1995) *NeuroReport* 6:845–849), maturity-onset obesity with insulin resistance, and impaired glucose tolerance (Coleman, D. L. and Eicher, E. M. (1990) *J. Hered*. 81:424–427). It has also been found that rp polypeptides of the invention interact with (e.g., bind to) at least one protein which is a member of the human TUB interactor ("hTI") family of proteins. Specifically, the rp polypeptides have been found to interact with hTI-2, a TUB interactor described in U.S. Ser. No. 08/715,032, filed Sep. 17, 1996, the contents of which are incorporated herein by reference. Thus, by their similarity to the TUB gene product and their ability to interact with at least one TUB interactor protein, the rp polypeptides of the invention are also involved in signal transduction pathways which regulate body weight and pathways involved in metabolism, e.g., glucose metabolism.

Accordingly, one aspect of the invention pertains to an isolated rp nucleic acid molecule (e.g., genomic DNAs, cDNAs, RNAs) comprising a nucleotide sequence encoding an rp polypeptide or a bioactive fragment thereof, as well as nucleic acid fragments suitable as primers or hybridization probes for the detection of rp-encoding nucleic acid (e.g., mRNA). In one embodiment, the rp polypeptide or bioactive fragment encoded by the nucleic acid molecule is a vertebrate, e.g., mammalian, polypeptide or bioactive fragment thereof. In particularly preferred embodiments, the isolated nucleic acid molecule comprises the nucleotide sequence of SEQ ID NO:1, the nucleotide sequence of the DNA insert of the plasmid deposited with ATCC as Accession Number 98144, the nucleotide sequence of the DNA insert of the plasmid deposited with ATCC as Accession Number 98147, or the coding region or a complement of one of these nucleotide sequences. In other particularly preferred embodiments, the isolated nucleic acid molecule of the invention comprises a nucleotide sequence which hybridizes to or is at least about 60–65%, preferably at least about 70–75%, more preferably at least about 80–85%, and even more preferably at least about 90–95% or more homologous to the nucleotide sequence shown in SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147 or a portion of one of these nucleotide sequences. In other preferred embodiments, the isolated nucleic acid molecule encodes an amino acid sequence which is at least about 50–60%, preferably at least about 65–70%, more preferably at least about 75–80%, and even more preferably at least about 85, 90, 95% or more homologous to the amino acid sequence encoded by the nucleotide sequence shown in SEQ ID NO:1, the amino acid sequence encoded by the nucleotide sequence of the DNA insert of the plasmid deposited with ATCC as Accession Number 98144, or the amino acid sequence encoded by the nucleotide sequence of the DNA insert of the plasmid deposited with ATCC as Accession Number 98147 or a portion of an amino acid sequence encoded by a portion of one of these nucleotide sequences. In particularly preferred embodiments, the isolated nucleic acid molecule encodes the amino acid sequence of SEQ ID NO:2, the amino acid sequence encoded by the nucleotide sequence of the DNA insert of the plasmid deposited with ATCC as Accession Number 98144, or the amino acid sequence encoded by the nucleotide sequence of the DNA insert of the plasmid deposited with ATCC as Accession Number 98147. The preferred rp polypeptides of the present invention also preferably possess at least one rp bioactivity described herein.

Preferably, the polypeptide or a bioactive fragment thereof encoded by the nucleic acid molecule maintains the ability to modulate or regulate a sensory function and/or body weight. In one embodiment, the polypeptide or bioactive fragment encoded by the nucleic acid molecule is at least about 50–60%, preferably at least about 65–70%, more preferably at least about 75–80%, and even more preferably at least about 85, 90, 95% or more homologous to the amino acid sequence encoded by the nucleotide sequence shown in SEQ ID NO:1, the amino acid sequence encoded by the nucleotide sequence of the DNA insert of the plasmid deposited with ATCC as Accession Number 98144, or the amino acid sequence encoded by the nucleotide sequence of the DNA insert of the plasmid deposited with ATCC as Accession Number 98147 or a portion of an amino acid sequence encoded by a portion of one of these nucleotide sequences.

In yet another embodiment, the isolated nucleic acid molecule is derived from a human and encodes a portion of a protein which includes a selected domain or motif, e.g., the C-terminal portion, e.g., the C-terminal half of the protein or a portion thereof including the C-terminal most cysteine residue, a nuclear localization site, a tyrosine phosphorylation site, e.g., a tyrosine phosphorylation site capable of binding to an SH2-containing protein, and has one or more of the following bioactivities: 1) it can interact with (e.g., bind to) a TUB interactor protein, e.g., hTI-2; 2) it can modulate the activity of a TUB interactor protein, e.g., hTI-2; and 3) it can modulate or regulate a sensory function, e.g., a sensory function in retinal cells, body weight, and/or a metabolic function.

In another embodiment, the isolated nucleic acid molecule is at least 15 nucleotides in length and hybridizes under stringent conditions to a nucleic acid molecule comprising the nucleotide sequence of SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147. Preferably, the isolated nucleic acid molecule corresponds to a naturally-occurring nucleic acid molecule. More preferably, the isolated nucleic acid molecule encodes naturally-occurring human rp or a bioactive fragment thereof. Moreover, given the disclosure herein of an rp-encoding cDNA sequence (e.g., SEQ ID NO:1), antisense nucleic acid molecules (i.e., molecules which are complementary to the coding strand of the rp cDNA sequence) are also provided by the invention.

Another aspect of the invention pertains to vectors, e.g., recombinant expression vectors, containing the nucleic acid molecules of the invention and host cells into which such vectors have been introduced. In one embodiment, such a host cell is used to produce an rp polypeptide by culturing the host cell in an appropriate medium. If desired, the rp polypeptide can be then isolated from the medium or the host cell.

Yet another aspect of the invention pertains to transgenic nonhuman animals in which an rp gene has been introduced or altered. In one embodiment, the genome of the nonhuman animal has been altered by introduction of a nucleic acid molecule of the invention encoding rp as a transgene. In another embodiment, an endogenous rp gene within the genome of the nonhuman animal has been altered, e.g., functionally disrupted, by homologous recombination. The transgenic and homologous recombinant nonhuman animals can be used, for example, as animal models for identifying compounds which are capable of being used as therapeutic agents to treat disorders characterized by aberrant or abnormal rp nucleic acid expression or rp polypeptide activity.

Still another aspect of the invention pertains to an isolated rp polypeptide, a fragment, or portion, e.g., a bioactive fragment or portion, thereof. In a preferred embodiment, the isolated rp polypeptide or bioactive fragment thereof can modulate a sensory function (e.g., vision and/or hearing) and/or body weight. In another preferred embodiment, the isolated rp polypeptide or bioactive fragment thereof is sufficiently homologous to an amino acid sequence of SEQ ID NO:2 such that the polypeptide or bioactive fragment thereof maintains the ability to modulate a sensory function (e.g., vision and/or hearing) and/or body weight.

In one embodiment, the bioactive fragment of the rp polypeptide includes a domain or motif, preferably a domain or motif which has an rp bioactivity. The domain can comprise the C-terminal portion, e.g., the C-terminal half of the rp polypeptide or a portion thereof including the C-terminal most cysteine residue, a nuclear localization site, a tyrosine phosphorylation site, e.g., a tyrosine phosphorylation site capable of binding to an SH2-containing protein, of the amino acid sequence of SEQ ID NO:2, the amino acid sequence encoded by the nucleotide sequence of the DNA insert of the plasmid deposited with ATCC as Accession Number 98144, or the amino acid sequence encoded by the nucleotide sequence of the DNA insert of the plasmid deposited with ATCC as Accession Number 98147.

Preferably, the bioactive fragment of the rp polypeptide which includes a domain which also has one of the following bioactivities: 1) it can interact with (e.g., bind to) a TUB interactor protein, e.g., hTI-2; 2) it can modulate the activity of a TUB interactor protein, e.g., hTI-2; and 3) it can modulate or regulate a sensory function, e.g., a sensory function in retinal cells, body weight, and/or a metabolic function.

The invention also provides an isolated preparation of an rp polypeptide. In preferred embodiments, the rp polypeptide comprises the amino acid sequence of SEQ ID NO:2, an amino acid sequence encoded by the nucleotide sequence of the DNA insert of the plasmid deposited with ATCC as Accession Number 98144, or an amino acid sequence encoded by the nucleotide sequence of the DNA insert of the plasmid deposited with ATCC as Accession Number 98147. In yet another embodiment, the polypeptide is at least about 50–60%, preferably at least about 65–70%, more preferably at least about 75–80%, and even more preferably at least about 85, 90, 95% or more homologous to the entire amino acid sequence of SEQ ID NO:2, an amino acid sequence encoded by the nucleotide sequence of the DNA insert of the plasmid deposited with ATCC as Accession Number 98144, or an amino acid sequence encoded by the nucleotide sequence of the DNA insert of the plasmid deposited with ATCC as Accession Number 98147. In other embodiments, the isolated rp polypeptide comprises an amino acid sequence which is at least about 60–70% or more homologous to the amino acid sequence of SEQ ID NO:2 and has an one or more of the following activities: 1) it can interact with (e.g., bind to) a TUB interactor protein, e.g., hTI-2; 2) it can modulate the activity of a TUB interactor protein, e.g., hTI-2; and 3) it can modulate or regulate a sensory function, e.g., a sensory function in retinal cells, body weight and/or a metabolic function. Alternatively, the isolated rp polypeptide can comprise an amino acid sequence which is encoded by a nucleotide sequence which hybridizes, e.g., hybridizes under stringent conditions, or is at least about 60–65%, preferably at least about 70–75%, more preferably at least about 80–85%, and even more preferably at least about 90–95% or more homologous to the nucleotide sequence of SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147. It is also preferred that these preferred forms of rp have one or more of the rp activities described herein.

The rp polypeptide or a bioactive fragment thereof can be operatively linked to a non-rp polypeptide to form a fusion protein. In addition, the rp polypeptide or a bioactive fragment thereof can be incorporated into a pharmaceutical composition comprising the protein and a pharmaceutically acceptable carrier.

The rp polypeptides of the invention, or fragments or portions thereof, can be used to prepare anti-rp antibodies. Accordingly, the invention also provides an antigenic peptide of rp which comprises at least 8 amino acid residues of the amino acid sequence shown in SEQ ID NO:2 and encompasses an epitope of rp such that an antibody raised against the peptide forms a specific immune complex with rp. Preferably, the antigenic peptide comprises at least 10 amino acid residues, more preferably at least 15 amino acid residues, even more preferably at least 20 amino acid residues, and most preferably at least 30 amino acid residues. The invention further provides an antibody which is specifically reactive with an epitope of rp. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

Another aspect of the invention pertains to methods for treating subjects having various disorders. For example, the invention pertains to methods for treating a subject having a disorder characterized by aberrant or abnormal rp polypeptide activity or rp nucleic acid expression such as a sensory disorder, e.g., a disorder which affects vision and/or hearing, e.g., a vision (eye) disorder such as a retinal disorder, e.g., retinitis pigmentosa, a disorder associated with body weight, e.g., obesity, cachexia, and anorexia, or a metabolic disorder, e.g., a disorder associated with insulin resistance, e.g., diabetes. These methods include administering to the subject an rp modulator (e.g., a small molecule) such that treatment of the subject occurs.

In another embodiment, the invention pertains to methods for treating a subject having retinitis pigmentosa or a disorder associated with body weight comprising administering to the subject an rp modulator such that treatment occurs.

In other embodiments, the invention pertains to methods for treating a subject having retinitis pigmentosa or a disorder associated with body weight comprising administering to the subject an rp polypeptide or a bioactive fragment thereof such that treatment occurs. Retinitis pigmentosa and disorders associated with body weight can also be treated according to the invention by administering to the subject having the disorder a nucleic acid encoding an rp polypeptide or a bioactive fragment thereof such that treatment occurs.

Still another aspect of the invention pertains to methods, e.g., screening assays, for identifying a compound or agent for treating a disorder characterized by aberrant or abnormal rp nucleic acid expression or rp polypeptide activity, e.g., retinitis pigmentosa, a disorder associated with body weight. These methods typically include assaying the ability of the compound or agent to modulate the expression of the rp gene or the activity of the rp polypeptide thereby identifying a compound or agent for treating a disorder characterized by aberrant rp nucleic acid expression or rp polypeptide activity. In a preferred embodiment, the method involves contacting a biological sample, e.g., a cell or tissue sample, e.g., a retinal cell sample, a blood cell sample, e.g., a lymphocyte cell sample, obtained from a subject having the disorder with the compound or agent, determining the amount of rp nucleic acid expressed and/or measuring the activity of the rp polypeptide in the biological sample, comparing the amount of rp nucleic acid expressed in the biological sample and/or the measurable rp biological activity in the cell to that of a control sample. An alteration in the amount of rp nucleic acid expression or rp polypeptide activity in the cell exposed to the compound or agent in comparison to the control is indicative of a modulation of rp nucleic acid expression and/or rp polypeptide activity.

The invention also pertains to methods for modulating a cell associated activity, e.g., proliferation or differentiation. Such methods include contacting the cell with an rp modulator such that a cell associated activity is altered relative to a cell associated activity (e.g., the same cell associated activity) of the cell in the absence of the agent. In a preferred embodiment, the cell is involved in regulating a sensory function, body weight, and/or a metabolic function. The rp modulator can stimulate rp polypeptide activity or rp nucleic acid expression. Examples such stimulatory rp modulators include small molecules, active rp polypeptides, and nucleic acids encoding rp that have been introduced into the cell. Alternatively, the rp modulator can inhibit rp polypeptide activity or rp nucleic acid expression. Examples of such inhibitory rp modulators include small molecules, antisense rp nucleic acid molecules, and antibodies that specifically react with an epitope of rp. In a preferred embodiment, the cell is present within a subject and the agent is administered to the subject The present invention also pertains to methods for detecting genetic lesions in an rp gene, thereby determining if a subject with the lesioned gene is at risk for (or is predisposed to have) a disorder characterized by aberrant or abnormal rp nucleic acid expression or rp polypeptide activity, e.g., a sensory disorder or a disorder associated with body weight. In preferred embodiments, the methods include detecting, in a sample of cells, e.g., blood cells, e.g., lymphocytes, from the subject, the presence or absence of a genetic lesion characterized by an alteration affecting the integrity of a gene encoding an rp polypeptide or the misexpression of the rp gene.

The invention also pertains to methods for identifying a compound or agent which interacts with (e.g., binds to) an rp polypeptide. These methods can include the steps of contacting the rp polypeptide with the compound or agent under conditions which allow binding of the compound to the rp polypeptide to form a complex and detecting the formation of a complex of the rp polypeptide and the compound in which the ability of the compound to bind to the rp polypeptide is indicated by the presence of the compound in the complex.

The invention further pertains to methods for identifying a compound or agent which modulates, e.g., stimulates or inhibits, the interaction of the rp polypeptide with a target molecule, e.g., a TUB interactor, e.g., hTI-2. In these methods, the rp polypeptide is contacted, in the presence of the compound or agent, with the target molecule under conditions which allow binding of the target molecule to the rp polypeptide to form a complex. An alteration, e.g., an increase or decrease, in complex formation between the rp polypeptide and the target molecule as compared to the amount of complex formed in the absence of the compound or agent is indicative of the ability of the compound or agent to modulate the interaction of the rp polypeptide with a target molecule.

Another aspect of the invention pertains to methods for detecting the presence of rp in a biological sample. In a preferred embodiment, the methods involve contacting a biological sample (e.g., a retinal cell sample) with a compound or an agent capable of detecting rp polypeptide or rp mRNA such that the presence of rp is detected in the biological sample. The compound or agent can be, for example, a labeled or labelable nucleic acid probe capable of hybridizing to rp mRNA or a labeled or labelable antibody capable of binding to rp polypeptide. The invention further provides methods for diagnosis of a subject with, for example, a sensory disorder, e.g., retinitis pigmentosa, a disorder associated with body weight, a disorder associated with insulin resistance, e.g., diabetes, based on detection of rp polypeptide or mRNA. In one embodiment, the method involves contacting a cell or tissue sample (e.g., a retinal cell sample) from the subject with an agent capable of detecting rp polypeptide or mRNA, determining the amount of rp polypeptide or mRNA expressed in the cell or tissue sample, comparing the amount of rp polypeptide or mRNA expressed in the cell or tissue sample to a control sample and forming a diagnosis based on the amount of rp polypeptide or mRNA expressed in the cell or tissue sample as compared to the control sample. Preferably, the cell sample is a retinal cell sample. Kits for detecting rp in a biological sample are also within the scope of the invention.

BRIEF DESCRIPTION OF THE DRAWINGS

FIG. 1 depicts the nucleotide (SEQ ID NO:1) and deduced amino acid (SEQ ID NO:2) sequence of the human rp gene including 5' and 3' untranslated regions. The coding region alone of the human rp gene is shown in SEQ ID NO:3.

FIG. 2 depicts the nucleotide (SEQ ID NO:4) and deduced amino acid (SEQ ID NO:5) sequence of a human rp gene fragment including a 3' untranslated region.

FIG. 3 depicts the nucleotide (SEQ ID NO:6) and deduced amino acid (SEQ ID NO:7) sequence of the mouse tub gene including 5' and 3' untranslated regions. The coding region alone of the mouse tub gene is shown in SEQ ID NO:8.

FIG. 4 depicts the nucleotide (SEQ ID NO:9) and deduced amino acid (SEQ ID NO:10) sequence of the human TUB gene including 5' and 3' untranslated regions. The coding region alone of the human TUB gene is shown in SEQ ID NO:11.

DETAILED DESCRIPTION OF THE INVENTION

The present invention is based on the discovery of novel molecules, referred to herein as rp nucleic acid and polypeptide molecules, which play a role in or function in sensory functions, functions associated with body weight, and/or metabolic functions. As described above, the rp gene was mapped very close to the most tightly linked marker (D6S291) to the retinitis pigmentosa locus 14 on chromosome 6. The rp polypeptides encoded by the rp gene are involved in signal transduction pathways which regulate sensory functions, e.g., vision and/or hearing functions. In a preferred embodiment, the rp polypeptides are involved in signal transduction pathways which regulate the function of cells of the eye, e.g., cells of the retina, e.g., neural cells of the retina, e.g., the rod and cone photoreceptor cells of the retina, and cells of the ear, e.g., audioreceptor cells. Thus, rp molecules (or modulators thereof) of the present invention can be used to treat various sensory disorders, e.g., vision disorders such as retinitis pigmentosa, and hearing disorders such as Usher syndrome.

Moreover, as described above, the rp gene and polypeptide were also found to share sequence similarity with the human TUB gene and the TUB gene product, respectively. In particular, the human rp gene is 56.4% identical to the human TUB gene while the rp protein is 46% identical to the human TUB protein. Although the N-terminus of the two gene products are dissimilar, the most conserved region of the two gene products are 66.4% identical. Thus, as the rp gene and polypeptide were found to share sequence similarity with the human TUB gene and the TUB gene product, respectively and the rp polypeptide was found to interact with at least one protein which is a member of the human TUB interactor ("hTI") family of proteins, the rp polypeptides are involved in signal transduction pathways which regulate body weight and pathways involved in metabolism, e.g., glucose metabolism. Specifically, the rp polypeptides have been found to interact with hTI-2, a TUB interactor described in U.S. Ser. No. 08/715,032, filed Sep. 17, 1996, the contents of which are expressly incorporated herein by reference. hTI-2 is expressed in most human tissues with the highest expression occurring in testis, pancreas, liver, uterus, and brain. Thus, rp molecules (or modulators thereof) of the present invention can be used to treat various body weight disorders, e.g., obesity, cachexia, anorexia, and metabolic disorders such as diabetes.

The human rp nucleotide sequence (identified as described in Example 1) and the predicted amino acid sequence of the human rp protein are shown in FIG. 1 and in SEQ ID NOs:1 and 2, respectively. A plasmid containing the full length nucleotide sequence encoding human rp protein (with the DNA insert name of fyhx77102) was deposited with the American Type Culture Collection (ATCC), Rockville, Md., on Aug. 23, 1996 and assigned Accession Number 98147. A plasmid containing the nucleotide sequence encoding a portion of the human rp protein (with the DNA insert name of foxtub B1) was deposited with ATCC, Rockville, Md., on Aug. 22, 1996 and assigned Accession Number 98144. These deposits will be maintained under the terms of the Budapest Treaty on the International Recognition of the Deposit of Microorganisms for the Purposes of Patent Procedure. These deposits were made merely as a convenience for those of skill in the art and do not constitute admissions that a deposit is required under 35 U.S.C. §112.

The human rp gene, which is approximately 2184 nucleotides in length (the coding region is approximately 1050 nucleotides in length), encodes a full length protein which is approximately 349 amino acid residues in length. The rp protein is predominantly expressed retinal tissue. The rp protein contains a C-terminal cysteine (amino acid residue 348) which is a putative palmytylation or prenylation site for targeting the protein to the cell membrane. Amino acid residues 147–153 of the rp protein comprise a putative nuclear localization sequence. The rp protein also includes at least two dibasic proteolytic cleavage sites at amino acid residues 24–25 and at amino acid residues 147–150. In addition, the rp protein includes several putative tyrosine phosphorylation sites which represent putative SH2 binding sites. These putatative tyrosine phosphorylation sites include the following: amino acid residue 128 (GMYPSYFL), amino acid residue 131 (PSYFLHLD), amino acid residue 157 (ANYLISID), amino acid residue 199 (RGYSTNV), amino acid residue 215 (VIYETNVL), amino acid residue 282 (QSYTLNFH), amino acid residue 308 (PDYIVL), amino acid residue 325 (LDYNYPLC), and amino acid residue 327 (YNYPLCAL).

The rp protein or a bioactive fragment or portion thereof of the invention can have one or more of the following activities: 1) it can interact with (e.g., bind to) a TUB interactor protein, e.g., hTI-2; 2) it can modulate the activity of a TUB interactor protein, e.g., hTI-2; and 3) it can modulate or regulate a sensory function, e.g., a sensory function in retinal cells, body weight, e.g., obesity, cachexia, anorexia, and/or a metabolic function, e.g., diabetes.

Various aspects of the invention are described in further detail in the following subsections:

I. Isolated Nucleic Acid Molecules

One aspect of the invention pertains to isolated nucleic acid molecules that encode rp or bioactive fragments or portions thereof, as well as nucleic acid fragments sufficient for use as hybridization probes to identify rp-encoding nucleic acid (e.g., rp mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated rp nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a retinal cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1, or a portion thereof, can be isolated using standard molecular biology techniques and the sequence information provided herein. For example, a human rp cDNA can be isolated from a human retinal library using all or portion of SEQ ID NO:1 as a hybridization probe and standard hybridization techniques (e.g., as described in Sambrook, J., Fritsh, E. F., and Maniatis, *T. Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NO:1 can be isolated by the polymerase chain reaction using oligonucleotide primers designed based upon the sequence of SEQ ID NO:1. For example, mRNA can be isolated from normal retinal cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an rp nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147. The sequence of SEQ ID NO:1 corresponds to the human rp cDNA. This cDNA comprises sequences encoding the rp protein (i.e., "the coding region", from nucleotides 569 to 1615), as well as 5' untranslated sequences (nucleotides 1 to 568) and 3' untranslated sequences (nucleotides 1616 to 2184). Alternatively, the nucleic acid molecule can comprise only the coding region of SEQ ID NO:1 (e.g., nucleotides 569 to 1615).

In another preferred embodiment, an isolated nucleic acid molecule of the invention comprises a nucleic acid molecule which is a complement of the nucleotide sequence shown in SEQ ID NO:1, the nucleotide sequence of the DNA insert of the plasmid deposited with ATCC as Accession Number 98144, the nucleotide sequence of the DNA insert of the plasmid deposited with ATCC as Accession Number 98147, or a portion of one of these nucleotide sequences. A nucleic acid molecule which is complementary to the nucleotide sequence shown in SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147 is one which is sufficiently complementary to the nucleotide sequence shown in SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147 such that it can hybridize to the nucleotide sequence shown in SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147, thereby forming a stable duplex.

In still another preferred embodiment, an isolated nucleic acid molecule of the invention comprises a nucleotide sequence which is at least about 60–65%, preferably at least about 70–75%, more preferably at least about 80–85%, and even more preferably at least about 90–95% or more homologous to the nucleotide sequence shown in SEQ ID NO:1, the nucleotide sequence of the DNA insert of the plasmid deposited with ATCC as Accession Number 98144, the nucleotide sequence of the DNA insert of the plasmid deposited with ATCC as Accession Number 98147, or a portion of one of these nucleotide sequences. In an additional preferred embodiment, an isolated nucleic acid molecule of the invention comprises a nucleotide sequence which hybridizes, e.g., hybridizes under stringent conditions, to the nucleotide sequence shown in SEQ ID NO:1, the nucleotide sequence of the DNA insert of the plasmid deposited with ATCC as Accession Number 98144, the nucleotide sequence of the DNA insert of the plasmid deposited with ATCC as Accession Number 98147, or a portion of one of these nucleotide sequences.

Moreover, the nucleic acid molecule of the invention can comprise only a portion of the coding region of SEQ ID NO:1, for example a fragment which can be used as a probe or primer or a fragment encoding a bioactive fragment of rp. The nucleotide sequence of the rp gene provided herein allows for the generation of probes and primers designed for use in identifying and/or cloning rp homologues in other cell types, e.g., from other tissues, as well as rp homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO:1 sense, an antisense sequence of SEQ ID NO:1, or naturally occurring mutants thereof. Primers based on the nucleotide sequence in SEQ ID NO:1 can be used in PCR reactions to clone rp homologues. Probes based on the rp nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an rp polypeptide, such as by measuring a level of an rp-encoding nucleic acid in a sample of cells from a subject e.g., detecting rp mRNA levels or determining whether a genomic rp gene has been mutated or deleted.

In one embodiment, the nucleic acid molecule of the invention encodes a polypeptide or bioactive fragment thereof which includes an amino acid sequence which is sufficiently homologous to an amino acid sequence of SEQ ID NO:2, an amino acid sequence encoded by the nucleotide sequence of the DNA insert of the plasmid deposited with ATCC as Accession Number 98144, or an amino acid sequence encoded by the nucleotide sequence of the DNA insert of the plasmid deposited with ATCC as Accession Number 98147 such that the polypeptide or fragment thereof maintains the ability to modulate a sensory function, a function associated with body weight, and/or a metabolic function. As used herein, the language "sufficiently homologous" refers to polypeptides or fragments thereof which have amino acid sequences which include a minimum number of identical or equivalent (e.g., an amino acid residue which has a similar side chain as an amino acid residue in SEQ ID NO:2) amino acid residues to an amino acid sequence of SEQ ID NO:2, an amino acid sequence encoded by the nucleotide sequence of the DNA insert of the plasmid deposited with ATCC as Accession Number 98144, or an amino acid sequence encoded by the nucleotide sequence of the DNA insert of the plasmid deposited with ATCC as Accession Number 98147 such that the polypeptide or fragment thereof is able to modulate a sensory function, a function associated with body weight, and/or a metabolic function. As used herein, a sensory function is a cellular function or activity which aids the individual containing the cell having the activity or function in perceiving a sensation. For example, the rod and cone photoreceptors of the retina aid the individual containing the cells in perceiving light. A function associated with body weight is a cellular function or activity which aids the individual containing the cell having the activity or function in regulating body weight. A metabolic function is a cellular activity or function which aids the individual containing the cell having the activity or function in utilizing energy, e.g., energy provided by proteins, carbohydrates, and/or lipids. In another embodiment, the polypeptide is at least about 50–60%, preferably at least about 65–70%, more preferably at least about 75–80%, and even more preferably at least about 85, 90, 95% or more homologous to the entire amino acid sequence of SEQ ID NO:2, the amino acid sequence encoded by the nucleotide sequence of the DNA insert of the plasmid deposited with ATCC as Accession Number 98144, or the amino acid sequence encoded by the nucleotide sequence of the DNA insert of the plasmid deposited with ATCC as Accession Number 98147.

Portions of polypeptides encoded by the rp nucleic acid molecule of the invention are preferably bioactive fragments or portions of the rp polypeptide. As used herein, the term "bioactive fragment or portion of rp" is intended to include a portion, e.g., a domain/motif, of rp that has one or more of the following activities: 1) it can interact with (e.g., bind to) a TUB interactor protein, e.g., hTI-2; 2) it can modulate the activity of a TUB interactor protein, e.g., hTI-2; and 3) it can modulate or regulate a sensory function, e.g., a sensory function in retinal cells, body weight, and/or a metabolic function.

Standard binding assays, e.g., immunoprecipitations and yeast two-hybrid assays as described herein, can be performed to determine the ability of an rp polypeptide or a bioactive fragment or portion thereof to interact with (e.g., bind to) an TUB interactor protein.

Modulation or regulation of an activity of a TUB interactor protein can be measured in vitro by using standard assays in isolated membrane fractions from cell lines overexpressing sense or antisense constructs encoding the rp polypeptide or bioactive fragment thereof and which also express a TUB interactor protein. Modulation of the TUB interactor protein activity can then be determined by measuring changes in secondary messenger levels, e.g., cGMP levels, in the cells that express both the rp polypeptide and the TUB interactor protein compared to cells which only express the TUB interactor protein.

Modulation or regulation of a sensory function by an rp polypeptide or a bioactive fragment thereof can be measured in vitro as well as in vivo. In one embodiment, modulation of a sensory function can be measured in vitro by using standard assays in isolated membrane fractions from cell lines overexpressing sense or antisense constructs encoding the rp polypeptide or bioactive fragment thereof. For example, a cell line such as COS-1 can be stably transfected with a construct that overexpresses the rp polypeptide. Membrane fractions isolated from these cells can then be mixed with a membrane fraction derived from a preparation of rod photoreceptor outer fragments. cGMP levels can then be measured to determine whether the rp polypeptide or fragment thereof modulates cGMP production, a requirement in light signal transduction. Alternatively, a cell line such as the human fibroblast cell line 293 which has been stably transfected with guanyl cyclase can be used directly to determine modulation of cGMP production. Following overexpression of sense or antisense constructs encoding an rp polypeptide or fragment thereof in such a cell line, cGMP levels can be measured using standard assays. In another embodiment, modulation or regulation of a sensory function by an rp polypeptide or a bioactive fragment thereof can be tested in vivo by constructing transgenic mice overexpressing or lacking expression of the rp polypeptide or fragment thereof. Direct measurement of retinal activity in the mice can then be performed using standard electroretinograms. Alternatively, flux of secondary messengers in the light transduction pathway, e.g., cGMP and $Ca^{++}$ can be measured directly in photoreceptor cells using standard patch clamp techniques.

Modulation or regulation of body weight by an rp polypeptide or a bioactive fragment thereof can be tested in animal models of, for example, obesity. For example, transgenic animals are available which have obese phenotypes. An rp polypeptide or a bioactive fragment thereof or a nucleic acid encoding an rp polypeptide or a bioactive fragment thereof can be administered to such animals and changes in the obese phenotype measured.

In one embodiment, the biologically active portion of rp comprises a selected domain or motif, e.g., the C-terminal portion, e.g., the C-terminal half of the rp polypeptide or a portion thereof including the C-terminal most cysteine residue, a nuclear localization site, a tyrosine phosphorylation site, e.g., a tyrosine phosphorylation site capable of binding to an SH2-containing protein, and has one or more of the following bioactivities: 1) it can interact with (e.g., bind to) a TUB interactor protein, e.g., hTI-2; 2) it can modulate the activity of a TUB interactor protein, e.g., hTI-2; and 3) it can modulate or regulate a sensory function, e.g., a sensory function in retinal cells, body weight, and/or a metabolic function. Additional nucleic acid fragments encoding bioactive fragments or portions of rp can be prepared by isolating a portion of SEQ ID NO:1, expressing the encoded portion (i.e., peptide) of the rp polypeptide (e.g., by recombinant expression in vitro) and assessing the activity of the encoded portion of rp polypeptide.

The invention further encompasses nucleic acid molecules that differ from the nucleotide sequence shown in SEQ ID NO:1 (and portions thereof) due to degeneracy of the genetic code and thus encode the same rp polypeptide as that encoded by the nucleotide sequence shown in SEQ ID NO:1. In another embodiment, an isolated nucleic acid molecule of the invention has a nucleotide sequence encoding a polypeptide having an amino acid sequence shown in SEQ ID NO:2, a polypeptide having an amino acid sequence encoded by the nucleotide sequence of the DNA insert of the plasmid deposited with ATCC as Accession Number 98144, or a polypeptide having an amino acid sequence encoded by the nucleotide sequence of the DNA insert of the plasmid deposited with ATCC as Accession Number 98147.

In addition to the human rp nucleotide sequence shown in SEQ ID NO:1, it will be appreciated by those skilled in the art that DNA sequence polymorphisms that lead to changes in the amino acid sequences of rp may exist within a population (e.g., the human population). Such genetic polymorphism in the rp gene may exist among individuals within a population due to natural allelic variation. As used herein, the terms "gene" and "recombinant gene" refer to nucleic acid molecules comprising an open reading frame encoding an rp polypeptide, preferably a mammalian rp polypeptide. Such natural allelic variations can typically result in 1–5% variance in the nucleotide sequence of the rp gene. Any and all such nucleotide variations and resulting amino acid polymorphisms in rp that are the result of natural allelic variation and that do not alter the functional activity of rp are intended to be within the scope of the invention. Moreover, nucleic acid molecules encoding rp polypeptides from other species, and thus which have a nucleotide sequence which differs from the human sequence of SEQ ID NO:1, are intended to be within the scope of the invention. Nucleic acid molecules corresponding to natural allelic variants and nonhuman homologues of the human rp cDNA of the invention can be isolated based on their homology to the human rp nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, the nucleotide sequence of the DNA insert of the plasmid deposited with ATCC as Accession Number 98144, or the nucleotide sequence of the DNA insert of the plasmid deposited with ATCC as Accession Number 98147. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0. 1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human rp.

In addition to naturally-occurring allelic variants of the rp sequence that may exist in the population, the skilled artisan will further appreciate that changes can be introduced by mutation into the nucleotide sequence of SEQ ID NO:1, thereby leading to changes in the amino acid sequence of the encoded rp polypeptide, without altering the functional ability of the rp polypeptide. For example, nucleotide substitutions leading to amino acid substitutions at "non-essential" amino acid residues can be made in the sequence of SEQ ID NO:1. A "inon-essential" amino acid residue is a residue that can be altered from the wild-type sequence of rp (e.g., the sequence of SEQ ID NO:2) without altering the activity of rp, whereas an "essential" amino acid residue is required for rp activity. For example, conserved amino acid residues in the C-terminal portion of the rp are most likely important for function and are thus essential residues of rp. Other amino acid residues, however, (e.g., those that are not conserved or only semi-conserved) may not be essential for activity and thus are likely to be amenable to alteration without altering rp activity.

Accordingly, another aspect of the invention pertains to nucleic acid molecules encoding rp polypeptides that contain changes in amino acid residues that are not essential for rp activity. Such rp polypeptides differ in amino acid sequence from SEQ ID NO:2 yet retain at least one of the rp activities described herein. In one embodiment, the isolated nucleic acid molecule comprises a nucleotide sequence encoding a polypeptide, wherein the polypeptide comprises an amino acid sequence at least about 50% or more homologous to the amino acid sequence of SEQ ID NO:2 and is capable of modulating a sensory function, a function associated with body weight, and/or a metabolic function. Preferably, the polypeptide encoded by the nucleic acid molecule is at least about 60–65%, preferably at least about 70–75%, more preferably at least about 80–85%, and even more preferably at least about 90–95% or more homologous to the entire amino acid sequence of SEQ ID NO:2, the amino acid sequence encoded by the nucleotide sequence of the DNA insert of the plasmid deposited with ATCC as Accession Number 98144, or the amino acid sequence encoded by the nucleotide sequence of the DNA insert of the plasmid deposited with ATCC as Accession Number 98147.

To determine the percent homology of two amino acid sequences (e.g., SEQ ID NO:2 and a mutant form thereof) or of two nucleic acids (e.g., SEQ ID NO:1 and a mutant form thereof), the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2) is occupied by the same amino acid residue or nucleotide as the corresponding position in the other sequence (e.g., a mutant form of rp), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total# of positions×100).

An isolated nucleic acid molecule encoding an rp polypeptide homologous to the protein of SEQ ID NO:2 can be created by introducing one or more nucleotide substitutions, additions or deletions into the nucleotide sequence of SEQ ID NO:1 such that one or more amino acid substitutions, additions or deletions are introduced into the encoded protein. Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in rp is preferably replaced with another amino acid residue from the same side chain family. Alternatively, in another embodiment, mutations can be introduced randomly along all or part of an rp coding sequence, such as by saturation mutagenesis, and the resultant mutants can be screened for an rp activity described herein to identify mutants that retain rp activity. Following mutagenesis of SEQ ID NO:1, the encoded polypeptide can be expressed recombinantly (e.g., as described in Example 5) and the activity of the protein can be determined using, for example, assays described herein.

In addition to the nucleic acid molecules encoding rp polypeptides described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire rp coding strand, or to only a portion thereof. In one embodiment, an antisense nucleic acid molecule is antisense to a "coding region" of the coding strand of a nucleotide sequence encoding rp. The term "coding region" refers to the region of the nucleotide sequence comprising codons which are translated into amino acid residues (e.g., the entire coding region of SEQ ID NO:1 comprises nucleotides 569 to 1615). In another embodiment, the antisense nucleic acid molecule is antisense to a "noncoding region" of the coding strand of a nucleotide sequence encoding rp. The term "noncoding region" refers to 5' and 3' sequences which flank the coding region that are not translated into amino acids (i.e., also referred to as 5' and 3' untranslated regions).

Given the coding strand sequences encoding rp disclosed herein (e.g., SEQ ID NO:1), antisense nucleic acids of the invention can be designed according to the rules of Watson and Crick base pairing. The antisense nucleic acid molecule can be complementary to the entire coding region of rp mRNA, but more preferably is an oligonucleotide which is antisense to only a portion of the coding or noncoding region of rp mRNA. For example, the antisense oligonucleotide can be complementary to the region surrounding the translation start site of rp mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified micleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an rp polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen, respectively. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an $\alpha$-anomeric nucleic acid molecule. An $\alpha$-anomeric nucleic acid molecule forms specific double-stranded hybrids with complementary RNA in which, contrary to the usual $\beta$-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave rp mRNA transcripts to thereby inhibit translation of rp mRNA. A ribozyme having specificity for an rp-encoding nucleic acid can be designed based upon the nucleotide sequence of an rp cDNA disclosed herein (i.e., SEQ ID NO:1). For example, a derivative of a *Tetrahymena* L-19 IVS RNA can be constructed in which the nucleotide sequence of the active site is complementary to the nucleotide sequence to be cleaved in an rp-encoding mRNA. See, e.g., Cech et al. U.S. Pat. No. 4,987,071 and Cech et al. U.S. Pat. No. 5,116,742. Alternatively, rp mRNA can be used to select a catalytic RNA having a specific ribonuclease activity from a pool of RNA molecules. See, e.g., Bartel, D. and Szostak, J. W. (1993) *Science* 261:1411–1418.

Alternatively, rp gene expression can be inhibited by targeting nucleotide sequences complementary to the regulatory region of the rp (e.g., the rp promoter and/or enhancers) to form triple helical structures that prevent transcription of the rp gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

II. Recombinant Expression Vectors and Host Cells

Another aspect of the invention pertains to vectors, preferably expression vectors, containing a nucleic acid encoding rp (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., rp proteins, mutant forms of rp, fusion proteins, etc.).

The recombinant expression vectors of the invention can be designed for expression of rp in prokaryotic or eukaryotic cells. For example, rp can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the rp is cloned into a pGEX expression vector to create a vector encoding a fusion protein comprising, from the N-terminus to the C-terminus, GST-thrombin cleavage site-rp. The fusion protein can be purified by affinity chromatography using glutathione-agarose resin. Recombinant rp unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the rp expression vector is a yeast expression vector. Examples of vectors for expression in yeast S. cerivisae include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, rp can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740;

Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev*. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to rp mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an rp polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding rp or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an rp polypeptide. Accordingly, the invention further provides methods for producing an rp polypeptide using the host cells of the invention. In one embodiment, the method comprises culturing the host cell of invention (into which a recombinant expression vector encoding rp has been introduced) in a suitable or appropriate medium until an rp polypeptide is produced. In another embodiment, the method further comprises isolating the rp polypeptide from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as sensory disorders, disorders associated with body weight, and/or metabolic disorders. For example, in one embodiment, a host cell of the invention is a fertilized oocyte or an embryonic stem cell into which rp-coding sequences have been introduced. Such host cells can then be used to create non-human transgenic animals in which exogenous rp sequences have been introduced into their genome or homologous recombinant animals in which endogenous rp sequences have been altered. Such animals are useful for studying the function and/or activity of rp and for identifying and/or evaluating modulators of rp activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous rp gene has been altered by homologous recombination between the endogenous gene and an exogenous DNA molecule introduced into a cell of the animal, e.g., an embryonic cell of the animal, prior to development of the animal.

A transgenic animal of the invention can be created by introducing rp-encoding nucleic acid into the male pronuclei of a fertilized oocyte, e.g., by microinjection, retroviral infection, and allowing the oocyte to develop in a pseudopregnant female foster animal. The human rp cDNA sequence of SEQ ID NO:1 can be introduced as a transgene into the genome of a nonhuman animal. Alternatively, a nonhuman homologue of the human rp gene, such as a mouse rp gene, can be isolated based on hybridization to the human rp cDNA (described further in subsection I above) and used as a transgene. Intronic sequences and polyadenylation signals can also be included in the transgene to increase the efficiency of expression of the transgene. A tissue-specific regulatory sequence(s) can be operably linked to the rp transgene to direct expression of rp polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the rp transgene in its genome and/or expression of rp mRNA in tissues or cells of the animals. A transgenic founder animal can then be used to breed additional animals carrying the transgene. Moreover, transgenic animals carrying a transgene encoding rp can further be bred to other transgenic animals carrying other transgenes.

To create a homologous recombinant animal, a vector is prepared which contains at least a portion of an rp gene into which a deletion, addition or substitution has been introduced to thereby alter, e.g., functionally disrupt, the rp gene. The rp gene can be a human gene (e.g., from a human genomic clone isolated from a human genomic library screened with the cDNA of SEQ ID NO:1), but more preferably, is a nonhuman homologue of a human rp gene. For example, a mouse rp gene can be isolated from a mouse genomic DNA library using the human rp cDNA of SEQ ID NO:1 as a probe. The mouse rp gene then can be used to construct a homologous recombination vector suitable for altering an endogenous rp gene in the mouse genome. In a preferred embodiment, the vector is designed such that, upon homologous recombination, the endogenous rp gene is functionally disrupted (i.e., no longer encodes a functional protein; also referred to as a "knock out" vector). Alternatively, the vector can be designed such that, upon homologous recombination, the endogenous rp gene is mutated or otherwise altered but still encodes functional protein (e.g., the upstream regulatory region can be altered to thereby alter the expression of the endogenous rp protein). In the homologous recombination vector, the altered portion of the rp gene is flanked at its 5' and 3' ends by additional nucleic acid of the rp gene to allow for homologous recombination to occur between the exogenous rp gene carried by the vector and an endogenous rp gene in an embryonic stem cell. The additional flanking rp nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced rp gene has homologously recombined with the endogenous rp gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810–813. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal, e.g., the transgenic animal, from which the cell, e.g., the somatic cell, is isolated.

III. Isolated RP Polypeptides and Anti-RP Antibodies

Another aspect of the invention pertains to isolated rp polypeptides, and bioactive fragments or portions thereof, as well as peptide fragments suitable for use as immunogens to raise anti-rp antibodies. An "isolated" or "purified" polypeptide or bioactive fragment or portion thereof is substantially free of cellular material when produced by recombinant DNA techniques, or chemical precursors or other chemicals when chemically synthesized. The language "substantially free of cellular material" includes preparations of rp polypeptide in which the polypeptide is separated from cellular components of the cells in which it is naturally or recombinantly produced. In one embodiment, the language "substantially free of cellular material" includes preparations of rp polypeptide having less than about 30% (by dry weight) of non-rp protein (also referred to herein as a "contaminating protein"), more preferably less than about 20% of non-rp protein, still more preferably less than about 10% of non-rp protein, and most preferably less than about 5% non-rp protein. When the rp polypeptide or bioactive fragment or portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of rp polypeptide in which the polypeptide is separated from chemical precursors or other chemicals which are involved in the synthesis of the polypeptide. In one embodiment, the language "substantially free of chemical precursors or other chemicals" includes preparations of rp polypeptide having less than about 30% (by dry weight) of chemical precursors or non-rp chemicals, more preferably less than about 20% chemical precursors or non-rp chemicals, still more preferably less than about 10% chemical precursors or non-rp chemicals, and most preferably less than about 5% chemical precursors or non-rp chemicals. In preferred embodiments, isolated polypeptides or bioactive fragments or portions thereof lack contaminating proteins from the same animal from which the rp polypeptide is derived. Typically, such polypeptides are produced by recombinant expression of, for example, a human rp polypeptide in a nonhuman cell.

An isolated rp polypeptide or a fragment or portion thereof of the invention can modulate a sensory function, e.g., vision and/or hearing, in a cell involved in sensory functions, e.g., a photoreceptor cell, an audioreceptor cell, a function associated with body weight, and/or a metabolic function. In preferred embodiments, the polypeptide or fragment thereof comprises an amino acid sequence which is sufficiently homologous to an amino acid sequence of SEQ ID NO:2, an amino acid sequence which is encoded by the nucleotide sequence of the DNA insert of the plasmid deposited with ATCC as Accession Number 98144, or an amino acid sequence which is encoded by the nucleotide sequence of the DNA insert of the plasmid deposited with ATCC as Accession Number 98147 such that the polypeptide or fragment thereof maintains the ability to modulate a sensory function in a cell involved in sensory functions. The fragment of the polypeptide is preferably a bioactive fragment as described herein. In another preferred embodiment, the rp polypeptide (i.e., amino acid residues 1–349) has an amino acid sequence shown in SEQ ID NO:2, an amino acid sequence which is encoded by the nucleotide sequence of the DNA insert of the plasmid deposited with ATCC as Accession Number 98144, or an amino acid sequence which is encoded by the nucleotide sequence of the DNA insert of the plasmid deposited with ATCC as Accession Number 98147. In yet another preferred embodiment, the rp polypeptide has an amino acid sequence which is encoded by a nucleotide sequence which hybridizes, e.g., hybridizes under stringent conditions, to the nucleotide sequence of the DNA insert of the plasmid deposited with ATCC as Accession Number 98144, or the nucleotide sequence of the DNA insert of the plasmid deposited with ATCC as Accession Number 98147. In still another preferred embodiment, the rp polypeptide has an amino acid sequence which is encoded by a nucleotide sequence that is at least about 60–65%, preferably at least about 70–75%, more preferably at least about 80–85%, and even more preferably at least about 90–95% or more homologous to the nucleotide sequence of the DNA insert of the plasmid deposited with ATCC as Accession Number 98144 or the nucleotide sequence of the DNA insert of the plasmid deposited with ATCC as Accession Number 98147. The preferred rp polypeptides of the present invention also preferably possess at least one of the rp activities described herein. For example, a preferred rp polypeptide of the present invention includes an amino acid sequence encoded by a nucleotide sequence which hybridizes, e.g., hybridizes under stringent conditions, to the nucleotide sequence of the DNA insert of the plasmid deposited with ATCC as Accession Number 98144 or to the nucleotide sequence of the DNA insert of the plasmid deposited with ATCC as Accession Number 98147 and which can modulate a sensory function in a cell involved in sensory functions.

In other embodiments, the rp polypeptide is substantially homologous to the amino acid sequence of SEQ ID NO:2 and retains the functional activity of the protein of SEQ ID NO:2 yet differs in amino acid sequence due to natural allelic variation or mutagenesis, as described in detail in subsection I above. Accordingly, in another embodiment, the rp polypeptide is a polypeptide which comprises an amino acid sequence which is at least about 50–60%, preferably at least about 65–70%, and more preferably at least about 75, 80, 85, 90%, and most preferably at least about 95% or more homologous to the entire amino acid sequence of SEQ ID NO:2 and which has at least one of the rp activities described herein.

Bioactive fragments or portions of the rp polypeptide include peptides comprising amino acid sequences derived from the amino acid sequence of the rp protein, e.g., the amino acid sequence shown in SEQ ID NO:2 or the amino acid sequence of a protein homologous to the rp protein, which include less amino acids than the full length rp protein or the full length protein which is homologous to the rp protein, and exhibit at least one activity of the rp protein. Typically, bioactive fragments or portions (peptides, e.g., peptides which are, for example, 5, 10, 15, 20, 30, 35, 36, 37, 38, 39, 40, 50, 100 or more amino acids in length) comprise a domain or motif, e.g., the C-terminal portion, e.g., the C-terminal half of the rp polypeptide or a portion thereof including the C-terminal most cysteine residue, a nuclear localization site, a tyrosine phosphorylation site, e.g., a tyrosine phosphorylation site capable of binding to an SH2-containing protein. Moreover, other biologically active portions, in which other regions of the protein are deleted, can be prepared by recombinant techniques and evaluated for one or more of the activities described herein. Preferably, the biologically active portions of the rp polypeptide include one or more selected domains/motifs or portions thereof having biological activity.

Rp polypeptides are preferably produced by recombinant DNA techniques. For example, a nucleic acid molecule encoding the polypeptide is cloned into an expression vector (as described above), the expression vector is introduced into a host cell (as described above) and the rp polypeptide is expressed in the host cell. The rp polypeptide can then be isolated from the cells by an appropriate purification scheme using standard protein purification techniques. Alternative to recombinant expression, an rp protein, polypeptide, or peptide can be synthesized chemically using standard peptide synthesis techniques. Moreover, native rp protein can be isolated from cells (e.g., retinal cells), for example using an anti-rp antibody (described further below).

The invention also provides rp chimeric or fusion proteins. As used herein, an rp "chimeric protein" or "fusion protein" comprises an rp polypeptide operatively linked to a non-rp polypeptide. An "rp polypeptide" refers to a polypeptide having an amino acid sequence corresponding to rp, whereas a "non-rp polypeptide" refers to a polypeptide having an amino acid sequence corresponding to a protein which is not substantially homologous to the rp polypeptide, e.g., a protein which is different from the rp polypeptide and which is derived from the same or a different organism. Within the fusion protein, the term "operatively linked" is intended to indicate that the rp polypeptide and the non-rp polypeptide are fused in-frame to each other. The non-rp polypeptide can be fused to the N-terminus or C-terminus of the rp polypeptide. For example, in one embodiment the fusion protein is a GST-rp fusion protein in which the rp sequences are fused to the C-terminus of the GST sequences. Such fusion proteins can facilitate the purification of recombinant rp. In another embodiment, the fusion protein is an rp polypeptide containing a heterologous signal sequence at its N-terminus. In certain host cells (e.g., mammalian host cells), expression and/or secretion of rp can be increased through use of a heterologous signal sequence.

Preferably, an rp chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be performed using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An rp-encoding nucleic acid can be cloned into such an expression vector such that the fusion moiety is linked in-frame to the rp polypeptide.

The present invention also pertains to homologues of the rp polypeptides which function as either an rp agonist (mimetic) or an rp antagonist. In a preferred embodiment, the rp agonists and antagonists stimulate or inhibit, respectively, a subset of the biological activities of the naturally occurring form of the rp polypeptide. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the rp polypeptide.

Homologues of the rp polypeptide can be generated by mutagenesis, e.g., discrete point mutation or truncation of the rp polypeptide. As used herein, the term "homologue" refers to a variant form of the rp polypeptide which acts as an agonist or antagonist of the activity of the rp polypeptide. An agonist of the rp polypeptide can retain substantially the same, or a subset, of the biological activities of the rp polypeptide. An antagonist of the rp polypeptide can inhibit one or more of the activities of the naturally occurring form of the rp polypeptide, by, for example, competitively binding to a downstream or upstream member of the rp cascade which includes the rp polypeptide. Thus, the mammalian rp polypeptide and homologues thereof of the present invention can be either positive or negative regulators of sensory functions in cells involved in sensory functions or of another function described herein.

In an alternative embodiment, homologues of the rp polypeptide can be identified by screening combinatorial libraries of mutants, e.g., truncation mutants, of the rp polypeptide for rp polypeptide agonist or antagonist activity. In one embodiment, a variegated library of rp variants is generated by combinatorial mutagenesis at the nucleic acid level and is encoded by a variegated gene library. A variegated library of rp variants can be produced by, for example, enzymatically ligating a mixture of synthetic oligonucleotides into gene sequences such that a degenerate set of potential rp sequences is expressible as individual polypeptides, or alternatively, as a set of larger fusion proteins (e.g., for phage display) containing the set of rp sequences therein. There are a variety of methods which can be used to produce libraries of potential rp homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential rp sequences. Methods for synthesizing degenerate oligonucleotides are known in the art (see, e.g., Narang, S. A. (1983) *Tetrahedron* 39:3; Itakura et al. (1984) *Annu. Rev. Biochem*. 53:323; Itakura et al. (1984) *Science* 198:1056; Ike et al. (1983) *Nucleic Acid Res*. 11:477.

In addition, libraries of fragments of the rp polypeptide coding can be used to generate a variegated population of rp fragments for screening and subsequent selection of homologues of an rp polypeptide. In one embodiment, a library of coding sequence fragments can be generated by treating a double stranded PCR fragment of an rp coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the rp polypeptide.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of rp homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify rp homologues (Arkin and Yourvan (1992) *PNAS* 89:7811–7815; Delgrave et al. (1993) *Protein Engineering* 6(3):327–331).

An isolated rp polypeptide, a fragment or portion thereof, can be used as an immunogen to generate antibodies that bind to or specifically react with rp using standard techniques for polyclonal and monoclonal antibody preparation. The full-length rp protein can be used or, alternatively, the invention provides antigenic peptide fragments of rp for use as immunogens. The antigenic peptide of rp comprises at least 8 amino acid residues of the amino acid sequence shown in SEQ ID NO:2 and encompasses an epitope of rp such that an antibody raised against the peptide forms a specific immune complex with rp. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of rp that are located on the surface of the protein, e.g., hydrophilic regions.

An rp immunogen typically is used to prepare antibodies by immunizing a suitable subject (e.g., rabbit, goat, mouse or other mammal) with the immunogen. An appropriate immunogenic preparation can contain, for example, recombinantly expressed rp protein or a chemically synthesized rp peptide. The preparation can further include an adjuvant, such as Freund's complete or incomplete adjuvant, or similar immunostimulatory agent. Immunization of a suitable subject with an immunogenic rp preparation induces a polyclonal anti-rp antibody response.

Accordingly, another aspect of the invention pertains to anti-rp antibodies. The term "antibody" as used herein refers to immunoglobulin molecules and immunologically active portions of immunoglobulin molecules, i.e., molecules that contain an antigen binding site which specifically binds (immunoreacts with) an antigen, such as rp. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind rp. The term "monoclonal antibody" or "monoclonal antibody composition", as used herein, refers to a population of antibody molecules that contain only one species of an antigen binding site capable of immunoreacting with a particular epitope of rp. A monoclonal antibody composition thus typically displays a single binding affinity for a particular rp protein with which it immunoreacts.

Polyclonal anti-rp antibodies can be prepared as described above by immunizing a suitable subject with an rp immunogen. The anti-rp antibody titer in the immunized subject can be monitored over time by standard techniques, such as with an enzyme linked immunosorbent assay (ELISA) using immobilized rp. If desired, the antibody molecules directed against rp can be isolated from the mammal (e.g., from the blood) and further purified by well known techniques, such as protein A chromatography to obtain the IgG fraction. At an appropriate time after immunization, e.g., when the anti-rp antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *PENAS* 76:2927–31; and Yeh et al. (1982) *Int. J Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an rp immunogen as described above, and the culture supernatants of the resulting hybridoma cells are screened to identify a hybridoma producing a monoclonal antibody that binds rp.

Any of the many well known protocols used for fusing lymphocytes and immortalized cell lines can be applied for the purpose of generating an anti-rp monoclonal antibody (see, e.g., G. Galfre et al. (1977) *Nature* 266:55052; Gefter et al. *Somatic Cell Genet.*, cited supra; Lerner, *Yale J Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind rp, e.g., using a standard ELISA assay.

Alternative to preparing monoclonal antibody-secreting hybridomas, a monoclonal anti-rp antibody can be identified and isolated by screening a recombinant combinatorial immunoglobulin library (e.g., an antibody phage display library) with rp to thereby isolate immunoglobulin library members that bind rp. Kits for generating and screening phage display libraries are commercially available (e.g., the Pharmacia *Recombinant Phage Antibody System*, Catalog No. 27-9400-01; and the Stratagene *SurZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-rp antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494;

Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. 5,225,539; Jones et al. (1986) *Nature* 321:552–525; Verhoeyan et al. (1988) *Science* 239:1534; and Beidler et al. (1988) *J. Immunol.* 141:4053–4060.

An anti-rp antibody (e.g., monoclonal antibody) can be used to isolate rp by standard techniques, such as affinity chromatography or immunoprecipitation. An anti-rp antibody can facilitate the purification of natural rp from cells and of recombinantly produced rp expressed in host cells. Moreover, an anti-rp antibody can be used to detect rp protein (e.g., in a cellular lysate or cell supernatant) in order to evaluate the abundance and pattern of expression of the rp protein. Anti-rp antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

IV. Pharmaceutical Compositions

The rp nucleic acid molecules, rp proteins, rp modulators, and anti-rp antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifuigal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an rp protein or anti-rp antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, polypeptides, polypeptide homologues, modulators, and antibodies described herein can be used in one or more of the following methods: 1) drug screening assays; 2) diagnostic assays; and 3) methods of treatment. An rp polypeptide of the invention has one or more of the activities described herein and can thus be used to, for example, modulate a sensory function in a cell involved in sensory functions. The isolated nucleic acid molecules of the invention can be used to express rp polypeptide (e.g., via a recombinant expression vector in a host cell in gene therapy applications), to detect rp mRNA (e.g., in a biological sample) or a genetic lesion in an rp gene, and to modulate rp activity, as described further below. In addition, the rp proteins can be used to screen drugs or compounds which modulate rp polypeptide activity as well as to treat disorders characterized by insufficient production of rp polypeptide or production of rp polypeptide forms which have decreased activity compared to wild type rp. Moreover, the anti-rp antibodies of the invention can be used to detect and isolate rp polypeptide and modulate rp polypeptide activity.

a. Drug Screening Assays:

The invention provides methods for identifying compounds or agents which can be used to treat disorders characterized by (or associated with) aberrant or abnormal rp nucleic acid expression and/or rp polypeptide activity. These methods are also referred to herein as drug screening assays and typically include the step of screening a candidate/test compound or agent for the ability to interact with (e.g., bind to) an rp polypeptide, to modulate the interaction of an rp polypeptide and a target molecule, and/or to modulate rp nucleic acid expression and/or rp polypeptide activity. Candidate/test compounds or agents which have one or more of these abilities can be used as drugs to treat disorders characterized by aberrant or abnormal rp nucleic acid expression and/or rp polypeptide activity. Candidate/test compounds include, for example, 1) peptides such as soluble peptides, including Ig-tailed fusion peptides and members of random peptide libraries (see, e.g., Lam, K. S. et al. (1991) *Nature* 354:82–84; Houghten, R. et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767–778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

In one embodiment, the invention provides assays for screening candidate/test compounds which interact with (e.g., bind to) rp polypeptide. Typically, the assays are cell-free assays which include the steps of combining an rp polypeptide or a bioactive fragment thereof, and a candidate/test compound, e.g., under conditions which allow for interaction of (e.g., binding of) the candidate/test compound to the rp polypeptide or fragment thereof to form a complex, and detecting the formation of a complex, in which the ability of the candidate compound to interact with (e.g., bind to) the rp polypeptide or fragment thereof is indicated by the presence of the candidate compound in the complex. Formation of complexes between the rp polypeptide and the candidate compound can be quantitated, for example, using standard immunoassays.

In another embodiment, the invention provides screening assays to identify candidate/test compounds which modulate (e.g., stimulate or inhibit) the interaction (and most likely rp activity as well) between an rp polypeptide and a molecule (target molecule) with which the rp polypeptide normally interacts. Examples of such target molecules includes proteins in the same signaling path as the rp polypeptide, e.g., proteins which may function upstream (including both stimulators and inhibitors of activity) or downstream of the rp polypeptide in a sensory function signaling pathway or in a pathway involving regulation of body weight, e.g., a TUB interactor protein (e.g., hTI-2). Typically, the assays are cell-free assays which include the steps of combining an rp polypeptide or a bioactive fragment thereof, an rp target molecule (e.g., an rp ligand) and a candidate/test compound, e.g., under conditions wherein but for the presence of the candidate compound, the rp polypeptide or biologically active portion thereof interacts with (e.g., binds to) the target molecule, and detecting the formation of a complex which includes the rp polypeptide and the target molecule or detecting the interaction/reaction of the rp polypeptide and the target molecule. Detection of complex formation can include direct quantitation of the complex by, for example, measuring inductive effects of the rp polypeptide. A statistically significant change, such as a decrease, in the interaction of the rp and target molecule (e.g., in the formation of a complex between the rp and the target molecule) in the presence of a candidate compound (relative to what is detected in the absence of the candidate compound) is indicative of a modulation (e.g., stimulation or inhibition) of the interaction between the rp polypeptide and the target molecule. Modulation of the formation of complexes between the rp polypeptide and the target molecule can be quantitated using, for example, an immunoassay.

To perform the above drug screening assays, it is desirable to immobilize either rp or its target molecule to facilitate separation of complexes from uncomplexed forms of one or both of the proteins, as well as to accommodate automation of the assay. Interaction (e.g., binding of) of rp to a target molecule, in the presence and absence of a candidate compound, can be accomplished in any vessel suitable for containing the reactants. Examples of such vessels include microtitre plates, test tubes, and micro-centrifuge tubes. In one embodiment, a fusion polypeptide can be provided which adds a domain that allows the polypeptide to be bound to a matrix. For example, glutathione-S-transferase/rp fusion polypeptides can be adsorbed onto glutathione sepharose beads (Sigma Chemical, St. Louis, Mo.) or glutathione derivatized microtitre plates, which are then combined with the cell lysates (e.g. $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of rp-binding polypeptide found in the bead fraction quantitated from the gel using standard electrophoretic techniques.

Other techniques for immobilizing polypeptides on matrices can also be used in the drug screening assays of the invention. For example, either rp or its target molecule can be immobilized utilizing conjugation of biotin and streptavidin. Biotinylated rp molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with rp but which do not interfere with binding of the polypeptide to its target molecule can be derivatized to the wells of the plate, and rp trapped in the wells by antibody conjugation. As described above, preparations of a rebinding polypeptide and a candidate compound are incubated in the representing wells of the plate, and the amount of complex trapped in the well can be quantitated. Methods for detecting such complexes, in addition to those described above for the GST-immobilized complexes, include immunodetection of complexes using antibodies reactive with the rp target molecule, or which are reactive with rp polypeptide and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal rp nucleic acid expression or rp polypeptide activity. This method typically includes the step of assaying the ability of the compound or agent to modulate the expression of the rp nucleic acid or the activity of the rp polypeptide thereby identifying a compound for treating a disorder characterized by aberrant or abnormal rp nucleic acid expression or rp polypeptide activity. Disorders characterized by aberrant or abnormal rp nucleic acid expression or rp polypeptide activity are described herein. Methods for assaying the ability of the compound or agent to modulate the expression of the rp nucleic acid or activity of the rp polypeptide are typically cell-based assays. For example, cells which are sensitive to ligands which transduce signals via a pathway involving rp can be induced to overexpress an rp polypeptide in the presence and absence of a candidate compound. Candidate compounds which produce a statistically significant change in rp-dependent responses (either stimulation or inhibition) can be identified. In one embodiment, expression of the rp nucleic acid or activity of an rp polypeptide is modulated in cells and the effects of candidate compounds on the readout of interest (such as rate of cell proliferation or differentiation) are measured. For example, the expression of genes which are up- or down-regulated in response to an rp-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of rp or rp target molecules can also be measured, for example, by immunoblotting.

Alternatively, modulators of rp expression (e.g., compounds which can be used to treat a disorder characterized by aberrant or abnormal rp nucleic acid expression or rp polypeptide activity) can be identified in a method wherein a cell is contacted with a candidate compound and the expression of rp mRNA or polypeptide in the cell is determined. The level of expression of rp mRNA or polypeptide in the presence of the candidate compound is compared to the level of expression of rp mRNA or polypeptide in the absence of the candidate compound. The candidate compound can then be identified as a modulator of rp nucleic acid expression based on this comparison and be used to treat a disorder characterized by aberrant rp nucleic acid expression. For example, when expression of rp mRNA or polypeptide is greater (statistically significantly greater) in the presence of the candidate compound than in its absence, the candidate compound is identified as a stimulator of rp nucleic acid expression. Alternatively, when rp nucleic acid expression is less (statistically significantly less) in the presence of the candidate compound than in its absence, the candidate compound is identified as an inhibitor of rp nucleic acid expression. The level of rp nucleic acid expression in the cells can be determined by methods described herein for detecting rp mRNA or protein.

In yet another aspect of the invention, the rp polypeptides can be used as "bait proteins" in a two-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins, which bind to or interact with rp ("rp-binding proteins" or "rp-bp") and modulate rp polypeptide activity. Such rebinding proteins are also likely to be involved in the propagation of signals by the rp polypeptides as, for example, upstream or downstream elements of the rp pathway.

The two-hybrid system is based on the modular nature of most transcription factors, which consist of separable DNA-binding and activation domains. Bartel, P. et al. "Using the Two-Hybrid System to Detect Protein-Protein Interactions" in Cellular Interactions in Development: A Practical Approach, Hartley, D. A. ed. (Oxford University Press, Oxford, 1993) pp. 153–179. Briefly, the assay utilizes two different DNA constructs. In one construct, the gene that codes for rp is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" proteins are able to interact, in vivo, forming an rp-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with rp.

Modulators of rp polypeptide activity and/or rp nucleic acid expression identified according to these drug screening assays can be used to treat, for example, sensory disorders, e.g., disorders which affect vision and/or hearing, disorders associated with body weight, and/or metabolic disorders. These methods of treatment include the steps of administering the modulators of rp polypeptide activity and/or nucleic acid expression, e.g., in a pharmaceutical composition as described in subsection IV above, to a subject in need of such treatment, e.g., a subject with a disorder described herein.

b. Diagnostic Assays:

The invention further provides a method for detecting the presence of rp in a biological sample. The method involves contacting the biological sample with a compound or an agent capable of detecting rp polypeptide or mRNA such that the presence of rp is detected in the biological sample. A preferred agent for detecting rp mRNA is a labeled or labelable nucleic acid probe capable of hybridizing to rp mRNA. The nucleic acid probe can be, for example, the full-length rp cDNA of SEQ ID NO:1, or a portion thereof, such as an oligonucleotide of at least 15, 30, 50, 100, 250 or 500 nucleotides in length and sufficient to specifically hybridize under stringent conditions to rp mRNA. A preferred agent for detecting rp polypeptide is a labeled or labelable antibody capable of binding to rp protein. Antibodies can be polyclonal, or more preferably, monoclonal. An intact antibody, or a fragment thereof (e.g., Fab or $F(ab')_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect rp mRNA or polypeptide in a biological sample in vitro as well as in vivo. For example, in vitro techniques for detection of rp mRNA include Northern hybridizations and in situ hybridizations. In vitro techniques for detection of rp polypeptide include enzyme linked immunosorbent assays (ELISAs), Western blots, immunoprecipitations and immunofluorescence. Alternatively, rp polypeptide can be detected in vivo in a subject by introducing into the subject a labeled anti-rp antibody. For example, the antibody can be labeled with a radioactive marker whose presence and location in a subject can be detected by standard imaging techniques.

The invention also encompasses kits for detecting the presence of rp in a biological sample. For example, the kit can comprise a labeled or labelable compound or agent capable of detecting rp polypeptide or mRNA in a biological sample; means for determining the amount of rp in the sample; and means for comparing the amount of rp in the sample with a standard. The compound or agent can be packaged in a suitable container. The kit can further comprise instructions for using the kit to detect rp mRNA or protein.

The methods of the invention can also be used to detect genetic lesions in a rp gene, thereby determining if a subject with the lesioned gene is at risk for a disorder characterized by aberrant or abnormal rp nucleic acid expression or rp polypeptide activity as defined herein. In preferred embodiments, the methods include detecting, in a sample of cells from the subject, the presence or absence of a genetic lesion characterized by at least one of an alteration affecting the integrity of a gene encoding an rp polypeptide, or the misexpression of the rp gene. For example, such genetic lesions can be detected by ascertaining the existence of at least one of 1) a deletion of one or more nucleotides from an rp gene; 2) an addition of one or more nucleotides to an rp gene; 3) a substitution of one or more nucleotides of an rp gene, 4) a chromosomal rearrangement of an rp gene; 5) an alteration in the level of a messenger RNA transcript of an rp gene, 6) aberrant modification of an rp gene, such as of the methylation pattern of the genomic DNA, 7) the presence of a non-wild type splicing pattern of a messenger RNA transcript of an rp gene, 8) a non-wild type level of an rp-protein, 9) allelic loss of an rp gene, and 10) inappropriate post-translational modification of an rp-protein. As described herein, there are a large number of assay techniques known in the art which can be used for detecting lesions in an rp gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the rp-gene (see Abravaya et al. (1995) *Nucleic Acids Res*. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an rp gene under conditions such that hybridization and amplification of the rp-gene (if present) occurs, and detecting the presence or absence of an amplification product, or detecting the size of the amplification product and comparing the length to a control sample.

In an alternative embodiment, mutations in an rp gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the rp gene and detect mutations by comparing the sequence of the sample rp with the corresponding wild-type (control) sequence. Examples of sequencing reactions include those based on techniques developed by Maxim and Gilbert ((1977) *PNAS* 74:560) or Sanger ((1977) *PNAS* 74:5463). A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr*. 36:127–162; and Griffin et al. (1993) *Appl. Biochem. Biotechnol*. 38:147–159).

Other methods for detecting mutations in the rp gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol*. 217:286–295), electrophoretic mobility of mutant and wild type nucleic acid is compared (Orita et al. (1989) *PNAS* 86:2766; Cotton (1993) *Mutat Res* 285:125–144; and Hayashi (1992) *Genet Anal Tech Appl* 9:73–79), and movement of mutant or wild-type fragments in polyacrylamide gels containing a gradient of denaturant is assayed using denaturing gradient gel electrophoresis (Myers et al (1985) *Nature* 313:495). Examples of other techniques for detecting point mutations include, selective oligonucleotide hybridization, selective amplification, and selective primer extension.

c. Methods of Treatment

Another aspect of the invention pertains to methods for treating a subject, e.g., a human, having a disease or disorder characterized by (or associated with) aberrant or abnormal rp nucleic acid expression and/or rp polypeptide activity. These methods include the step of administering an rp modulator to the subject such that treatment occurs. The language "aberrant or abnormal rp expression" refers to expression of a non-wild-type rp polypeptide or a non-wild-type level of expression of an rp polypeptide. Aberrant or abnormal rp activity refers to a non-wild-type rp activity or a non-wild-type level of rp activity. As the rp polypeptide is involved in a pathway involving sensory functions, functions associated with body weight, and metabolic functions, aberrant or abnormal rp activity or expression interferes with the normal sensory functions, functions associated with body weight, and/or metabolic functions. Non-limiting examples of disorders or diseases characterized by or associated with abnormal or aberrant rp activity or expression include sensory disorders, disorders associated with body weight, and metabolic disorders. Sensory disorders are disorders which detrimentally affect normal sensory function. Examples of sensory disorders include disorders which affect vision, e.g., disorders of the cells of the retina, e.g., disorders of photoreceptor cells (e.g., rods and cones) of the retina, e.g., retinitis pigmentosa, and disorders which affect hearing (e.g., hearing loss in Usher syndrome types I, II, and II). In addition, there are several abnormalities which are associated with the sensory disorder retinitis pigmentosa. These abnormalities include polydactyly, obesity, hypogonadism, mental retardation in Bardet-Biedl syndrome, and cardiac conduction defects in Kearns-Sayre syndrome. These additional abnormalities can also be treated according to the methods of the present invention. Disorders associated with body weight are disorders associated with abnormal body weight or abnormal control of body weight. Examples of disorders associated with body weight include obesity, cachexia, and anorexia. Metabolic disorders are disorders associated with abnormal metabolism, e.g., abnormal energy source utilization. An example of a metabolic disorder is diabetes. The terms "treating" or "treatment", as used herein, refer to reduction or alleviation of at least one adverse effect or symptom of a disorder or disease, e.g., a disorder or disease characterized by or associated with abnormal or aberrant rp polypeptide activity or rp nucleic acid expression.

As used herein, an rp modulator is a molecule which can modulate rp nucleic acid expression and/or rp polypeptide activity. For example, an rp modulator can modulate, e.g., upregulate (activate) or downregulate (suppress), rp nucleic acid expression. In another example, an rp modulator can modulate (e.g., stimulate or inhibit) rp polypeptide activity. If it is desirable to treat a disorder or disease characterized by (or associated with) aberrant or abnormal (non-wild-type) rp nucleic acid expression and/or rp polypeptide activity by inhibiting rp nucleic acid expression, an rp modulator can be an antisense molecule, e.g., a ribozyme, as described herein. Examples of antisense molecules which can be used to inhibit rp nucleic acid expression include antisense molecules which are complementary to a portion of the 5' untranslated region of SEQ ID NO:1 which also includes the start codon and antisense molecules which are complementary to a portion of the 3' untranslated region of SEQ ID NO:1. An example of an antisense molecule which is complementary to a portion of the 5' untranslated region of SEQ ID NO:1 and which also includes the start codon is a nucleic acid molecule which includes nucleotides which are complementary to nucleotides 551 to 571 of SEQ ID NO:1. This antisense molecule has the following nucleotide sequence: 5' CGTCCCCTCCCCTGGTTCTAC 3' (SEQ ID NO:12). An example of an antisense molecule which is complementary to a portion of the 3' untranslated region of SEQ ID NO:1 is a nucleic acid molecule which includes nucleotides which are complementary to nucleotides 1637 to 1656 of SEQ ID NO:1. This antisense molecule has the following sequence: 5° CGCTGACGGGCTCTGGGGGC 3' (SEQ ID NO:13). An additional example of an antisense molecule which is complementary to a portion of the 3' untranslated region of SEQ ID NO:1 is a nucleic acid molecule which includes nucleotides which are complementary to nucleotides 1667 to 1684 of SEQ ID NO:1. This antisense molecule has the following sequence: 5' GCCAGCCTCCACTGAATC 3' (SEQ ID NO:14). An rp modulator which inhibits rp nucleic acid expression can also be a small molecule or other drug, e.g., a small molecule or drug identified using the screening assays described herein, which inhibits rp nucleic acid expression. If it is desirable to treat a disease or disorder characterized by (or associated with) aberrant or abnormal (non-wild-type) rp nucleic acid expression and/or rp polypeptide activity by stimulating rp nucleic acid expression, an rp modulator can be, for example, a nucleic acid molecule encoding rp (e.g., a nucleic acid molecule comprising a nucleotide sequence homologous to the nucleotide sequence of SEQ ID NO:1) or a small molecule or other drug, e.g., a small molecule (peptide) or drug identified using the screening assays described herein, which stimulates rp nucleic acid expression.

Alternatively, if it is desirable to treat a disease or disorder characterized by (or associated with) aberrant or abnormal (non-wild-type) rp nucleic acid expression and/or rp polypeptide activity by inhibiting rp polypeptide activity, an rp modulator can be an anti-rp antibody or a small molecule or other drug, e.g., a small molecule or drug identified using the screening assays described herein, which inhibits rp polypeptide activity. If it is desirable to treat a disease or disorder characterized by (or associated with) aberrant or abnormal (non-wild-type) rp nucleic acid expression and/or rp polypeptide activity by stimulating rp polypeptide activity, an rp modulator can be an active rp polypeptide or portion thereof (e.g., an rp polypeptide or portion thereof having an amino acid sequence which is homologous to the amino acid sequence of SEQ ID NO:2 or a portion thereof) or a small molecule or other drug, e.g., a small molecule or drug identified using the screening assays described herein, which stimulates rp polypeptide activity.

In addition, a subject having a retinitis pigmentosa can be treated according to the present invention by administering to the subject an rp polypeptide or portion thereof or a nucleic acid encoding an rp polypeptide or portion thereof such that treatment occurs. Similarly, a subject having a disorder associated with body weight can be treated according to the present invention by administering to the subject an rp polypeptide or portion thereof or a nucleic acid encoding an rp polypeptide or portion thereof such that treatment occurs.

Other aspects of the invention pertain to methods for modulating a cell associated activity. These methods include contacting the cell with an agent (or a composition which includes an effective amount of an agent) which modulates rp polypeptide activity or rp nucleic acid expression such that a cell associated activity is altered relative to a cell associated activity of the cell in the absence of the agent. As used herein, "a cell associated activity" refers to a normal or abnormal activity or .unction of a cell. Examples of cell associated activities include proliferation, migration, differentiation, production or secretion of molecules, such as proteins, and cell survival. In a preferred embodiment, the cell is neural cell of the retina, e.g., photoreceptor cell of the retina, e.g., a rod or cone photoreceptor cell of the retina. The term "altered" as used herein refers to a change, e.g., an increase or decrease, of a cell associated activity. In one embodiment, the agent stimulates rp polypeptide activity or rp nucleic acid expression. Examples of such stimulatory agents include an active rp protein, a nucleic acid molecule encoding rp that has been introduced into the cell, and a modulatory agent which stimulates rp polypeptide activity or rp nucleic acid expression and which is identified using the drug screening assays described herein. In another embodiment, the agent inhibits rp polypeptide activity or rp nucleic acid expression. Examples of such inhibitory agents include an antisense rp nucleic acid molecule, an anti-rp antibody, and a modulatory agent which inhibits rp polypeptide activity or rp nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant rp polypeptide activity or rp nucleic acid expression.

A nucleic acid molecule, a polypeptide, an rp modulator, a compound etc. used in the methods of treatment can be incorporated into an appropriate pharmaceutical composition described herein and administered to the subject through a route which allows the molecule, polypeptide, modulator, or compound etc. to perform its intended function. Examples of routes of administration are also described herein under subsection IV.

The present invention is further illustrated by the following examples which should not be construed as limiting. The contents of all cited references (including literature references, issued patents, published patent applications, and co-pending patent applications) cited throughout this application are hereby expressly incorporated by reference.

EXAMPLES

Example 1

Identification of the Human RP Gene

The nucleotide sequence of the mouse tub gene (Kleyn, P. W. et al. (1996) *Cell* 85:281–290) was used as a database query using the BLASTN program (BLASTN1.3MP, Altschul et al. (1990) *J. Mol. Biol.* 215:403). This database query resulted in the identification of a human EST (GenBank™ Accession Number H92408 deposited by The Washington University-Merck EST Project, Washington University School of Medicine, St. Louis, Mo.) which was originally derived from a human retinal library and which includes 404 nucleotides. When the derived amino acid sequence of this EST was compared to the amino acid sequence of the htub protein, it was 75.3% identical over 85 amino acid residues to the amino acid residues 246 to 330 of the htub protein.

Upon identification of the EST, the corresponding clone (GenBank™ Accession Number H92408) was obtained from Research Genetics, Inc (Catalog No. 97002, Huntsville, Ala.) and sequenced. The sequencing of the Research Genetics, Inc. clone revealed several discrepancies between the sequence of the clone obtained from Research Genetics, Inc., and the sequence shown as GenBank™ Accession Number H92408. These discrepancies were determined to be errors in the GenBank™ nucleotide sequence. First, the GenBank™ nucleotide sequence was found to include a deletion of a C at position 33 compared to the nucleotide sequence of the clone from Research Genetics, Inc. Second, the GenBank™ nucleotide sequence was found to include nucleotide insertions at positions 330 (C), 339 (G), 359 (G), 366 (T), 375 (T), and 384 (G) compared to the nucleotide sequence of the clone from Research Genetics, Inc. Third, a portion (nucleotides 133–137: ACCGA) of the GenBank™ nucleotide sequence was found to be incorrect when compared to the nucleotide sequence of the clone from Research Genetics, Inc. (the nucleotide sequence of this portion should have been GGCCG). Fourth, the GenBank™ nucleotide sequence was found to include an incorrect nucleotide at position 398 (a T instead of a G) compared to the nucleotide sequence of the clone from Research Genetics, Inc.

The sequence of the clone obtained from Research Genetics, Inc. was used a probe to screen a human retinal cDNA library in λgt11 (Clontech, Palo Alto, Calif.). Approximately $10^6$ plaques were hybridized in duplicate at 65° C. in Churchs buffer solution overnight. The filters were then washed for 30 minutes at 65° C. in 0.1×SSC, .1% SDS, and exposed overnight. This screen yielded 2 positive clones. These clones were replated and rehybridized using the same conditions as above. Once pure, these clones were used to generate λ DNA by a plate lysis method and the λ DNA was digested and subcloned into pBLUESCRIPT. One of these clones (fyhx 77102; 2.2 kb) was shown to contain the full coding sequence of the rp gene.

Example 2

Chromosomal Localization of the Human RP Gene

The rp gene was mapped to chromosome 6p by PCR typing of the Genebridge (G4) radiation hybrid panel (Research Genetics, Inc., Huntsville, Ala.). Typing of the DNA and comparison to radiation hybrid map data at the Whitehead Institute Center for Genome Research (WICGR) tightly linked the rp gene to an anonymous STS, WI-4186, on human chromosome 6. To confirm this rp localization, the rp gene was genetically mapped in the mouse using a C57BL/6J×Mus spretus interspecific backcross. Genotyping of 100 meioses demonstrated linkage to a region on mouse chromosome 17 between D17Mit48 and D7Mit 9.

As the panels used in the mapping studies included both human and hamster sequences, the two primers to be used in the mapping of the rp gene were tested to confirm that they were specific for human DNA rather than hamster DNA. The rp primers used in the PCR mapping studies were: forward -CGTGGAGGTGGACGAACC (SEQ ID NO:15) and reverse -CCGTGTCCAGGTGCAGGA (SEQ ID NO:16) were first tested on human and hamster genomic DNA for specific amplification. Each PCR reaction consisted of: 5 μl (50 ng) genomic DNA, 2 μl primers (10 μM each), 2 μl 10×PCR buffer (15 mM $MgCl_2$, 100 mM Tris-HCl, 500 mM KCl Perkin-Elmer, Corp., Norwalk, Conn.), 1 u Taq polymerase (5 u/μl Perkin-Elmer Corp., Norwalk, Conn.), and 10.8 μl diH20. Reactions were thermocycled on a Perkin-Elmer 9600 for 94° C. 3 minutes, [94° C. 30 sec, 55° C. 30 sec., 72° C., 30 sec.] 35×, 72° C., 7 minutes, 4° C. hold. Resulting PCR products were run out on a 2% agarose gel and visualised on a UV light box. The primers specifically amplified a 150 bp product from human genomic DNA, but no product from hamster genomic DNA.

After the primers to be used in the mapping studies were determined to be specific for human DNA, the radiation hybrid mapping studies were performed as follows: PCR reactions of radiation hybrid panels, GeneBridge 4 (Research Genetics, Inc., Huntsville, Ala.) and Stanford G3 (Research Genetics, Inc., Huntsville, Ala.), were assembled in duplicate using an automated PCR assembly progam on a TECAN Genesis. Each reaction consisted of: 10 μl hybrid DNA (5 ng/μl), 2 μl primers (10 μM each), and 8 μl PCR cocktail (final concentrations: 1.5 mM $MgCl_2$, 10 mM Tris-HCl, 50 mM KCl, 1 u Taq polymerase). The reactions were thermocycled on a Perkin-Elmer 9600 for 94° C. 3 minutes, [94° C. 30 sec, 55° C. 30 sec, 72° C., 30 sec] 35×, 72° C., 7 minutes, 4° C. hold. Resulting PCR products were run out on a 2% agarose gel and visualized on a UV light box.

Positive hybrids for the Genebridge 4 panel were: 1, 8, 13, 18, 22, 26, 31,32, 34, 36, 38, 43, 46, 49, 51, 53, 54, 60, 62, 63, 65, 69, 73, 74, 78, 79, 82, and 84. These data were submitted to the Whitehead Genome Center for placement in relation to a framework map. The placement results mapped the rp gene to chromosome 6, 0.00 cR from Whitehead framework marker WI-4186, with a LOD score >3.0.

Positive hybrids for the Stanford G3 panel were: 8, 9, 14, 16, 27, 29, 49, 62, 64, 66, 67, 68, 72, 81, and 83. These data were submitted to the Stanford Genome Center Radiation Hybrid mapping server for 2 point analysis and placement in relation to a framework map. This resulted in mapping rp gene to chromosome 6, 31.22 cR from Stanford framework marker D6S291, with a LOD score of 7.7.

Knowles et al. ((1994) *Hum. Mol. Genet.* 3:1401–1403) showed that the RP14 gene must lie between the markers D6S272 and D6S271. Knowles et al. also reported that the closest marker to RP14 was D6S291. The results from the radiation hybrid mapping described herein (Whitehead data) show that the rp gene maps between D6S272 and D6S271, the markers that flank RP14. Furthermore, the rp gene does not segregate from D6S291 on the Genebridge radiation hybrid panel indicating that these loci are very tightly linked. It follows that the rp gene is very tightly linked to RP14. In summary, the rp gene clearly maps within the critical region previously shown to contain the RP14 locus and thus is a candidate gene for retinitis pigmentosa.

Example 3

Tissue Expression of the Human RP Gene

Northern Analysis Using RNA from Selected Cell Lines

Poly A+ RNA samples isolated from selected cell lines, many of which were obtained from ATCC, and human retina were probed with the approximately 1.35 kb EcoRI-NotI fragment of the rp nucleotide sequence of the DNA insert of the plasmid deposited with ATCC as Accession Number 98147 using the Fast Track System (Invitrogen, San Diego, Calif.). The ATCC cell lines from which the RNA was isolated included the neuroblastoma cell lines SK-N-MC (human: ATCC Accession Number HTB10), SK-N-SH (human: ATCC Accession Number HTB11), NB41A3 (human: ATCC Accession Number CCL 147), and Neuro-2a (mouse: ATCC Accession Number CCL 131). An additional human neuroblastoma cell line, SH-SY5Y, used in these experiments is described in Reed, J. C. et al. (1991) *Cancer Res.* 51(24): 6529–6538. The retinal poly A+ was obtained from Clontech, Palo Alto, Calif.

The retinal RNA was the only lane that showed a hybridization signal. The major band was approximately 2 kb. Minor bands of 3.0, 3.5, 4.4., 5.0, and 7.5 kb were also detected. These results demonstrate that the rp mRNA is 2 kb. The other more weakly hybridizing bands may be alternatively-spliced rp transcripts or related genes.

Northern Analysis Using RNA from Human Tissue

Human multiple tissue northern blots (Catalog Numbers 7766-1 and 7760-1, Clontech, Palo Alto, Calif.), containing 2 $\mu$g of poly A+ RNA per lane were probed with the approximately 1.35 kb of an EcoRI-NotI fragment of the rp nucleotide sequence of the DNA insert of the plasmid deposited with ATCC as Accession Number 98147. The filters were prehybridized in 5 ml of Church buffer at 65° C. for 1 hour, after which 100 ng of $^{32}$P labelled probe was added. The probe was generated using the Stratagene Prime-It kit, Catalog Number 300392 (Clontech, Palo Alto, Calif.). Hybridization was allowed to proceed at 65° C. for approximately 18 hours. The filters were washed in 0.1% SDS, 0.2×SSC solution at 65° C. and then exposed to the phosphoimager for 4 hours. The human tissues tested included: spleen, thymus, prostate, testis, uterus, small intestine, colon, peripheral blood leukocytes, heart, brain, placenta, lung, liver, skeletal muscle, kidney, and pancreas.

There was no strong hybridization to any of the RNA represented in this Northern blot indicating that the 2 kb rp gene transript is not expressed in any of these tissues. Thus, of the tissues tested in the Northern analyses described herein, only the retinal tissue expressed the rp transcript. A faint 1.2 kb band was observed in skeletal muscle and testis. This probably represents an alternatively-spliced form of the rp transcript or a related gene.

Example 4

Hybridization Experiments Using the Full Length Human RP Gene

The approximately 1.35 kb EcoRI-NotI fragment of the rp nucleotide sequence of the DNA insert of the plasmid deposited with ATCC as Accession Number 98147 was incubated with human and mouse cDNA or genomic libraries under standard conditions (0.5M $NaHPO_4$, 7% dodecyl sulfate (SDS), 1 mM EDTA at 65° C.). The mixture was subsequently washed at high stringency (0.1×SSC, 1% SDS, 68° C., 30 min).

The rp fragment hybridized to rp nucleic acid sequences from the libraries but not to human TUB or mouse tub nucleic acid sequences from the libraries. Thus, under high stringency conditions, this rp fragment does not hybridize to human TUB or mouse tub nucleic acid sequences.

Example 5

Expression of Recombinant Human RP Protein in Mammalian Cells

To express the rp gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire rp protein and an HA tag (Wilson et al. (1984) *Cell* 37:767) fused in-frame to its 3' end of the fragment is cloned into the polylinker region of the vector, thereby placing the expression of the recombinant protein under the control of the CMV promoter.

To construct the plasmid, the rp DNA sequence is amplified by PCR using two primers. The 5' primer contains the restriction site of interest followed by approximately twenty nucleotides of the rp coding sequence starting from the initiation codon; the 3' end sequence contains complementary sequences to the other restriction site of interest, a translation stop codon, the HA tag and the last 20 nucleotides of the rp coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the rp gene is inserted in the correct orientation. The ligation mixture is transformed into *E. coil* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the rp-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, *T. Molecular Cloning: A Laboratory Manual. 2nd, ed., Cold Spring Harbor Laboratory*, Cold Spring Harbor Laboratory Press, Cold Spring Harbor, N.Y., 1989. The expression of the rp protein is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated proteins are then analyzed by SDS-PAGE.

Alternatively, DNA containing the rp coding sequence is cloned directly into the polylinker of the pCDNA/Amp vector using the appropriate restriction sites. The resulting plasmid is transfected into COS cells in the manner described above, and the expression of the rp protein is detected by radiolabelling and immunoprecipitation using an rp specific monoclonal antibody Example 6

The Human RP Protein Binds to the Tub Interactor Protein, hTI-2

The following materials and methods were used in Example 6:

Yeast Strains, Media, and Microbiological Techniques

Yeast strains and plasmids used in Example 6 are listed in Tables 1 and 2. Standard yeast media including synthetic complete medium lacking L-leucine, L-tryptophan, and L-histidine were prepared and yeast genetic manipulations were performed as described (Sherman (1991) *Meth. Enzymol.* 194:3–21). Yeast transformations were performed using standard protocols (Gietz et al. (1992) *Nucleic Acids Res.* 20:1425; Ito et al. (1983) *J. Bacteriol.* 153:163–168) Plasmid DNAs were isolated from yeast strains by a standard method (Hoffman and Winston, (1987) *Gene* 57:267–272).

TABLE 1

Yeast Strains

| Yeast Strain | Genotype | Source or Derivation |
|---|---|---|
| HF7c | MATa ura3-52 his3-200 lys2-801 ade2-101 trpl-901 leu2-3, 112 gal4-542 gal80-538 LYS2::$GAL1_{UAS}$-$GAL1_{TATA}$-H153 URA3::$GAL4_{17mers(x3)}$-$CyCl_{TATA}$-lacz | Feilotter et al. (1994) Nucleic Acids Res. 22:1502–1503 |
| Y187 | MATα gal4 gal80 his3 trpl-901 ade2-101 ura3-52 leu2-3, 112 met-URA3: GAL→lacZ | Bai C. and Elledge, S.J. (1995) Methods Enzymol. 273:331–347. |
| TB24 | HF7c + pMB195 encoding the last 259 amino acid residues of human rp protein | Prepared for experiments described herein. |
| TB19 | HF7c + p53 | Applicants' collection. |
| TB17 | HF7c + pGBT9 | Applicants' collection. |
| TF4 | Y187 + pSV40 | Applicants' collection. |

TABLE 2

Plasmids

| Plasmid Name | Description | Source or Derivation |
|---|---|---|
| pGBT9 | GAL4(1-147) fusion vector marked with TRP1 and $amp^r$ | Bartel, P. et al. "Using the Two-Hybrid System to Detect Protein-Protein Interactions" in Cellular Interactions in Development: A Practical Approach, Hartley, D.A. ed. (Oxford University Press, Oxford, 1993) pp. 153–179. |
| pACTII | GAL4(768–881) fusion vector | Bai, C. and Elledge, S.J. (1995) Methods Enzymol. 273:331–347. |
| pACThTPR | hTPR carboxyl terminus cloned in pACTII | United States Serial Number 08/715,032, filed September 17, 1996. |
| pACThRING | hRING cloned in pACTII | United States Serial Number 08/715,032, filed September 17, 1996. |
| pACThANK | hANK carboxyl terminus cloned in pACTII | United States Serial Number 08/715,032, filed September 17, 1996. |
| pMB95 | pGBT9 with a DNA fragment encoding the last 259 amino acid residues of human rp cloned into it. | Prepared for experiments described herein. |
| p53 | murine $p^{53}{}_{72-390}$ control bait plasmid | HybriZAP Two-Hybrid Vector Kit (Stratagene, LaJolla, CA) |

Plasmid and Yeast Strain Construction

DNA coding the last 259 amino acids of the human rp protein was amplified by PCR and cloned in frame into pGBT9 resulting in plasmid pMB95. pMB95 was transformed into two-hybrid screening strain HF7c, and one resulting transformant was designated TB24.

Two-Hybrid Analysis

Two-hybrid analysis was carried out essentially as described (Bartel, P. et al. "Using the Two-Hybrid System to Detect Protein-Protein Interactions" in Cellular Interactions in Development: A Practical Approach, Hartley, D. A. ed. (Oxford University Press, Oxford, 1993) pp. 153–179).

Beta Galactosidase Assays

The filter disk beta-galactosidase (beta-gal) assay was performed essentially as previously described (Brill et al. (1994) *Mol. Biol. Cell*5:297–312.). Briefly, strains to be tested were grown as patches of cells on appropriate medium dictated by the experiment at 30 ° C. overnight. The patches or colonies of cells were replica plated to Whatman #50 paper disks (Catalog Number 576, Schleicher & Schuell, Keene, N. H.) that had been placed on the test medium in petri dishes. After growth overnight at 30° C., the paper disks were removed from the plates and the cells were permeabilized by immediate immersion in liquid nitrogen for 30 seconds. After this treatment, the paper disks were thawed at room temperature for 20 seconds and then placed in petri dishes that contained a disk of Whatman #3 paper (Catalog Number 593, Schleicher & Schuell, Keene, N. H.) saturated with 2.5 ml of Z buffer containing 37 μl of 2% weight per volume of the chromogenic beta-gal substrate X-gal. The permeabilized strains on the paper disks were incubated at 30° C. and inspected at timed intervals for the blue color diagnostic of beta-gal activity in this assay. The assay was stopped by removing the paper disk containing the patches of cells and air drying it.

DNA encoding the carboxyl terminal 259 amino acids of the human rp protein was amplified by PCR and cloned into pGBT9 creating a GAL4 DNA-binding domain-human rp fusion gene (plasmid pMB95). HF7c was transformed with this construct resulting in strain TB24. TB24 failed to grow on synthetic complete medium lacking L-tryptophan and L-histidine, demonstrating that the GAL4 DNA-binding domain-human rp fusion does not have intrinsic transcriptional activation activity.

To determine whether the human rp protein carboxyl terminal bait could interact with the human TUB interactor (hTI) fish proteins: hTI-2 (hANK), hTI-3 (hTPR), and hTI-4 (hRING) (described in U.S. Ser. No. 08/715,032, filed Sep. 17, 1996), a yeast two-hybrid assay was performed. Yeast expression plasmids described in the above materials and methods section encoding the GAL4 DNA-binding domain alone and fused in-frame to the human rp protein and the p53 control gene were transformed into MATa two-hybrid screening strain HF7c. Yeast expression plasmids encoding GAL4 activation domain fusions to hTI-2 (hANK), hTI-3 (hTPR), and hTI-4 (hRING) and the SV40 large T-antigen were transformed into AMTα two-hybrid screening strain Y187. p53 and SV40 interact with each other and should not interact with the experimental proteins.

The HF7c transformants were propagated as stripes on semisolid synthetic complete medium lacking L-tryptohan and the Y187 transformants were grown as stripes on semisolid synthetic complete medium lacking L-leucine. Both sets of stripes were replica plated in the form of a grid onto a single rich YPAD plate and the hapliod strains of opposite mating types were allowed to mate overnight at 30° C. The yeast strains on the mating plate were then replica plated to a synthetic complete plate lacking L-leucine and L-tryptophan to select for diploids and incubated at 30° C. overnight. Diploid strains on the synthetic complete plate lacking L-leucine and L-tryptophan were replica plated to a synthetic complete plate lacking L-eucine, L-tryptophan, and L-histidine to assay HIS3 expression. HIS3 expression was scored after 3 days of growth at 30° C. The results of this experiment are shown in Table 3. The strength or absence of physical interaction between each combination of test proteins is listed in this Table. Strong interacitons are defined as interactions that cause the activation of the HIS3 reporter gene.

TABLE 3

| GAL4 DNA-Binding Domain Fusions | cDNA-GAL4 Activation Domain Fusion Tested hTI-2 | hTI-3 | hTI-4 | SV40 |
|---|---|---|---|---|
| rp protein | strong | none | none | none |
| p53 control | none | none | none | strong |
| GAL4 binding domain alone | none | none | ndne | none |

The hTI-2, hTI-3, and hTI-4 proteins were originally isolated as interactors with the carboxyl-terminus of TUB. See U.S. Ser. No. 08/715,032, filed Sep. 17, 1996, the contents of which are expressly incorporated herein. Only hTI-2 was found to interact with the human rp protein carboxyl terminus (Table 3). This result shows that hTI-2 interacts with the conserved C-terminal domains on TUB-like proteins such as rp and that either hTI-2 regulates TUB-like proteins or TUB-like proteins regulate hTI-2 function. In addition, specific interaction of hTI-2 with the human rp protein provides a functional assay for the human rp protein. This assay can be configured to screen for drugs that inhibit binding of the human rp protein to hTI-2 or drugs that compete for binding to the human rp protein with hTI-2. Also, this assay can be configured to determine if mutant forms of the rp protein can bind to hTI-2. If a mutant version of the human rp protein is unable to bind to hTI-2, it would indicate that the mutation in question had led to a loss of at least one function (hTI-2 binding) of the human rp protein.

```
                           SEQUENCE LISTING

(1) GENERAL INFORMATION:

   (iii) NUMBER OF SEQUENCES: 16


(2) INFORMATION FOR SEQ ID NO: 1:

     (i) SEQUENCE CHARACTERISTICS:
          (A) LENGTH: 2184 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 569..1616

    (xi) SEQUENCE DESCRIPTION: SEQ ID NO: 1:

GAATTCCGGG AAGCTGAATG GAAGCCGGGG AGAAGTGTTG AAAGTGGAAA CCCAAGCCCA      60

GGGGAGATCC CTAGGGTGAG GAGCCCGAGG GGGTGCGCCC AGGCTTGGGG GTAGCGGGTA     120

GAGGCGCTGC CTCGCGGACC CGCGGATGGG ACCCTGTCTG AACCCCGCAT CTCGGCTCAG     180

CTGGGCGGAG GGGGAGGCCG CGGGAGGAGC CTTCCCCAGA CCCAGCCCAG GCCCGGGCGC     240

CGCAGACGGT CTACGCCAGG TTCCTCAGGG ACCCCGAGGC CAAGAAGCGC GACCCCCGGG     300

AAACCTTTCT GGTAGCCCGT GCCCCAGACG CGGAGGACGA GGAGGAGGAG GAAGAGGAGG     360

ACGAGGAGGA CGAAGAAGAT GAGCMGARGA AAAGAAAGAG AAAATCCTTC TGCCTCCCAA     420

GAARCCCCTG AGAGAGAAGA GCTCCGCAGA CCTGAANGAN AAGAAGGCCA ANGCCCASGG     480

CCCAAGGGGA GACCTGGGAA GCCCTGACCC CCCACCGAAA CCTCTGCGTG TTAGGAATAA     540

GGAAGCTCCA GCAGGGGAGG GGACCAAG ATG AGA AAG ACC AAG AAG AAA GGG       592
                               Met Arg Lys Thr Lys Lys Lys Gly
                                 1               5

TCT GGG GAG GCC GAC AAG GAC CCC TCA GGG AGC CCA GCC AGT GCG AGG      640
Ser Gly Glu Ala Asp Lys Asp Pro Ser Gly Ser Pro Ala Ser Ala Arg
     10                  15                  20

AAG AGC CCA GCA GCC ATG TTT CTG GTT GGG GAA GGC AGT CCT GAC AAG      688
Lys Ser Pro Ala Ala Met Phe Leu Val Gly Glu Gly Ser Pro Asp Lys
 25                  30                  35                  40

AAA GCC CTG AAG AAG AAA GGC ACT CCC AAA GGC GCG AGG AAG GAG GAA      736
Lys Ala Leu Lys Lys Lys Gly Thr Pro Lys Gly Ala Arg Lys Glu Glu
                 45                  50                  55
```

-continued

```
GAA GAG GAG GAG GAG GCA GCT ACG GTG ACA AAG AAC AGC AAT CAA AAG      784
Glu Glu Glu Glu Glu Ala Ala Thr Val Thr Lys Asn Ser Asn Gln Lys
            60                  65                  70

GGC AAA GCC AAA GGA AAA GGC AAA AAG AAA GCG AAG GAG GAG AGG GCC      832
Gly Lys Ala Lys Gly Lys Gly Lys Lys Lys Ala Lys Glu Glu Arg Ala
        75                  80                  85

CCG TCT CCC CCC GTG GAG GTG GAC GAA CCC CGG GAG TTT GTG CTC CGG      880
Pro Ser Pro Pro Val Glu Val Asp Glu Pro Arg Glu Phe Val Leu Arg
    90                  95                  100

CCT GCC CCC CAG GGC CGC ACG GTG CGC TGC CGG CTG ACC CGG GAC AAA      928
Pro Ala Pro Gln Gly Arg Thr Val Arg Cys Arg Leu Thr Arg Asp Lys
105                 110                 115                 120

AAG GGC ATG GAT CGA GGC ATG TAT CCC TCC TAC TTC CTG CAC CTG GAC      976
Lys Gly Met Asp Arg Gly Met Tyr Pro Ser Tyr Phe Leu His Leu Asp
                125                 130                 135

ACG GAG AAG AAG GTG TTC CTC TTG GCT GGC AGG AAA CGA AAA CGG AGC     1024
Thr Glu Lys Lys Val Phe Leu Leu Ala Gly Arg Lys Arg Lys Arg Ser
            140                 145                 150

AAG ACA GCC AAT TAC CTC ATC TCC ATC GAC CCT ACC AAT CTG TCC CGA     1072
Lys Thr Ala Asn Tyr Leu Ile Ser Ile Asp Pro Thr Asn Leu Ser Arg
        155                 160                 165

GGA GGG GAG AAT TTC ATC GGG AAG CTG AGG TCC AAC CTC CTG GGG AAC     1120
Gly Gly Glu Asn Phe Ile Gly Lys Leu Arg Ser Asn Leu Leu Gly Asn
    170                 175                 180

CGC TTC ACG GTC TTT GAC AAC GGG CAG AAC CCA CAG CGT GGG TAC AGC     1168
Arg Phe Thr Val Phe Asp Asn Gly Gln Asn Pro Gln Arg Gly Tyr Ser
185                 190                 195                 200

ACT AAT GTG GCA AGC CTT CGG CAG GAG CTG GCA GCT GTG ATC TAT GAA     1216
Thr Asn Val Ala Ser Leu Arg Gln Glu Leu Ala Ala Val Ile Tyr Glu
                205                 210                 215

ACC AAC GTG CTG GGC TTC CGT GGC CCC CGG CGC ATG ACC GTC ATC ATT     1264
Thr Asn Val Leu Gly Phe Arg Gly Pro Arg Arg Met Thr Val Ile Ile
            220                 225                 230

CCT GGC ATG AGT GCG GAG AAC GAG AGG GTC CCC ATC CGG CCC CGA AAT     1312
Pro Gly Met Ser Ala Glu Asn Glu Arg Val Pro Ile Arg Pro Arg Asn
        235                 240                 245

GCT AGT GAC GGC CTG CTG GTG CGC TGG CAG AAC AAG ACG CTG GAG AGC     1360
Ala Ser Asp Gly Leu Leu Val Arg Trp Gln Asn Lys Thr Leu Glu Ser
    250                 255                 260

CTC ATA GAA CTG CAC AAC AAG CCA CCT GTC TGG AAC GAT GAC AGT GGC     1408
Leu Ile Glu Leu His Asn Lys Pro Pro Val Trp Asn Asp Asp Ser Gly
265                 270                 275                 280

TCC TAC ACC CTC AAC TTC CAA GGC CGG GTC ACC CAG GCC TCA GTC AAG     1456
Ser Tyr Thr Leu Asn Phe Gln Gly Arg Val Thr Gln Ala Ser Val Lys
                285                 290                 295

AAC TTC CAG ATT GTC CAC GCT GAT GAC CCC GAC TAT ATC GTG CTG CAG     1504
Asn Phe Gln Ile Val His Ala Asp Asp Pro Asp Tyr Ile Val Leu Gln
            300                 305                 310

TTC GGC CGC GTG GCG GAG GAC GCC TTC ACC CTA GAC TAC CGG TAC CCG     1552
Phe Gly Arg Val Ala Glu Asp Ala Phe Thr Leu Asp Tyr Arg Tyr Pro
        315                 320                 325

CTG TGC GCC CTG CAG GCC TTC GCC ATC GCC CTC TCC AGT TTC GAC GGG     1600
Leu Cys Ala Leu Gln Ala Phe Ala Ile Ala Leu Ser Ser Phe Asp Gly
    330                 335                 340

AAG CTG GCC TGC GAG T GACCCCAGCA GCCCCTCAGC GCCCCCAGAG CCCGTCAGCG   1656
Lys Leu Ala Cys Glu
345

TGGGGGAAAG GATTCAGTGG AGGCTGGCAG GGTCCCTCCA GCAAAGCTCC CGCGGAAAAC   1716

TGCTCCTGTG TCGGGGCTGA CCTCTCACTG CCTCTCGGTG ACCTCCGTCC TCTCCCCAGC   1776
```

-continued

```
CTGGCACAGG CCGAGGCAGG AGGAGCCCGG ACGGCGGGTA GGACGGAGAT GAAGAACATC   1836

TGGAGTTGGA GCCGCACATC TGGTCTCGGA GCTCGCCTGC GCCGCTGTGC CCCCCTCCTC   1896

CCCGCGCCCC AGTCACTTCC TGTCCGGGAG CAGTAGTCAG TGTTGTTTTA ACCTCCCCTC   1956

TCCCCGGGAC CGCGCTAGGG CTCCGAGGAG CTGGGGCGGG CTAGGAGGAG GGGGTAGGTG   2016

ATGGGGGACG AGGGCCAGGC ACCCACATCC CCAATAAAGC CGCGTCCTTG GCMAAAAAAA   2076

AAAAAAAAAA AAAAAAAAAA AAAAAAAAAA AAAAAAAAAA AAAAAAAAAA AAAAAAAAAA   2136

AAAAAAAAAA AAAAAAAAAA AAAAAAAAAA AAAAAAAAAC CGGAATTC                2184
```

(2) INFORMATION FOR SEQ ID NO: 2:

(i) SEQUENCE CHARACTERISTICS:
(A) LENGTH: 349 amino acids
(B) TYPE: amino acid
(D) TOPOLOGY: linear (ii) MOLECULE TYPE: protein (xi) SEQUENCE DESCRIPTION: SEQ ID NO: 2:

```
Met Arg Lys Thr Lys Lys Lys Gly Ser Gly Glu Ala Asp Lys Asp Pro
  1               5                  10                  15

Ser Gly Ser Pro Ala Ser Ala Arg Lys Ser Pro Ala Ala Met Phe Leu
             20                  25                  30

Val Gly Glu Gly Ser Pro Asp Lys Lys Ala Leu Lys Lys Lys Gly Thr
         35                  40                  45

Pro Lys Gly Ala Arg Lys Glu Glu Glu Glu Glu Glu Glu Ala Ala Thr
     50                  55                  60

Val Thr Lys Asn Ser Asn Gln Lys Gly Lys Ala Lys Gly Lys Gly Lys
 65                  70                  75                  80

Lys Lys Ala Lys Glu Glu Arg Ala Pro Ser Pro Pro Val Glu Val Asp
                 85                  90                  95

Glu Pro Arg Glu Phe Val Leu Arg Pro Ala Pro Gln Gly Arg Thr Val
            100                 105                 110

Arg Cys Arg Leu Thr Arg Asp Lys Lys Gly Met Asp Arg Gly Met Tyr
        115                 120                 125

Pro Ser Tyr Phe Leu His Leu Asp Thr Glu Lys Lys Val Phe Leu Leu
    130                 135                 140

Ala Gly Arg Lys Arg Lys Arg Ser Lys Thr Ala Asn Tyr Leu Ile Ser
145                 150                 155                 160

Ile Asp Pro Thr Asn Leu Ser Arg Gly Gly Glu Asn Phe Ile Gly Lys
                165                 170                 175

Leu Arg Ser Asn Leu Leu Gly Asn Arg Phe Thr Val Phe Asp Asn Gly
            180                 185                 190

Gln Asn Pro Gln Arg Gly Tyr Ser Thr Asn Val Ala Ser Leu Arg Gln
        195                 200                 205

Glu Leu Ala Ala Val Ile Tyr Glu Thr Asn Val Leu Gly Phe Arg Gly
    210                 215                 220

Pro Arg Arg Met Thr Val Ile Ile Pro Gly Met Ser Ala Glu Asn Glu
225                 230                 235                 240

Arg Val Pro Ile Arg Pro Arg Asn Ala Ser Asp Gly Leu Leu Val Arg
                245                 250                 255

Trp Gln Asn Lys Thr Leu Glu Ser Leu Ile Glu Leu His Asn Lys Pro
            260                 265                 270

Pro Val Trp Asn Asp Asp Ser Gly Ser Tyr Thr Leu Asn Phe Gln Gly
```

-continued

```
        275                 280                 285

Arg Val Thr Gln Ala Ser Val Lys Asn Phe Gln Ile Val His Ala Asp
    290                 295                 300

Asp Pro Asp Tyr Ile Val Leu Gln Phe Gly Arg Val Ala Glu Asp Ala
305                 310                 315                 320

Phe Thr Leu Asp Tyr Arg Tyr Pro Leu Cys Ala Leu Gln Ala Phe Ala
                325                 330                 335

Ile Ala Leu Ser Ser Phe Asp Gly Lys Leu Ala Cys Glu
            340                 345


(2) INFORMATION FOR SEQ ID NO: 3:

     (i) SEQUENCE CHARACTERISTICS:
          (A) LENGTH: 1047 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..1048

    (xi) SEQUENCE DESCRIPTION: SEQ ID NO: 3:

ATG AGA AAG ACC AAG AAG AAA GGG TCT GGG GAG GCC GAC AAG GAC CCC        48
Met Arg Lys Thr Lys Lys Lys Gly Ser Gly Glu Ala Asp Lys Asp Pro
  1               5                  10                  15

TCA GGG AGC CCA GCC AGT GCG AGG AAG AGC CCA GCA GCC ATG TTT CTG        96
Ser Gly Ser Pro Ala Ser Ala Arg Lys Ser Pro Ala Ala Met Phe Leu
            20                  25                  30

GTT GGG GAA GGC AGT CCT GAC AAG AAA GCC CTG AAG AAG AAA GGC ACT       144
Val Gly Glu Gly Ser Pro Asp Lys Lys Ala Leu Lys Lys Lys Gly Thr
        35                  40                  45

CCC AAA GGC GCG AGG AAG GAG GAA GAA GAG GAG GAG GAG GCA GCT ACG       192
Pro Lys Gly Ala Arg Lys Glu Glu Glu Glu Glu Glu Glu Ala Ala Thr
     50                  55                  60

GTG ACA AAG AAC AGC AAT CAA AAG GGC AAA GCC AAA GGA AAA GGC AAA       240
Val Thr Lys Asn Ser Asn Gln Lys Gly Lys Ala Lys Gly Lys Gly Lys
 65                  70                  75                  80

AAG AAA GCG AAG GAG GAG AGG GCC CCG TCT CCC CCC GTG GAG GTG GAC       288
Lys Lys Ala Lys Glu Glu Arg Ala Pro Ser Pro Pro Val Glu Val Asp
                 85                  90                  95

GAA CCC CGG GAG TTT GTG TTC CGG CCT GCC CCC CAG GGC CGC ACG GTG       336
Glu Pro Arg Glu Phe Val Phe Arg Pro Ala Pro Gln Gly Arg Thr Val
            100                 105                 110

CGC TGC CGG CTG ACC CGG GAC AAA AAG GGC ATG GAT CGA GGC ATG TAT       384
Arg Cys Arg Leu Thr Arg Asp Lys Lys Gly Met Asp Arg Gly Met Tyr
        115                 120                 125

CCC TCC TAC TTC CTG CAC CTG GAC ACG GAG AAG AAG GTG TTC CTC TTG       432
Pro Ser Tyr Phe Leu His Leu Asp Thr Glu Lys Lys Val Phe Leu Leu
    130                 135                 140

GCT GGC AGG AAA CGA AAA CGG AGC AAG ACA GCC AAT TAC CTC ATC TCC       480
Ala Gly Arg Lys Arg Lys Arg Ser Lys Thr Ala Asn Tyr Leu Ile Ser
145                 150                 155                 160

ATC GAC CCT ACC AAT CTG TCC CGA GGA GGG GAG AAT TTC ATC GGG AAG       528
Ile Asp Pro Thr Asn Leu Ser Arg Gly Gly Glu Asn Phe Ile Gly Lys
                165                 170                 175

CTG AGG TCC AAC CTC CTG GGG AAC CGC TTC ACG GTC TTT GAC AAC GGG       576
Leu Arg Ser Asn Leu Leu Gly Asn Arg Phe Thr Val Phe Asp Asn Gly
            180                 185                 190
```

-continued

```
CAG AAC CCA CAG CGT GGG TAC AGC ACT AAT GTG GCA AGC CTT CGG CAG      624
Gln Asn Pro Gln Arg Gly Tyr Ser Thr Asn Val Ala Ser Leu Arg Gln
        195                 200                 205

GAG CTG GCA GCT GTG ATC TAT GAA ACC AAC GTG CTG GGC TTC CGT GGC      672
Glu Leu Ala Ala Val Ile Tyr Glu Thr Asn Val Leu Gly Phe Arg Gly
    210                 215                 220

CCC CGG CGC ATG ACC GTC ATC ATT CCT GGC ATG AGT GCG GAG AAC GAG      720
Pro Arg Arg Met Thr Val Ile Ile Pro Gly Met Ser Ala Glu Asn Glu
225                 230                 235                 240

AGG GTC CCC ATC CGG CCC CGA AAT GCT AGT GAC GGC CTG CTG GTG CGC      768
Arg Val Pro Ile Arg Pro Arg Asn Ala Ser Asp Gly Leu Leu Val Arg
                245                 250                 255

TGG CAG AAC AAG ACG CTG GAG AGC CTC ATA GAA CTG CAC AAC AAG CCA      816
Trp Gln Asn Lys Thr Leu Glu Ser Leu Ile Glu Leu His Asn Lys Pro
            260                 265                 270

CCT GTC TGG AAC GAT GAC AGT GGC TCC TAC ACC CTC AAC TTC CAA GGC      864
Pro Val Trp Asn Asp Asp Ser Gly Ser Tyr Thr Leu Asn Phe Gln Gly
        275                 280                 285

CGG GTC ACC CAG GCC TCA GTC AAG AAC TTC CAG ATT GTC CAC GCT GAT      912
Arg Val Thr Gln Ala Ser Val Lys Asn Phe Gln Ile Val His Ala Asp
    290                 295                 300

GAC CCC GAC TAT ATC GTG CTG CAG TTC GGC CGC GTG GCG GAG GAC GCC      960
Asp Pro Asp Tyr Ile Val Leu Gln Phe Gly Arg Val Ala Glu Asp Ala
305                 310                 315                 320

TTC ACC CTA GAC TAC CGG TAC CCG CTG TGC GCC CTG CAG GCC TTC GCC     1008
Phe Thr Leu Asp Tyr Arg Tyr Pro Leu Cys Ala Leu Gln Ala Phe Ala
                325                 330                 335

ATC GCC CTC TCC AGT TTC GAC GGG AAG CTG GCC TGC GAG                 1047
Ile Ala Leu Ser Ser Phe Asp Gly Lys Leu Ala Cys Glu
            340                 345
```

(2) INFORMATION FOR SEQ ID NO: 4:

(i) SEQUENCE CHARACTERISTICS:
(A) LENGTH: 1338 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..858

(xi) SEQUENCE DESCRIPTION: SEQ ID NO: 4:

```
GTG ATA AAG AAC AGC AAT CAA AAG GGC AAA GCC AAA GGA AAA GGC AAA       48
Val Ile Lys Asn Ser Asn Gln Lys Gly Lys Ala Lys Gly Lys Gly Lys
  1               5                  10                  15

AAG AAA GCG AAG GAG GAG AGG GCC CCG TCT CCC CCC GTG GAG GTG GAC       96
Lys Lys Ala Lys Glu Glu Arg Ala Pro Ser Pro Pro Val Glu Val Asp
            20                  25                  30

GAA CCC CGG GAG TTT GTG CTC CGG CCT GCC CCC CAG GGC CGC ACG GTG      144
Glu Pro Arg Glu Phe Val Leu Arg Pro Ala Pro Gln Gly Arg Thr Val
        35                  40                  45

CGC TGC CGG CTG ACC CGG GAC AAA AAG GGC ATG GAT CGA GGC ATG TAT      192
Arg Cys Arg Leu Thr Arg Asp Lys Lys Gly Met Asp Arg Gly Met Tyr
    50                  55                  60

CCC TCC TAC TTC CTG CAC CTG GAC ACG GAG AAG AAG GTG TTC CTC TTG      240
Pro Ser Tyr Phe Leu His Leu Asp Thr Glu Lys Lys Val Phe Leu Leu
 65                  70                  75                  80

GCT GGC AGG AAA CGA AAA CGG AGC AAG ACA GCC AAT TAC CTC ATC TCC      288
Ala Gly Arg Lys Arg Lys Arg Ser Lys Thr Ala Asn Tyr Leu Ile Ser
```

-continued

```
                 85                  90                  95

ATC GAC CCT ACC AAT CTG TCC CGA GGA GGG GAG AAT TTC ATC GGG AAG      336
Ile Asp Pro Thr Asn Leu Ser Arg Gly Gly Glu Asn Phe Ile Gly Lys
            100                 105                 110

CTG AGG TCC AAC CTC CTG GGG AAC CGC TTC ACG GTC TTT GAC AAC GGG      384
Leu Arg Ser Asn Leu Leu Gly Asn Arg Phe Thr Val Phe Asp Asn Gly
        115                 120                 125

CAG AAC CCA CAG CGT GGG TAC AGC ACT AAT GTG GCA AGC CTT CGG CAG      432
Gln Asn Pro Gln Arg Gly Tyr Ser Thr Asn Val Ala Ser Leu Arg Gln
    130                 135                 140

GAG CTG GCA GCT GTG ATC TAT GAA ACC AAC GTG CTG GGC TTC CGT GGC      480
Glu Leu Ala Ala Val Ile Tyr Glu Thr Asn Val Leu Gly Phe Arg Gly
145                 150                 155                 160

CCC CGG CGC ATG ACC GTC ATC ATT CCT GGC ATG AGT GCG GAG AAC GAG      528
Pro Arg Arg Met Thr Val Ile Ile Pro Gly Met Ser Ala Glu Asn Glu
                165                 170                 175

AGG GTC CCC ATC CGG CCC CGA AAT GCT AGT GAC GGC CTG CTG GTG CGC      576
Arg Val Pro Ile Arg Pro Arg Asn Ala Ser Asp Gly Leu Leu Val Arg
            180                 185                 190

TGG CAG AAC AAG ACG CTG GAG AGC CTC ATA GAA CTG CAC AAC AAG CCA      624
Trp Gln Asn Lys Thr Leu Glu Ser Leu Ile Glu Leu His Asn Lys Pro
        195                 200                 205

CCT GTC TGG AAC GAT GAC AGT GGC TCC TAC ACC CTC AAC TTC CAA GGC      672
Pro Val Trp Asn Asp Asp Ser Gly Ser Tyr Thr Leu Asn Phe Gln Gly
    210                 215                 220

CGG GTC ACC CAG GCC TCA GTC AAG AAC TTC CAG ATT GTC CAC GCT GAT      720
Arg Val Thr Gln Ala Ser Val Lys Asn Phe Gln Ile Val His Ala Asp
225                 230                 235                 240

GAC CCC GAC TAT ATC GTG CTG CAG TTC GGC CGC GTG GCG GAG GAC GCC      768
Asp Pro Asp Tyr Ile Val Leu Gln Phe Gly Arg Val Ala Glu Asp Ala
                245                 250                 255

TTC ACC CTA GAC TAC CGG TAC CCG CTG TGC GCC CTG CAG GCC TTC GCC      816
Phe Thr Leu Asp Tyr Arg Tyr Pro Leu Cys Ala Leu Gln Ala Phe Ala
            260                 265                 270

ATC GCC CTC TCC AGT TTC GAC GGG AAG CTG GCC TGC GAG TGACCCCAGC       865
Ile Ala Leu Ser Ser Phe Asp Gly Lys Leu Ala Cys Glu
        275                 280                 285

AGCCCCTCAG CGCCCCCAGA GCCCGTCAGC GTGGGGGAAA GGATTCAGTG GAGGCTGGCA    925

GGGTCCCTCC AGCAAAGCTC CCGCGGAAAA CTGCTCCTGT GTCGGGGCTG ACCTCTCACT    985

GCCTCTCGGT GACCTCCGTC CTCTCCCCAG CCTGGCACAG GCCGAGGCAG GAGGAGCCCG   1045

GACGGCGGGT AGGACGGAGA TGAAGAACAT CTGGAGTTGG AGCCGCACAT CTGGTCTCGG   1105

AGCTCGCCTG CGCCGCTGTG CCCCCCTCCT CCCCGCGCCC CAGTCACTTC CTGTCCGGGA   1165

GCAGTAGTCA TTGTTGTTTT AACCTCCCCT CTCCCCGGGA CCGCGCTAGG GCTCCGAGGA   1225

GCTGGGGCGG GCTAGGAGGA GGGGGTAGGT GATGGGGGAC GAGGGCCAGG CACCCACATC   1285

CCCAATAAAG CCGCGTCCTT GGCAAAAAAA AAAAAAAAAA AAAAAAAAAA AAA          1338
```

(2) INFORMATION FOR SEQ ID NO: 5:

(i) SEQUENCE CHARACTERISTICS:
(A) LENGTH: 285 amino acids
(B) TYPE: amino acid
(D) TOPOLOGY: linear (ii) MOLECULE TYPE: protein (xi) SEQUENCE DESCRIPTION: SEQ ID NO: 5:

```
Val Ile Lys Asn Ser Asn Gln Lys Gly Lys Ala Lys Gly Lys Gly Lys
```

-continued

```
1               5                   10                  15

Lys Lys Ala Lys Glu Glu Arg Ala Pro Ser Pro Pro Val Glu Val Asp
            20                  25                  30

Glu Pro Arg Glu Phe Val Leu Arg Pro Ala Pro Gln Gly Arg Thr Val
        35                  40                  45

Arg Cys Arg Leu Thr Arg Asp Lys Lys Gly Met Asp Arg Gly Met Tyr
    50                  55                  60

Pro Ser Tyr Phe Leu His Leu Asp Thr Glu Lys Lys Val Phe Leu Leu
65                  70                  75                  80

Ala Gly Arg Lys Arg Lys Arg Ser Lys Thr Ala Asn Tyr Leu Ile Ser
                85                  90                  95

Ile Asp Pro Thr Asn Leu Ser Arg Gly Gly Glu Asn Phe Ile Gly Lys
            100                 105                 110

Leu Arg Ser Asn Leu Leu Gly Asn Arg Phe Thr Val Phe Asp Asn Gly
        115                 120                 125

Gln Asn Pro Gln Arg Gly Tyr Ser Thr Asn Val Ala Ser Leu Arg Gln
    130                 135                 140

Glu Leu Ala Ala Val Ile Tyr Glu Thr Asn Val Leu Gly Phe Arg Gly
145                 150                 155                 160

Pro Arg Arg Met Thr Val Ile Ile Pro Gly Met Ser Ala Glu Asn Glu
                165                 170                 175

Arg Val Pro Ile Arg Pro Arg Asn Ala Ser Asp Gly Leu Leu Val Arg
            180                 185                 190

Trp Gln Asn Lys Thr Leu Glu Ser Leu Ile Glu Leu His Asn Lys Pro
        195                 200                 205

Pro Val Trp Asn Asp Asp Ser Gly Ser Tyr Thr Leu Asn Phe Gln Gly
    210                 215                 220

Arg Val Thr Gln Ala Ser Val Lys Asn Phe Gln Ile Val His Ala Asp
225                 230                 235                 240

Asp Pro Asp Tyr Ile Val Leu Gln Phe Gly Arg Val Ala Glu Asp Ala
                245                 250                 255

Phe Thr Leu Asp Tyr Arg Tyr Pro Leu Cys Ala Leu Gln Ala Phe Ala
            260                 265                 270

Ile Ala Leu Ser Ser Phe Asp Gly Lys Leu Ala Cys Glu
        275                 280                 285
```

(2) INFORMATION FOR SEQ ID NO: 6:

(i) SEQUENCE CHARACTERISTICS:
(A) LENGTH: 1801 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 139..1653

(xi) SEQUENCE DESCRIPTION: SEQ ID NO: 6:

```
CTGCAGGATT CGGCACGAGC AGCGGTCGGG CCGGGGAGGA TGCGGCCCGG GGCGGCCCGA      60

GAGTTGAGCA GGGTCCCCGC GCCAGCCCCG AGCGGTCCCG GCCACCGGAG CCGCAGCCGC     120

CGCCCCGCCC CCGGGAGA ATG ACT TCC AAG CCG CAT TCC GAC TGG ATT CCT       171
                    Met Thr Ser Lys Pro His Ser Asp Trp Ile Pro
                      1               5                   10

TAC AGT GTC CTA GAT GAT GAG GGC AGC AAC CTG AGG CAG CAG AAG CTC       219
```

-continued

```
Tyr Ser Val Leu Asp Asp Glu Gly Ser Asn Leu Arg Gln Gln Lys Leu
             15                  20                  25

GAC CGG CAG CGG GCC CTG TTG GAA CAG AAG CAG AAG AAG AAG CGC CAA      267
Asp Arg Gln Arg Ala Leu Leu Glu Gln Lys Gln Lys Lys Lys Arg Gln
         30                  35                  40

GAG CCC TTG ATG GTA CAG GCC AAT GCA GAT GGA CGG CCC CGG AGT CGG      315
Glu Pro Leu Met Val Gln Ala Asn Ala Asp Gly Arg Pro Arg Ser Arg
     45                  50                  55

CGA GCC CGG CAG TCA GAG GAG CAA GCC CCC CTG GTG GAG TCC TAC CTC      363
Arg Ala Arg Gln Ser Glu Glu Gln Ala Pro Leu Val Glu Ser Tyr Leu
 60                  65                  70                  75

AGC AGC AGT GGC AGC ACC AGC TAC CAA GTT CAA GAG GCC GAC TCG ATT      411
Ser Ser Ser Gly Ser Thr Ser Tyr Gln Val Gln Glu Ala Asp Ser Ile
                 80                  85                  90

GCC AGT GTA CAG CTG GGA GCC ACC CGC CCA CCA GCA CCA GCT TCA GCC      459
Ala Ser Val Gln Leu Gly Ala Thr Arg Pro Pro Ala Pro Ala Ser Ala
             95                 100                 105

AAG AAA TCC AAG GGA GCG GCT GCA TCT GGG GGC CAG GGT GGA GCC CCT      507
Lys Lys Ser Lys Gly Ala Ala Ala Ser Gly Gly Gln Gly Gly Ala Pro
        110                 115                 120

AGG AAG GAG AAG AAG GGA AAG CAT AAA GGC ACC AGC GGG CCA GCA ACT      555
Arg Lys Glu Lys Lys Gly Lys His Lys Gly Thr Ser Gly Pro Ala Thr
    125                 130                 135

CTG GCA GAA GAC AAG TCT GAG GCC CAA GGC CCA GTG CAG ATC TTG ACT      603
Leu Ala Glu Asp Lys Ser Glu Ala Gln Gly Pro Val Gln Ile Leu Thr
140                 145                 150                 155

GTG GGA CAG TCA GAC CAC GAC AAG GAT GCG GGA GAG ACA GCA GCC GGC      651
Val Gly Gln Ser Asp His Asp Lys Asp Ala Gly Glu Thr Ala Ala Gly
                160                 165                 170

GGG GGC GCA CAG CCC AGT GGG CAG GAC CTC CGT GCC ACG ATG CAG AGG      699
Gly Gly Ala Gln Pro Ser Gly Gln Asp Leu Arg Ala Thr Met Gln Arg
            175                 180                 185

AAG GGC ATC TCC AGC AGC ATG AGC TTT GAC GAG GAC GAG GAT GAG GAT      747
Lys Gly Ile Ser Ser Ser Met Ser Phe Asp Glu Asp Glu Asp Glu Asp
        190                 195                 200

GAA AAC AGC TCC AGC TCC TCC CAG CTA AAC AGC AAC ACC CGC CCT AGT      795
Glu Asn Ser Ser Ser Ser Ser Gln Leu Asn Ser Asn Thr Arg Pro Ser
    205                 210                 215

TCT GCC ACT AGC AGA AAG TCC ATC CGG GAG GCA GCT TCA GCC CCC AGC      843
Ser Ala Thr Ser Arg Lys Ser Ile Arg Glu Ala Ala Ser Ala Pro Ser
220                 225                 230                 235

CCA GCC GCC CCA GAG CCA CCA GTG GAT ATT GAG GTC CAG GAT CTA GAG      891
Pro Ala Ala Pro Glu Pro Pro Val Asp Ile Glu Val Gln Asp Leu Glu
                240                 245                 250

GAG TTT GCA CTG AGG CCA GCC CCA CAA GGG ATC ACC ATC AAA TGC CGC      939
Glu Phe Ala Leu Arg Pro Ala Pro Gln Gly Ile Thr Ile Lys Cys Arg
            255                 260                 265

ATC ACT CGG GAC AAG AAG GGG ATG GAC CGC GGC ATG TAC CCC ACC TAC      987
Ile Thr Arg Asp Lys Lys Gly Met Asp Arg Gly Met Tyr Pro Thr Tyr
        270                 275                 280

TTT CTG CAC CTA GAC CGT GAG GAT GGC AAG AAG GTG TTC CTC CTG GCG     1035
Phe Leu His Leu Asp Arg Glu Asp Gly Lys Lys Val Phe Leu Leu Ala
    285                 290                 295

GGC AGG AAG AGA AAG AGT AAA ACT TCC AAT TAC CTC ATC TCT GTG GAC     1083
Gly Arg Lys Arg Lys Ser Lys Thr Ser Asn Tyr Leu Ile Ser Val Asp
300                 305                 310                 315

CCA ACA GAC TTG TCT CGG GGA GGC GAT ACC TAT ATC GGG AAA TTG CGG     1131
Pro Thr Asp Leu Ser Arg Gly Gly Asp Thr Tyr Ile Gly Lys Leu Arg
                320                 325                 330
```

-continued

```
TCC AAC CTG ATG GGC ACC AAG TTC ACC GTT TAT GAC AAT GGC GTC AAC      1179
Ser Asn Leu Met Gly Thr Lys Phe Thr Val Tyr Asp Asn Gly Val Asn
            335                 340                 345

CCT CAG AAG GCA TCC TCT TCC ACG CTG GAA AGC GGA ACC TTG CGC CAG      1227
Pro Gln Lys Ala Ser Ser Ser Thr Leu Glu Ser Gly Thr Leu Arg Gln
        350                 355                 360

GAG CTG GCA GCG GTG TGC TAT GAG ACA AAT GTC CTA GGC TTC AAG GGA      1275
Glu Leu Ala Ala Val Cys Tyr Glu Thr Asn Val Leu Gly Phe Lys Gly
    365                 370                 375

CCT CGG AAG ATG AGT GTG ATC GTC CCA GGC ATG AAC ATG GTT CAT GAG      1323
Pro Arg Lys Met Ser Val Ile Val Pro Gly Met Asn Met Val His Glu
380                 385                 390                 395

AGA GTC TGT ATC CGC CCC CGC AAT GAA CAT GAG ACC CTG TTA GCA CGC      1371
Arg Val Cys Ile Arg Pro Arg Asn Glu His Glu Thr Leu Leu Ala Arg
                400                 405                 410

TGG CAG AAC AAG AAC ACG GAG AGC ATC ATT GAG CTG CAG AAC AAG ACG      1419
Trp Gln Asn Lys Asn Thr Glu Ser Ile Ile Glu Leu Gln Asn Lys Thr
            415                 420                 425

CCA GTC TGG AAT GAT GAC ACA CAG TCC TAT GTA CTT AAC TTC CAC GGC      1467
Pro Val Trp Asn Asp Asp Thr Gln Ser Tyr Val Leu Asn Phe His Gly
        430                 435                 440

CGT GTC ACA CAG GCT TCT GTG AAG AAC TTC CAG ATC ATC CAC GGC AAT      1515
Arg Val Thr Gln Ala Ser Val Lys Asn Phe Gln Ile Ile His Gly Asn
    445                 450                 455

GAC CCG GAC TAC ATC GTC ATG CAG TTT GGC CGG GTA GCA GAA GAT GTG      1563
Asp Pro Asp Tyr Ile Val Met Gln Phe Gly Arg Val Ala Glu Asp Val
460                 465                 470                 475

TTC ACC ATG GAT TAC AAC TAC CCA CTG TGT GCA CTG CAG GCC TTC GCC      1611
Phe Thr Met Asp Tyr Asn Tyr Pro Leu Cys Ala Leu Gln Ala Phe Ala
                480                 485                 490

ATT GCT CTG TCC AGC TTT GAC AGC AAG CTG GCC TGC GAG TAGAGGCCCC       1660
Ile Ala Leu Ser Ser Phe Asp Ser Lys Leu Ala Cys Glu
            495                 500

CCACTGCCGT TAGGTGGCCC AGTCCGGAGT GGAGCTTGCC TGCCTGCCAA GACAGGCCTG   1720

CCTACCCTCT GTTCATAGGC CCTCTATGGG CTTTCTGGTC TGACCAACCA GAGATTGGTT   1780

TGCTCTGCCT CTGCTGCTTG A                                             1801
```

(2) INFORMATION FOR SEQ ID NO: 7:

(i) SEQUENCE CHARACTERISTICS:
(A) LENGTH: 504 amino acids
(B) TYPE: amino acid
(D) TOPOLOGY: linear (ii) MOLECULE TYPE: protein (xi) SEQUENCE DESCRIPTION: SEQ ID NO: 7:

```
Met Thr Ser Lys Pro His Ser Asp Trp Ile Pro Tyr Ser Val Leu Asp
  1               5                  10                  15

Asp Glu Gly Ser Asn Leu Arg Gln Gln Lys Leu Asp Arg Gln Arg Ala
             20                  25                  30

Leu Leu Glu Gln Lys Gln Lys Lys Lys Arg Gln Glu Pro Leu Met Val
         35                  40                  45

Gln Ala Asn Ala Asp Gly Arg Pro Arg Ser Arg Arg Ala Arg Gln Ser
     50                  55                  60

Glu Glu Gln Ala Pro Leu Val Glu Ser Tyr Leu Ser Ser Ser Gly Ser
 65                  70                  75                  80

Thr Ser Tyr Gln Val Gln Glu Ala Asp Ser Ile Ala Ser Val Gln Leu
                 85                  90                  95
```

-continued

```
Gly Ala Thr Arg Pro Pro Ala Pro Ala Ser Ala Lys Lys Ser Lys Gly
            100                 105                 110

Ala Ala Ala Ser Gly Gly Gln Gly Gly Ala Pro Arg Lys Glu Lys Lys
        115                 120                 125

Gly Lys His Lys Gly Thr Ser Gly Pro Ala Thr Leu Ala Glu Asp Lys
    130                 135                 140

Ser Glu Ala Gln Gly Pro Val Gln Ile Leu Thr Val Gly Gln Ser Asp
145                 150                 155                 160

His Asp Lys Asp Ala Gly Glu Thr Ala Ala Gly Gly Gly Ala Gln Pro
                165                 170                 175

Ser Gly Gln Asp Leu Arg Ala Thr Met Gln Arg Lys Gly Ile Ser Ser
            180                 185                 190

Ser Met Ser Phe Asp Glu Asp Glu Asp Glu Asp Glu Asn Ser Ser Ser
        195                 200                 205

Ser Ser Gln Leu Asn Ser Asn Thr Arg Pro Ser Ser Ala Thr Ser Arg
    210                 215                 220

Lys Ser Ile Arg Glu Ala Ala Ser Ala Pro Ser Pro Ala Ala Pro Glu
225                 230                 235                 240

Pro Pro Val Asp Ile Glu Val Gln Asp Leu Glu Glu Phe Ala Leu Arg
                245                 250                 255

Pro Ala Pro Gln Gly Ile Thr Ile Lys Cys Arg Ile Thr Arg Asp Lys
            260                 265                 270

Lys Gly Met Asp Arg Gly Met Tyr Pro Thr Tyr Phe Leu His Leu Asp
        275                 280                 285

Arg Glu Asp Gly Lys Lys Val Phe Leu Leu Ala Gly Arg Lys Arg Lys
    290                 295                 300

Ser Lys Thr Ser Asn Tyr Leu Ile Ser Val Asp Pro Thr Asp Leu Ser
305                 310                 315                 320

Arg Gly Gly Asp Thr Tyr Ile Gly Lys Leu Arg Ser Asn Leu Met Gly
                325                 330                 335

Thr Lys Phe Thr Val Tyr Asp Asn Gly Val Asn Pro Gln Lys Ala Ser
            340                 345                 350

Ser Ser Thr Leu Glu Ser Gly Thr Leu Arg Gln Glu Leu Ala Ala Val
        355                 360                 365

Cys Tyr Glu Thr Asn Val Leu Gly Phe Lys Gly Pro Arg Lys Met Ser
    370                 375                 380

Val Ile Val Pro Gly Met Asn Met Val His Glu Arg Val Cys Ile Arg
385                 390                 395                 400

Pro Arg Asn Glu His Glu Thr Leu Leu Ala Arg Trp Gln Asn Lys Asn
                405                 410                 415

Thr Glu Ser Ile Ile Glu Leu Gln Asn Lys Thr Pro Val Trp Asn Asp
            420                 425                 430

Asp Thr Gln Ser Tyr Val Leu Asn Phe His Gly Arg Val Thr Gln Ala
        435                 440                 445

Ser Val Lys Asn Phe Gln Ile Ile His Gly Asn Asp Pro Asp Tyr Ile
    450                 455                 460

Val Met Gln Phe Gly Arg Val Ala Glu Asp Val Phe Thr Met Asp Tyr
465                 470                 475                 480

Asn Tyr Pro Leu Cys Ala Leu Gln Ala Phe Ala Ile Ala Leu Ser Ser
                485                 490                 495

Phe Asp Ser Lys Leu Ala Cys Glu
            500
```

-continued (2) INFORMATION FOR SEQ ID NO: 8:

(i) SEQUENCE CHARACTERISTICS:
(A) LENGTH: 1512 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..1515

(xi) SEQUENCE DESCRIPTION: SEQ ID NO: 8:

```
ATG ACT TCC AAG CCG CAT TCC GAC TGG ATT CCT TAC AGT GTC CTA GAT       48
Met Thr Ser Lys Pro His Ser Asp Trp Ile Pro Tyr Ser Val Leu Asp
  1               5                  10                  15

GAT GAG GGC AGC AAC CTG AGG CAG CAG AAG CTC GAC CGG CAG CGG GCC       96
Asp Glu Gly Ser Asn Leu Arg Gln Gln Lys Leu Asp Arg Gln Arg Ala
             20                  25                  30

CTG TTG GAA CAG AAG CAG AAG AAG AAG CGC CAA GAG CCC TTG ATG GTA      144
Leu Leu Glu Gln Lys Gln Lys Lys Lys Arg Gln Glu Pro Leu Met Val
         35                  40                  45

CAG GCC AAT GCA GAT GGA CGG CCC CGG AGT CGG CGA GCC CGG CAG TCA      192
Gln Ala Asn Ala Asp Gly Arg Pro Arg Ser Arg Arg Ala Arg Gln Ser
     50                  55                  60

GAG GAG CAA GCC CCC CTG GTG GAG TCC TAC CTC AGC AGC AGT GGC AGC      240
Glu Glu Gln Ala Pro Leu Val Glu Ser Tyr Leu Ser Ser Ser Gly Ser
 65                  70                  75                  80

ACC AGC TAC CAA GTT CAA GAG GCC GAC TCG ATT GCC AGT GTA CAG CTG      288
Thr Ser Tyr Gln Val Gln Glu Ala Asp Ser Ile Ala Ser Val Gln Leu
                 85                  90                  95

GGA GCC ACC CGC CCA CCA GCA CCA GCT TCA GCC AAG AAA TCC AAG GGA      336
Gly Ala Thr Arg Pro Pro Ala Pro Ala Ser Ala Lys Lys Ser Lys Gly
            100                 105                 110

GCG GCT GCA TCT GGG GGC CAG GGT GGA GCC CCT AGG AAG GAG AAG AAG      384
Ala Ala Ala Ser Gly Gly Gln Gly Gly Ala Pro Arg Lys Glu Lys Lys
        115                 120                 125

GGA AAG CAT AAA GGC ACC AGC GGG CCA GCA ACT CTG GCA GAA GAC AAG      432
Gly Lys His Lys Gly Thr Ser Gly Pro Ala Thr Leu Ala Glu Asp Lys
    130                 135                 140

TCT GAG GCC CAA GGC CCA GTG CAG ATC TTG ACT GTG GGA CAG TCA GAC      480
Ser Glu Ala Gln Gly Pro Val Gln Ile Leu Thr Val Gly Gln Ser Asp
145                 150                 155                 160

CAC GAC AAG GAT GCG GGA GAG ACA GCA GCC GGC GGG GGC GCA CAG CCC      528
His Asp Lys Asp Ala Gly Glu Thr Ala Ala Gly Gly Gly Ala Gln Pro
                165                 170                 175

AGT GGG CAG GAC CTC CGT GCC ACG ATG CAG AGG AAG GGC ATC TCC AGC      576
Ser Gly Gln Asp Leu Arg Ala Thr Met Gln Arg Lys Gly Ile Ser Ser
            180                 185                 190

AGC ATG AGC TTT GAC GAG GAC GAG GAT GAG GAT GAA AAC AGC TCC AGC      624
Ser Met Ser Phe Asp Glu Asp Glu Asp Glu Asp Glu Asn Ser Ser Ser
        195                 200                 205

TCC TCC CAG CTA AAC AGC AAC ACC CGC CCT AGT TCT GCC ACT AGC AGA      672
Ser Ser Gln Leu Asn Ser Asn Thr Arg Pro Ser Ser Ala Thr Ser Arg
    210                 215                 220

AAG TCC ATC CGG GAG GCA GCT TCA GCC CCC AGC CCA GCC GCC CCA GAG      720
Lys Ser Ile Arg Glu Ala Ala Ser Ala Pro Ser Pro Ala Ala Pro Glu
225                 230                 235                 240

CCA CCA GTG GAT ATT GAG GTC CAG GAT CTA GAG GAG TTT GCA CTG AGG      768
Pro Pro Val Asp Ile Glu Val Gln Asp Leu Glu Glu Phe Ala Leu Arg
```

-continued

```
            245                 250                 255

CCA GCC CCA CAA GGG ATC ACC ATC AAA TGC CGC ATC ACT CGG GAC AAG      816
Pro Ala Pro Gln Gly Ile Thr Ile Lys Cys Arg Ile Thr Arg Asp Lys
        260                 265                 270

AAG GGG ATG GAC CGC GGC ATG TAC CCC ACC TAC TTT CTG CAC CTA GAC      864
Lys Gly Met Asp Arg Gly Met Tyr Pro Thr Tyr Phe Leu His Leu Asp
    275                 280                 285

CGT GAG GAT GGC AAG AAG GTG TTC CTC CTG GCG GGC AGG AAG AGA AAG      912
Arg Glu Asp Gly Lys Lys Val Phe Leu Leu Ala Gly Arg Lys Arg Lys
    290                 295                 300

AGT AAA ACT TCC AAT TAC CTC ATC TCT GTG GAC CCA ACA GAC TTG TCT      960
Ser Lys Thr Ser Asn Tyr Leu Ile Ser Val Asp Pro Thr Asp Leu Ser
305                 310                 315                 320

CGG GGA GGC GAT ACC TAT ATC GGG AAA TTG CGG TCC AAC CTG ATG GGC     1008
Arg Gly Gly Asp Thr Tyr Ile Gly Lys Leu Arg Ser Asn Leu Met Gly
            325                 330                 335

ACC AAG TTC ACC GTT TAT GAC AAT GGC GTC AAC CCT CAG AAG GCA TCC     1056
Thr Lys Phe Thr Val Tyr Asp Asn Gly Val Asn Pro Gln Lys Ala Ser
        340                 345                 350

TCT TCC ACG CTG GAA AGC GGA ACC TTG CGC CAG GAG CTG GCA GCG GTG     1104
Ser Ser Thr Leu Glu Ser Gly Thr Leu Arg Gln Glu Leu Ala Ala Val
    355                 360                 365

TGC TAT GAG ACA AAT GTC CTA GGC TTC AAG GGA CCT CGG AAG ATG AGT     1152
Cys Tyr Glu Thr Asn Val Leu Gly Phe Lys Gly Pro Arg Lys Met Ser
    370                 375                 380

GTG ATC GTC CCA GGC ATG AAC ATG GTT CAT GAG AGA GTC TGT ATC CGC     1200
Val Ile Val Pro Gly Met Asn Met Val His Glu Arg Val Cys Ile Arg
385                 390                 395                 400

CCC CGC AAT GAA CAT GAG ACC CTG TTA GCA CGC TGG CAG AAC AAG AAC     1248
Pro Arg Asn Glu His Glu Thr Leu Leu Ala Arg Trp Gln Asn Lys Asn
            405                 410                 415

ACG GAG AGC ATC ATT GAG CTG CAG AAC AAG ACG CCA GTC TGG AAT GAT     1296
Thr Glu Ser Ile Ile Glu Leu Gln Asn Lys Thr Pro Val Trp Asn Asp
        420                 425                 430

GAC ACA CAG TCC TAT GTA CTT AAC TTC CAC GGC CGT GTC ACA CAG GCT     1344
Asp Thr Gln Ser Tyr Val Leu Asn Phe His Gly Arg Val Thr Gln Ala
    435                 440                 445

TCT GTG AAG AAC TTC CAG ATC ATC CAC GGC AAT GAC CCG GAC TAC ATC     1392
Ser Val Lys Asn Phe Gln Ile Ile His Gly Asn Asp Pro Asp Tyr Ile
    450                 455                 460

GTC ATG CAG TTT GGC CGG GTA GCA GAA GAT GTG TTC ACC ATG GAT TAC     1440
Val Met Gln Phe Gly Arg Val Ala Glu Asp Val Phe Thr Met Asp Tyr
465                 470                 475                 480

AAC TAC CCA CTG TGT GCA CTG CAG GCC TTC GCC ATT GCT CTG TCC AGC     1488
Asn Tyr Pro Leu Cys Ala Leu Gln Ala Phe Ala Ile Ala Leu Ser Ser
            485                 490                 495

TTT GAC AGC AAG CTG GCC TGC GAG                                     1512
Phe Asp Ser Lys Leu Ala Cys Glu
        500
```

(2) INFORMATION FOR SEQ ID NO: 9:

(i) SEQUENCE CHARACTERISTICS:
- (A) LENGTH: 2040 base pairs
- (B) TYPE: nucleic acid
- (C) STRANDEDNESS: single
- (D) TOPOLOGY: linear (ii) MOLECULE TYPE: cDNA (ix) FEATURE:
- (A) NAME/KEY: CDS -continued (B) LOCATION: 153..1671

(xi) SEQUENCE DESCRIPTION: SEQ ID NO: 9:

```
TGGCGTGCAG CAGGGGCCTC GGCGGGGCCC AGCCCNCCGG TCCCGGGGAG GATACGTCCC     60

GGGGGCGGCC CGGGAGCTGA GCAGGCCCCC CGCGCCGGCC CCTCCGGGCC CCGGCCTCCA    120

GAGCCGCAGC CACCGCCCCG CCCCCGAGAG AC ATG ACT TCC AAG CCG CAT TCC      173
                                    Met Thr Ser Lys Pro His Ser
                                     1               5

GAC TGG ATT CCC TAC AGT GTC TTA GAT GAT GAG GGC AGA AAC CTG AGG      221
Asp Trp Ile Pro Tyr Ser Val Leu Asp Asp Glu Gly Arg Asn Leu Arg
        10                  15                  20

CAG CAG AAG CTT GAT CGG CAG CGG GCC CTG CTG GAG CAG AAG CAG AAG      269
Gln Gln Lys Leu Asp Arg Gln Arg Ala Leu Leu Glu Gln Lys Gln Lys
    25                  30                  35

AAG AAG CGC CAG GAG CCC CTG ATG GTG CAG GCC AAT GCA GAT GGG CGG      317
Lys Lys Arg Gln Glu Pro Leu Met Val Gln Ala Asn Ala Asp Gly Arg
 40                  45                  50                  55

CCC CGG AGC CGG CGG GCC CGG CAG TCA GAG GAA CAA GCC CCC CTG GTG      365
Pro Arg Ser Arg Arg Ala Arg Gln Ser Glu Glu Gln Ala Pro Leu Val
                60                  65                  70

GAG TCC TAC CTC AGC AGC AGT GGC AGC ACC AGC TAC CAA GTT CAA GAG      413
Glu Ser Tyr Leu Ser Ser Ser Gly Ser Thr Ser Tyr Gln Val Gln Glu
            75                  80                  85

GCC GAC TCA CTC GCC AGT GTG CAG CTG GGA GCC ACG CGC CCA ACA GCA      461
Ala Asp Ser Leu Ala Ser Val Gln Leu Gly Ala Thr Arg Pro Thr Ala
        90                  95                 100

CCA GCT TCA GCC AAG AGA ACC AAG GCG GCA GCT ACA GCA GGG GGC CAG      509
Pro Ala Ser Ala Lys Arg Thr Lys Ala Ala Ala Thr Ala Gly Gly Gln
    105                 110                 115

GGT GGC GCC GCT AGG AAG GAG AAG AAG GGA AAG CAC AAA GGC ACC AGC      557
Gly Gly Ala Ala Arg Lys Glu Lys Lys Gly Lys His Lys Gly Thr Ser
120                 125                 130                 135

GGG CCA GCA GCA CTG GCA GAA GAC AAG TCT GAG GCC CAA GGC CCA GTG      605
Gly Pro Ala Ala Leu Ala Glu Asp Lys Ser Glu Ala Gln Gly Pro Val
                140                 145                 150

CAG ATT CTG ACT GTG GGC CAG TCA GAC CAC GCC CAG GAC GCA GGG GAG      653
Gln Ile Leu Thr Val Gly Gln Ser Asp His Ala Gln Asp Ala Gly Glu
            155                 160                 165

ACG GCA GCT GGT GGG GGC GAA CGG CCC AGC GGG CAG GAT CTC CGT GCC      701
Thr Ala Ala Gly Gly Gly Glu Arg Pro Ser Gly Gln Asp Leu Arg Ala
        170                 175                 180

ACG ATG CAG AGG AAG GGC ATC TCC AGC AGC ATG AGC TTT GAC GAG GAT      749
Thr Met Gln Arg Lys Gly Ile Ser Ser Ser Met Ser Phe Asp Glu Asp
    185                 190                 195

GAG GAG GAT GAG GAG GAG AAT AGC TCC AGC TCC TCC CAG CTA AAT AGT      797
Glu Glu Asp Glu Glu Glu Asn Ser Ser Ser Ser Ser Gln Leu Asn Ser
200                 205                 210                 215

AAC ACC CGC CCC AGC TCT GCT ACT AGC AGG AAG TCC GTC AGG GAG GCA      845
Asn Thr Arg Pro Ser Ser Ala Thr Ser Arg Lys Ser Val Arg Glu Ala
                220                 225                 230

GCC TCA GCC CCT AGC CCA ACA GCT CCA GAG CAA CCA GTG GAC GTT GAG      893
Ala Ser Ala Pro Ser Pro Thr Ala Pro Glu Gln Pro Val Asp Val Glu
            235                 240                 245

GTC CAG GAT CTT GAG GAG TTT GCA CTG AGG CCG GCC CCC CAG GGT ATC      941
Val Gln Asp Leu Glu Glu Phe Ala Leu Arg Pro Ala Pro Gln Gly Ile
        250                 255                 260

ACC ATC AAA TGC CGC ATC ACT CGG GAC AAG AAA GGG ATG GAC CGG GGC      989
Thr Ile Lys Cys Arg Ile Thr Arg Asp Lys Lys Gly Met Asp Arg Gly
    265                 270                 275
```

-continued

```
ATG TAC CCC ACC TAC TTT CTG CAC CTG GAC CGT GAG GAT GGG AAG AAG     1037
Met Tyr Pro Thr Tyr Phe Leu His Leu Asp Arg Glu Asp Gly Lys Lys
280                 285                 290                 295

GTG TTC CTC CTG GCG GGA AGG AAG AGA AAG AAG AGT AAA ACT TCC AAT     1085
Val Phe Leu Leu Ala Gly Arg Lys Arg Lys Lys Ser Lys Thr Ser Asn
                300                 305                 310

TAC CTC ATC TCT GTG GAC CCA ACA GAC TTG TCT CGA GGA GGG GAC AGC     1133
Tyr Leu Ile Ser Val Asp Pro Thr Asp Leu Ser Arg Gly Gly Asp Ser
            315                 320                 325

TAT ATC GGG AAA CTG CGG TCC AAC TTG ATG GGC ACC AAG TTC ACT GTT     1181
Tyr Ile Gly Lys Leu Arg Ser Asn Leu Met Gly Thr Lys Phe Thr Val
        330                 335                 340

TAT GAC AAT GGA GTC AAC CCT CAG AAG GCC TCA TCC TCC ACT TTG GAA     1229
Tyr Asp Asn Gly Val Asn Pro Gln Lys Ala Ser Ser Ser Thr Leu Glu
    345                 350                 355

AGT GGA ACC TTA CGT CAG GAG CTG GCA GCT GTG TGC TAC GAG ACA AAC     1277
Ser Gly Thr Leu Arg Gln Glu Leu Ala Ala Val Cys Tyr Glu Thr Asn
360                 365                 370                 375

GTC TTA GGC TTC AAG GGG CCT CGG AAG ATG AGC GTG ATT GTC CCA GGC     1325
Val Leu Gly Phe Lys Gly Pro Arg Lys Met Ser Val Ile Val Pro Gly
                380                 385                 390

ATG AAC ATG GTT CAT GAG AGA GTC TCT ATC CGC CCC CGC AAC GAG CAT     1373
Met Asn Met Val His Glu Arg Val Ser Ile Arg Pro Arg Asn Glu His
            395                 400                 405

GAG ACA CTG CTA GCA CGC TGG CAG AAT AAG AAC ACG GAG AGT ATC ATC     1421
Glu Thr Leu Leu Ala Arg Trp Gln Asn Lys Asn Thr Glu Ser Ile Ile
        410                 415                 420

GAG CTG CAA AAC AAG ACA CCT GTC TGG AAT GAT GAC ACA CAG TCC TAT     1469
Glu Leu Gln Asn Lys Thr Pro Val Trp Asn Asp Asp Thr Gln Ser Tyr
    425                 430                 435

GTA CTC AAC TTC CAT GGG CGC GTC ACA CAG GCC TCC GTG AAG AAC TTC     1517
Val Leu Asn Phe His Gly Arg Val Thr Gln Ala Ser Val Lys Asn Phe
440                 445                 450                 455

CAG ATC ATC CAT GGC AAT GAC CCG GAC TAC ATC GTG ATG CAG TTT GGC     1565
Gln Ile Ile His Gly Asn Asp Pro Asp Tyr Ile Val Met Gln Phe Gly
                460                 465                 470

CGG GTA GCA GAG GAT GTG TTC ACC ATG GAT TAC AAC TAC CCG CTG TGT     1613
Arg Val Ala Glu Asp Val Phe Thr Met Asp Tyr Asn Tyr Pro Leu Cys
            475                 480                 485

GCA CTG CAG GCC TTT GCC ATT GCC CTG TCC AGC TTC GAC AGC AAG CTG     1661
Ala Leu Gln Ala Phe Ala Ile Ala Leu Ser Ser Phe Asp Ser Lys Leu
        490                 495                 500

GCG TGC GAG T AGAGGCCTCT TCGTGCCCTT TGGGGTTGCC CAGCCTGGAG           1711
Ala Cys Glu
    505

CGGAGCTTGC CTGCCTGCCT GTGGAGACAG CCCTGCCTAT CCTCTGTATA TAGGCCTTCC   1771

GCCAGATGAA GCTTTGGCCC TCAGTGGGCT CCCTGGCCCA GCCAGCCAGG AACTGGCTCC   1831

TTTGGCTCTG CTACTGAGGC AGGGGAGTAG TGGAGAGCGG GTGGGTGGGT GTTGAAGGGA   1891

TTGAGAATTA ATTCTTTCCA TGCCACGAGG ATCAACACAC ACTCCCACCC TTGGGTAGTA   1951

AGTGGTTGTT GTNAGTCGGT ACTTTACCAA AGCTTGAGCA ACCTCTTCCA AGCTTGGGAA   2011

AGGGCCGCAA AAAGGCATTA GGAGGGGAG                                     2040
```

(2) INFORMATION FOR SEQ ID NO: 10:

(i) SEQUENCE CHARACTERISTICS:
(A) LENGTH: 506 amino acids
(B) TYPE: amino acid

-continued

```
        (D) TOPOLOGY: linear

    (ii) MOLECULE TYPE: protein

    (xi) SEQUENCE DESCRIPTION: SEQ ID NO: 10:

Met Thr Ser Lys Pro His Ser Asp Trp Ile Pro Tyr Ser Val Leu Asp
  1               5                  10                  15

Asp Glu Gly Arg Asn Leu Arg Gln Gln Lys Leu Asp Arg Gln Arg Ala
             20                  25                  30

Leu Leu Glu Gln Lys Gln Lys Lys Lys Arg Gln Glu Pro Leu Met Val
         35                  40                  45

Gln Ala Asn Ala Asp Gly Arg Pro Arg Ser Arg Arg Ala Arg Gln Ser
     50                  55                  60

Glu Glu Gln Ala Pro Leu Val Glu Ser Tyr Leu Ser Ser Ser Gly Ser
 65                  70                  75                  80

Thr Ser Tyr Gln Val Gln Glu Ala Asp Ser Leu Ala Ser Val Gln Leu
                 85                  90                  95

Gly Ala Thr Arg Pro Thr Ala Pro Ala Ser Ala Lys Arg Thr Lys Ala
            100                 105                 110

Ala Ala Thr Ala Gly Gly Gln Gly Gly Ala Ala Arg Lys Glu Lys Lys
        115                 120                 125

Gly Lys His Lys Gly Thr Ser Gly Pro Ala Ala Leu Ala Glu Asp Lys
    130                 135                 140

Ser Glu Ala Gln Gly Pro Val Gln Ile Leu Thr Val Gly Gln Ser Asp
145                 150                 155                 160

His Ala Gln Asp Ala Gly Glu Thr Ala Ala Gly Gly Gly Glu Arg Pro
                165                 170                 175

Ser Gly Gln Asp Leu Arg Ala Thr Met Gln Arg Lys Gly Ile Ser Ser
            180                 185                 190

Ser Met Ser Phe Asp Glu Asp Glu Glu Asp Glu Glu Glu Asn Ser Ser
        195                 200                 205

Ser Ser Ser Gln Leu Asn Ser Asn Thr Arg Pro Ser Ser Ala Thr Ser
    210                 215                 220

Arg Lys Ser Val Arg Glu Ala Ala Ser Ala Pro Ser Pro Thr Ala Pro
225                 230                 235                 240

Glu Gln Pro Val Asp Val Glu Val Gln Asp Leu Glu Glu Phe Ala Leu
                245                 250                 255

Arg Pro Ala Pro Gln Gly Ile Thr Ile Lys Cys Arg Ile Thr Arg Asp
            260                 265                 270

Lys Lys Gly Met Asp Arg Gly Met Tyr Pro Thr Tyr Phe Leu His Leu
        275                 280                 285

Asp Arg Glu Asp Gly Lys Lys Val Phe Leu Leu Ala Gly Arg Lys Arg
    290                 295                 300

Lys Lys Ser Lys Thr Ser Asn Tyr Leu Ile Ser Val Asp Pro Thr Asp
305                 310                 315                 320

Leu Ser Arg Gly Gly Asp Ser Tyr Ile Gly Lys Leu Arg Ser Asn Leu
                325                 330                 335

Met Gly Thr Lys Phe Thr Val Tyr Asp Asn Gly Val Asn Pro Gln Lys
            340                 345                 350

Ala Ser Ser Ser Thr Leu Glu Ser Gly Thr Leu Arg Gln Glu Leu Ala
        355                 360                 365

Ala Val Cys Tyr Glu Thr Asn Val Leu Gly Phe Lys Gly Pro Arg Lys
    370                 375                 380

Met Ser Val Ile Val Pro Gly Met Asn Met Val His Glu Arg Val Ser
```

-continued

```
385                 390                 395                 400

Ile Arg Pro Arg Asn Glu His Glu Thr Leu Leu Ala Arg Trp Gln Asn
                405                 410                 415

Lys Asn Thr Glu Ser Ile Ile Glu Leu Gln Asn Lys Thr Pro Val Trp
            420                 425                 430

Asn Asp Asp Thr Gln Ser Tyr Val Leu Asn Phe His Gly Arg Val Thr
        435                 440                 445

Gln Ala Ser Val Lys Asn Phe Gln Ile Ile His Gly Asn Asp Pro Asp
    450                 455                 460

Tyr Ile Val Met Gln Phe Gly Arg Val Ala Glu Asp Val Phe Thr Met
465                 470                 475                 480

Asp Tyr Asn Tyr Pro Leu Cys Ala Leu Gln Ala Phe Ala Ile Ala Leu
                485                 490                 495

Ser Ser Phe Asp Ser Lys Leu Ala Cys Glu
            500                 505
```

(2) INFORMATION FOR SEQ ID NO: 11:

(i) SEQUENCE CHARACTERISTICS:
(A) LENGTH: 1518 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..1519

(xi) SEQUENCE DESCRIPTION: SEQ ID NO: 11:

```
ATG ACT TCC AAG CCG CAT TCC GAC TGG ATT CCC TAC AGT GTC TTA GAT       48
Met Thr Ser Lys Pro His Ser Asp Trp Ile Pro Tyr Ser Val Leu Asp
  1               5                  10                  15

GAT GAG GGC AGA AAC CTG AGG CAG CAG AAG CTT GAT CGG CAG CGG GCC       96
Asp Glu Gly Arg Asn Leu Arg Gln Gln Lys Leu Asp Arg Gln Arg Ala
             20                  25                  30

CTG CTG GAG CAG AAG CAG AAG AAG AAG CGC CAG GAG CCC CTG ATG GTG      144
Leu Leu Glu Gln Lys Gln Lys Lys Lys Arg Gln Glu Pro Leu Met Val
         35                  40                  45

CAG GCC AAT GCA GAT GGG CGG CCC CGG AGC CGG CGG GCC CGG CAG TCA      192
Gln Ala Asn Ala Asp Gly Arg Pro Arg Ser Arg Arg Ala Arg Gln Ser
     50                  55                  60

GAG GAA CAA GCC CCC CTG GTG GAG TCC TAC CTC AGC AGC AGT GGC AGC      240
Glu Glu Gln Ala Pro Leu Val Glu Ser Tyr Leu Ser Ser Ser Gly Ser
 65                  70                  75                  80

ACC AGC TAC CAA GTT CAA GAG GCC GAC TCA CTC GCC AGT GTG CAG CTG      288
Thr Ser Tyr Gln Val Gln Glu Ala Asp Ser Leu Ala Ser Val Gln Leu
                 85                  90                  95

GGA GCC ACG CGC CCA ACA GCA CCA GCT TCA GCC AAG AGA ACC AAG GCG      336
Gly Ala Thr Arg Pro Thr Ala Pro Ala Ser Ala Lys Arg Thr Lys Ala
            100                 105                 110

GCA GCT ACA GCA GGG GGC CAG GGT GGC GCC GCT AGG AAG GAG AAG AAG      384
Ala Ala Thr Ala Gly Gly Gln Gly Gly Ala Ala Arg Lys Glu Lys Lys
        115                 120                 125

GGA AAG CAC AAA GGC ACC AGC GGG CCA GCA GCA CTG GCA GAA GAC AAG      432
Gly Lys His Lys Gly Thr Ser Gly Pro Ala Ala Leu Ala Glu Asp Lys
    130                 135                 140

TCT GAG GCC CAA GGC CCA GTG CAG ATT CTG ACT GTG GGC CAG TCA GAC      480
Ser Glu Ala Gln Gly Pro Val Gln Ile Leu Thr Val Gly Gln Ser Asp
145                 150                 155                 160
```

-continued

```
CAC GCC CAG GAC GCA GGG GAG ACG GCA GCT GGT GGG GGC GAA CGG CCC      528
His Ala Gln Asp Ala Gly Glu Thr Ala Ala Gly Gly Gly Glu Arg Pro
                165                 170                 175

AGC GGG CAG GAT CTC CGT GCC ACG ATG CAG AGG AAG GGC ATC TCC AGC      576
Ser Gly Gln Asp Leu Arg Ala Thr Met Gln Arg Lys Gly Ile Ser Ser
            180                 185                 190

AGC ATG AGC TTT GAC GAG GAT GAG GAG GAT GAG GAG GAG AAT AGC TCC      624
Ser Met Ser Phe Asp Glu Asp Glu Glu Asp Glu Glu Glu Asn Ser Ser
        195                 200                 205

AGC TCC TCC CAG CTA AAT AGT AAC ACC CGC CCC AGC TCT GCT ACT AGC      672
Ser Ser Ser Gln Leu Asn Ser Asn Thr Arg Pro Ser Ser Ala Thr Ser
    210                 215                 220

AGG AAG TCC GTC AGG GAG GCA GCC TCA GCC CCT AGC CCA ACA GCT CCA      720
Arg Lys Ser Val Arg Glu Ala Ala Ser Ala Pro Ser Pro Thr Ala Pro
225                 230                 235                 240

GAG CAA CCA GTG GAC GTT GAG GTC CAG GAT CTT GAG GAG TTT GCA CTG      768
Glu Gln Pro Val Asp Val Glu Val Gln Asp Leu Glu Glu Phe Ala Leu
                245                 250                 255

AGG CCG GCC CCC CAG GGT ATC ACC ATC AAA TGC CGC ATC ACT CGG GAC      816
Arg Pro Ala Pro Gln Gly Ile Thr Ile Lys Cys Arg Ile Thr Arg Asp
            260                 265                 270

AAG AAA GGG ATG GAC CGG GGC ATG TAC CCC ACC TAC TTT CTG CAC CTG      864
Lys Lys Gly Met Asp Arg Gly Met Tyr Pro Thr Tyr Phe Leu His Leu
        275                 280                 285

GAC CGT GAG GAT GGG AAG AAG GTG TTC CTC CTG GCG GGA AGG AAG AGA      912
Asp Arg Glu Asp Gly Lys Lys Val Phe Leu Leu Ala Gly Arg Lys Arg
    290                 295                 300

AAG AAG AGT AAA ACT TCC AAT TAC CTC ATC TCT GTG GAC CCA ACA GAC      960
Lys Lys Ser Lys Thr Ser Asn Tyr Leu Ile Ser Val Asp Pro Thr Asp
305                 310                 315                 320

TTG TCT CGA GGA GGG GAC AGC TAT ATC GGG AAA CTG CGG TCC AAC TTG     1008
Leu Ser Arg Gly Gly Asp Ser Tyr Ile Gly Lys Leu Arg Ser Asn Leu
                325                 330                 335

ATG GGC ACC AAG TTC ACT GTT TAT GAC AAT GGA GTC AAC CCT CAG AAG     1056
Met Gly Thr Lys Phe Thr Val Tyr Asp Asn Gly Val Asn Pro Gln Lys
            340                 345                 350

GCC TCA TCC TCC ACT TTG GAA AGT GGA ACC TTA CGT CAG GAG CTG GCA     1104
Ala Ser Ser Ser Thr Leu Glu Ser Gly Thr Leu Arg Gln Glu Leu Ala
        355                 360                 365

GCT GTG TGC TAC GAG ACA AAC GTC TTA GGC TTC AAG GGG CCT CGG AAG     1152
Ala Val Cys Tyr Glu Thr Asn Val Leu Gly Phe Lys Gly Pro Arg Lys
    370                 375                 380

ATG AGC GTG ATT GTC CCA GGC ATG AAC ATG GTT CAT GAG AGA GTC TCT     1200
Met Ser Val Ile Val Pro Gly Met Asn Met Val His Glu Arg Val Ser
385                 390                 395                 400

ATC CGC CCC CGC AAC GAG CAT GAG ACA CTG CTA GCA CGC TGG CAG AAT     1248
Ile Arg Pro Arg Asn Glu His Glu Thr Leu Leu Ala Arg Trp Gln Asn
                405                 410                 415

AAG AAC ACG GAG AGT ATC ATC GAG CTG CAA AAC AAG ACA CCT GTC TGG     1296
Lys Asn Thr Glu Ser Ile Ile Glu Leu Gln Asn Lys Thr Pro Val Trp
            420                 425                 430

AAT GAT GAC ACA CAG TCC TAT GTA CTC AAC TTC CAT GGG CGC GTC ACA     1344
Asn Asp Asp Thr Gln Ser Tyr Val Leu Asn Phe His Gly Arg Val Thr
        435                 440                 445

CAG GCC TCC GTG AAG AAC TTC CAG ATC ATC CAT GGC AAT GAC CCG GAC     1392
Gln Ala Ser Val Lys Asn Phe Gln Ile Ile His Gly Asn Asp Pro Asp
    450                 455                 460

TAC ATC GTG ATG CAG TTT GGC CGG GTA GCA GAG GAT GTG TTC ACC ATG     1440
Tyr Ile Val Met Gln Phe Gly Arg Val Ala Glu Asp Val Phe Thr Met
```

-continued

```
465                 470                 475                 480

GAT TAC AAC TAC CCG CTG TGT GCA CTG CAG GCC TTT GCC ATT GCC CTG      1488
Asp Tyr Asn Tyr Pro Leu Cys Ala Leu Gln Ala Phe Ala Ile Ala Leu
                485                 490                 495

TCC AGC TTC GAC AGC AAG CTG GCG TGC GAG                              1518
Ser Ser Phe Asp Ser Lys Leu Ala Cys Glu
            500                 505
```

(2) INFORMATION FOR SEQ ID NO: 12:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 12:

```
CGTCCCCTCC CCTGGTTCTA C                                               21
```

(2) INFORMATION FOR SEQ ID NO: 13:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 13:

```
CGCTGACGGG CTCTGGGGGC                                                 20
```

(2) INFORMATION FOR SEQ ID NO: 14:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 14:

```
GCCAGCCTCC ACTGAATC                                                   18
```

(2) INFORMATION FOR SEQ ID NO: 15:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 15:

```
CGTGGAGGTG GACGAACC                                                   18
```

(2) INFORMATION FOR SEQ ID NO: 16:

(i) SEQUENCE CHARACTERISTICS:
(A) LENGTH: 18 base pairs
(B) TYPE: nucleic acid
(C) STRANDEDNESS: single
(D) TOPOLOGY: linear -continued

```
(ii) MOLECULE TYPE: cDNA

(xi) SEQUENCE DESCRIPTION: SEQ ID NO: 16:

CCGTGTCCAG GTGCAGGA                                                     18
```

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method of detecting aberrant or abnormal expression of a nucleic acid comprising the nucleotide sequence of SEQ ID NO:1, comprising:

a) contacting a sample containing a nucleic acid comprising the nucleotide sequence of SEQ ID NO:1 with a hybridization probe comprising at least 25 contiguous nucleotides from nucleotides 761–2098 of SEQ ID NO:1;

b) detecting expression of a nucleic acid molecule in said sample that hybridizes to said hybridization probe; and c) comparing the expression of the nucleic acid molecule in the sample that hybridizes to the hybridization probe with a standard, thereby detecting aberrant or abnormal expression of a nucleic acid comprising the nucleotide sequence of SEQ ID NO:1.

2. A method of detecting aberrant or abnormal expression of a nucleic acid comprising the nucleotide sequence of SEQ ID NO:1, comprising:

a) contacting a sample containing a nucleic acid comprising the nucleotide sequence of SEQ ID NO:1 with a first and a second amplification primer, said first primer comprising at least 25 contiguous nucleotides from nucleotides 761–2098 of SEQ ID NO:1 and said second primer comprising at least 25 contiguous nucleotides from the complement of nucleotides 761–2098 of SEQ ID NO:1;

b) incubating said sample under conditions that allow nucleic acid amplification;

c) detecting the presence of a nucleic acid molecule in said sample that is amplified; and d) comparing the expression of the nucleic acid molecule in the sample that is amplified with a standard, thereby detecting aberrant or abnormal expression of a nucleic acid comprising the nucleotide sequence of SEQ ID NO:1.

3. A method of detecting a mutation, polymorphism, insertion, deletion, or chromosomal rearrangement in SEQ ID NO:1 comprising:

a) contacting a sample containing a nucleic acid comprising the nucleotide sequence of SEQ ID NO:1 with a hybridization probe comprising at least 25 contiguous nucleotides from nucleotides 761–2098 of SEQ ID NO:1;

b) detecting the presence of a nucleic acid molecule in said sample that hybridizes to the hybridization probe; and c) comparing the sequence of the nucleic acid molecule in the sample that hybridizes to the hybridization probe with the sequence of the nucleic acid molecule set forth in SEQ ID NO:1, thereby detecting a mutation, polymorphism, insertion, deletion, or chromosomal rearrangement in SEQ ID NO:1.

4. A method of detecting a mutation, polymorphism, insertion, deletion, or chromosomal rearrangement in SEQ ID NO:1 comprising:

a) contacting a sample containing a nucleic acid comprising the nucleotide sequence of SEQ ID NO:1 with a first and a second amplification primer, said first primer comprising at least 25 contiguous nucleotides from nucleotides 761–2098 of SEQ ID NO:1 and said second primer comprising at least 25 contiguous nucleotides from the complement of nucleotides 761–2098 of SEQ ID NO:1;

b) incubating said sample under conditions that allow nucleic acid amplification; and c) detecting the presence of a nucleic acid molecule in the sample that is amplified; and d) comparing the sequence of the nucleic acid molecule in the sample that is amplified with the sequence of the nucleic acid molecule set forth in SEQ ID NO:1, thereby detecting a mutation, polymorphism, insertion, deletion, or chromosomal rearrangement in SEQ ID NO:1.

5. The method of any one of claims 1 or 3, wherein said hybridization probe is detectably labeled.

6. The method of any one of claims 2 or 4, wherein said amplified nucleic acid molecule is detected using a hybridization probe comprising at least 25 contiguous nucleotides from nucleotides 761–2098 of SEQ ID NO:1.

7. The method of any one of claims 1 or 3, wherein said sample obtained from said subject is subjected to agarose gel electrophoresis and southern blotting prior to contacting with said hybridization probe.

8. The method of any one of claims 2 or 4 wherein said sample obtained from said subject is subjected to agarose gel electrophoresis after said incubation step.

9. The method of any one of claims 1 or 3 wherein said method is used to detect mRNA in said sample.

10. The method of any one of claims 2 or 4 wherein said method is used to detect genomic DNA in said sample.

* * * * *